United States Patent
Akonur et al.

(10) Patent No.: US 8,868,350 B2
(45) Date of Patent: Oct. 21, 2014

(54) THERAPY PREDICTION AND OPTIMIZATION FOR RENAL FAILURE BLOOD THERAPY, ESPECIALLY HOME HEMODIALYSIS

(75) Inventors: Alp Akonur, Evanston, IL (US); John Kenneth Leypoldt, Libertyville, IL (US); Ying-Cheng Lo, Green Oaks, IL (US); Baris Ugur Agar, Chicago, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 830 days.

(21) Appl. No.: 13/088,044

(22) Filed: Apr. 15, 2011

(65) Prior Publication Data

US 2011/0257891 A1 Oct. 20, 2011

Related U.S. Application Data

(60) Provisional application No. 61/325,113, filed on Apr. 16, 2010, provisional application No. 61/388,315, filed on Sep. 30, 2010, provisional application No. 61/438,002, filed on Jan. 31, 2011.

(51) Int. Cl.
| | |
|---|---|
| G01N 33/48 | (2006.01) |
| A61M 1/16 | (2006.01) |
| A61M 1/36 | (2006.01) |
| G06F 19/00 | (2011.01) |

(52) U.S. Cl.
CPC ............... *A61M 1/16* (2013.01); *A61M 1/3609* (2014.02); *A61M 1/1603* (2014.02); *A61M 1/1613* (2014.02); *A61M 1/1611* (2014.02); *G06F 19/3481* (2013.01)
USPC ............. 702/19; 210/646; 604/5.01; 600/309

(58) Field of Classification Search
CPC ... A61M 1/16; A61M 1/3609; A61M 1/1611; A61M 1/1613; A61M 1/16013; G06F 19/3481; G01N 2800/347
USPC ............... 210/646, 647, 739, 96.2; 604/5.01, 604/4.01, 6.01, 6.09, 65–67; 702/19; 600/309, 322; 436/103–105
See application file for complete search history.

(56) References Cited

U.S. PATENT DOCUMENTS

| | | | |
|---|---|---|---|
| 2004/0048837 A1* | 3/2004 | Lazarus | ........................ 514/167 |
| 2008/0202591 A1 | 8/2008 | Grant et al. | |

(Continued)

FOREIGN PATENT DOCUMENTS

| | | |
|---|---|---|
| EP | 1 396 274 | 3/2004 |
| WO | 2011000086 | 1/2011 |
| WO | 2011041697 | 4/2011 |

OTHER PUBLICATIONS

JC Ayus et al, "Phosphorus balance and mineral metabolism with 3H daily hemodialysis", Dec. 27, 2006, Kidney International, 71, 336-342.*

(Continued)

*Primary Examiner* — John Breene
*Assistant Examiner* — Stephanie Bloss
(74) *Attorney, Agent, or Firm* — K&L Gates LLP

(57) ABSTRACT

A method of predicting serum phosphorus concentrations in a patient during hemodialysis includes measuring serum phosphorus concentrations of the patient over a hemodialysis treatment session time and an ultrafiltration rate calculated by a difference between pre- and post-dialytic body weight of the patient during an initial hemodialysis treatment session divided by a total treatment time of the treatment session and estimating a phosphorous mobilization clearance and a pre-dialysis distribution volume of phosphorus for the patient. Serum phosphorus concentrations of the patient can then be predicted at any time during any hemodialysis treatment session with the estimated phosphorous mobilization clearance and pre-dialysis distribution volume of phosphorus of the patient.

50 Claims, 24 Drawing Sheets

(56) References Cited

U.S. PATENT DOCUMENTS

| | | |
|---|---|---|
| 2008/0208103 A1 | 8/2008 | Demers et al. |
| 2008/0216898 A1 | 9/2008 | Grant et al. |
| 2009/0004033 A1 | 1/2009 | Demers et al. |
| 2009/0101549 A1 | 4/2009 | Kamen et al. |
| 2009/0105629 A1 | 4/2009 | Grant et al. |
| 2009/0107335 A1 | 4/2009 | Wilt et al. |
| 2009/0114582 A1 | 5/2009 | Grant et al. |
| 2010/0010423 A1 | 1/2010 | Yu et al. |
| 2010/0010424 A1 | 1/2010 | Yu et al. |
| 2010/0010426 A1 | 1/2010 | Childers et al. |
| 2010/0010427 A1 | 1/2010 | Yu et al. |
| 2010/0010428 A1 | 1/2010 | Yu et al. |
| 2010/0042035 A1* | 2/2010 | Moissl et al. ............... 604/5.04 |
| 2010/0042331 A1* | 2/2010 | Hamada et al. ............... 702/19 |
| 2010/0096330 A1 | 4/2010 | Gotch et al. |
| 2010/0192686 A1* | 8/2010 | Kamen et al. ............... 73/290 R |
| 2011/0079558 A1 | 4/2011 | Raimann et al. |

OTHER PUBLICATIONS

Alp Akonur et al, "Ultrafiltration Efficiency During Automated Peritoneal Dialysis Using Glucose-Based Solutions", 2008, Advances in Peritoneal Dialysis, vol. 24, 69-74.*

Columbian Office Action for Columbian Application No. 12207315, dated Sep. 30, 2013.

Columbian Office Action for Columbian Application No. 12207312, dated Feb. 27, 2014.

Heaf et al., "The Cellular Clearance Theory Does Not Explain the Post-dialytic Small Molecule Rebound," Scan J Urol Nephrol vol. 32, (1998), pp. 350-355.

Maasrani et al., "Urea, creatinine and phosphate kinetic modeling during dialysis: application to pediatric hemodialysis," The International Journal of Artificial Organs, vol. 18, No. 3 , (1995), pp. 122-129.

Sugisaki et al., "Phosphate in Dialysis Patients," Trans Am Soc Artif Intern Organs, vol. XXIX, (1983), pp. 38-43.

Sugisaki et al., "Dynamic Behavior of Plasma Phosphate in Chronic Dialysis Patients," Trans Am Soc Artif Intern Organs, vol. XXVIII, (1982) pp. 302-307.

Gotch et al., "A Kinetic Model of Calcium Mass Balance during Dialysis Therapy," Blood Purification, vol. 25, (2007) pp. 139-149.

Gotch et al., "A Kinetic Model of Inorganic Phosphorus Mass Balance in Hemodialysis Therapy," Blood Purification vol. 21, (2003), pp. 51-57.

Toussaint et al., "Review of dialysate calcium concentration in hemodialysis," Hemodialysis International vol. 10, (2006), pp. 326-337.

Palmer, "Individualizing the Dialysate in the Hemodialysis Patient," Seminars in Dialysis, vol. 14, No. 1 (Jan.-Feb. 2001), pp. 41-49.

Ruggeri et al., "New Models of Phosphate Kinetics in Dialysis Patients," Proceedings—19th Conference—IEEE/EMBS, Oct. 30-Nov. 2, 1997—Chicago, IL, pp. 2132-2134.

International Search Report—mailing date Sep. 14, 2011—PCT/US2011/032736, 4 pgs.

Spalding et al., "Phosphate kinetics during hemodialysis: Evidence for biphasic regulation," Kidney International, vol. 6, No. 2, Feb. 2002, pp. 655-667, XP-002639106.

Gotch et al., "A Kinetic Model of Inorganic Phosphorus Mass Balance in Hemodialysis Therapy," vol. 21, No. 1, (2003) pp. 51-57, XP-002639107.

Ratanarat et al., "Phosphate Kinetics during Different Dialysis Modalities," vol. 23, No. 1, (2005) pp. 83-90, XP-002639108.

Leypoldt et al., "Kinetics of β2-Microglobulin and Phosphate during Hemodialysis: Effects of Treatment Frequency and Duration," Seminars in Dialysis, vol. 18, No. 5 (2005), pp. 401-408, XP-002639109.

International Search Report, PCT/US2011/032735, date of mailing Jun. 15, 2011, 4 pages.

Written Opinion of the International Search Authority, PCT/US2011/032735, date of mailing Jun. 15, 2011, 7 pages.

International Preliminary Report on Patentability and Written Opinion of the International Searching Authority for corresponding International Appl. No. PCT/US2011/032736 dated Oct. 16, 2012.

International Preliminary Report on Patentability and Written Opinion of the International Searching Authority for corresponding International Appl. No. PCT/US2011/032735 dated Oct. 16, 2012.

Manns et al., The acu-menTM: A new device for continuous renal replacement therapy in actue renal failure, Kidney International, 1998, pp. 268-74, vol. 54.

Mexican Office Action for Mexican Application No. Mx/a/2012/012061, dated Jun. 26, 2014.

* cited by examiner

FIG. 3

Patient Parameter Estimations (HD Test Data) — 20

<< BACK | RUN >>

Patient Information

| Name | J. Doe |
| Age | 41 |
| Gender | Male |
| Weight | 180 |

Comments: residual function good, active, works daily, prefers shorter, night therapies.

Treatment Setting

| Treatment time (min) | 240 |
| Blood flow rate (ml/min) | 280 |
| Dialysate flow rate (ml/min) | 500 |

HD Test Results

| Time (minutes) | Urea (mg/L) | B2-M (mg/L) | Phosphate (mg/L) |
|---|---|---|---|
| 0 | 280 | 28 | 53 |
| 60 | 196 | 15 | 29 |
| 120 | 186 | 10 | 23 |
| 240 | 180 | 8 | 21 |
| 300 | 188 | 12 | 20 |
| 360 | 192 | 14 | 21 |
| 480 | 200 | 15 | 20 |
|  | 24 | 26 | 28 |

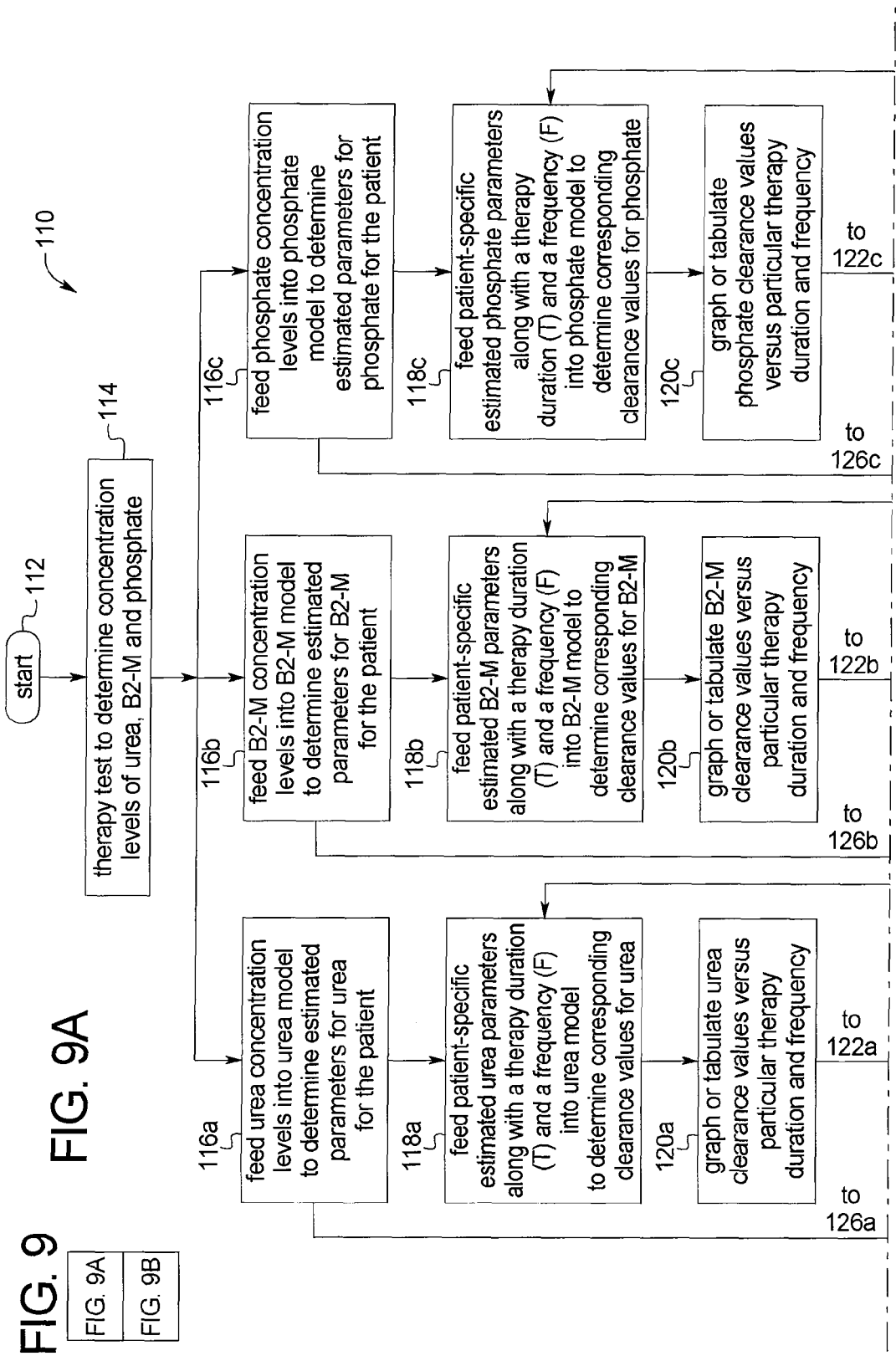

THERAPY PREDICTION AND OPTIMIZATION FOR RENAL FAILURE BLOOD THERAPY, ESPECIALLY HOME HEMODIALYSIS

PRIORITY CLAIM

This application claims priority to and the benefit of U.S. Provisional Patent Application Ser. No. 61/438,002 filed on Jan. 31, 2011, U.S. Provisional Patent Application Ser. No. 61/388,315 filed on Sep. 30, 2010 and U.S. Provisional Patent Application Ser. No. 61/325,113 filed on Apr. 16, 2010, the entire disclosures of each of which are hereby incorporated by reference and relied upon.

BACKGROUND

The present disclosure generally relates to dialysis systems. More specifically, the present disclosure relates to therapy prediction and optimization systems and methods for hemodialysis, especially home hemodialysis ("HHD").

Hemodialysis ("HD") in general uses diffusion to remove waste products from a patient's blood. A diffusive gradient that occurs across the semi-permeable dialysis membrane between the blood and an electrolyte solution called dialysate causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Home hemodialysis ("HHD") has to date had limited acceptance even though the clinical outcomes of this modality are more attractive than conventional hemodialysis. There are benefits to daily hemodialysis treatments versus bi- or tri-weekly visits to a treatment center. In certain instances, a patient receiving more frequent treatments removes more toxins and waste products than a patient receiving less frequent but perhaps longer treatments.

In any of the blood therapy treatments listed above, there is an art that goes along with the science. Different patients will respond differently to the same therapy. In centers where most dialysis takes place, a patient's therapy is honed over time with the aid of staff clinicians or nurses. With home therapy, the patient will visit a clinician's or doctor's office on a regular, e.g., monthly basis, but will not typically have a nurse or clinician at home to help optimize the therapy. For this reason, a mechanism to aid in optimizing a hemodialysis or other blood therapy treatment early on after beginning dialysis is desirable.

Home therapy or HHD also provides the patient with therapy options that the in-center patient does not have. For example, HHD can perform therapy at night if desired, using a single or double needle modality. Any therapy, including a nighttime therapy can be performed over an amount of time that the patient can elect. Because the patient does not have to commute to a center, the patient can perform therapy on days that are convenient for the patient, e.g., weekend days. Similarly, the patient can choose a therapy frequency, or number of therapies per week, that is most convenient and/or most effective. With the added flexibility comes questions, for example, the patient may wonder whether it is better to run six therapies a week at 2.5 hours per therapy or five therapies a week at three hours per therapy. For this additional reason, not only is a way to help optimize a hemodialysis or other blood therapy treatment upfront desirable, it is also desirable to know what will happen when therapy parameters for the optimized therapy are changed.

Optimizing hemodialysis therapies for a hemodialysis patient can also be done by knowing the serum phosphorus levels of the hemodialysis patient during and outside of a hemodialysis treatment session. However, serum phosphorus levels will vary depending on the type of hemodialysis patient and the characteristics of the hemodialysis treatment sessions.

Plasma or serum (the two terms will be used interchangeably) phosphorus kinetics during HD treatments cannot be explained by conventional one or two compartment models. Previous approaches have been limited by assuming that the distribution of phosphorus is confined to classical intracellular and extracellular fluid compartments. More accurate kinetic models able to describe phosphorus kinetics during HD treatments and the post-dialytic rebound period during short HD ("SHD") and conventional HD ("CHD") treatment sessions can be used to predict steady state, pre-dialysis serum phosphorus levels in patients treated with HD therapies. This information can be useful in determining optimal treatment regimens for hemodialysis patients.

SUMMARY

The present disclosure sets forth two primary embodiments, a first primary embodiment, under Roman Numeral I below, the present disclosure sets forth systems and methods for a renal failure blood therapy, such as, hemodialysis, hemofiltration, hemodiafiltration, and in particular for home hemodialysis ("HHD"). The systems and methods of the present disclosure have in one embodiment three primary components, which can be stored on one or more computer, such as the computer for a doctor, clinician or nurse (referred to herein collectively as "doctor" unless otherwise specified). The doctor's computer, can be in data-networked communication with the renal failure therapy machine, e.g., via an internet, a local or a wide area network. Or, the output of the doctor's computer can be stored on a portable memory device such as a universal serial bus ("USB") drive that is taken and inserted into the renal failure therapy machine. The first component is an estimation component. The second component is a prediction component. The third component is an optimization component. The output of the estimation component is used as an input to both the prediction and optimization components. The prediction and optimization components can both be used to determine therapy prescriptions that will yield suitable solute clearances, e.g., for urea, beta 2-microglobulin ("β2-M") and phosphorus or phosphate (the two terms will be used interchangeably). The doctor then consults with the patient to pick one or more chosen prescription that the patient believes best fits the patient's lifestyle.

As shown below, the inputs to the optimization component are the therapy outcomes desired by the doctors. The output of the optimization component is one or more suitable therapy prescription for the patient to be run on a renal blood treatment machine, such as a hemodialysis, hemofiltration, or hemodiafiltration machine. The therapy prescription can set therapy parameters, such as (i) therapy frequency, e.g., number of therapies per week, (ii) therapy duration, e.g., one hour to eight hours, (iii) therapy type, e.g., single needle versus dual needle, (iv) dialysate flowrate and/or overall volume of fresh dialysate used during therapy, (v) blood flowrate, (vi) ultrafiltration rate and/or overall volume of ultrafiltrate removed during therapy, (vii) dialysate composition, e.g., conductivity, and (viii) dialyzer or hemofilter parameters, such as dialyzer clearance capability or flux level.

The initial or estimation component includes a test that is run on the patient while the patient is undergoing the therapy of choice, e.g., hemodialysis, hemofiltration, or hemodiafiltration. The test uses a set of therapy prescription parameters, such as, treatment time, blood flowrate and dialysate flowrate. While the patient is undergoing treatment, blood samples are taken at various times over the treatment, e.g., at half-hour, forty-five minute or hour intervals. The samples are analyzed to determine the level of certain therapy markers, such as urea concentration (small molecule), beta 2-microglobulin ("β2-M") (middle molecule), and phosphate (certain dialysis therapies can remove too much phosphate, so it is desirable to know if the patient may be predisposed to this phenomenon). In general, the concentration of each of the markers will lower over time as the urea, β2-M and phosphate are cleared from the patient's blood.

The concentration or clearance results are then fed into a series of models or algorithms for the estimation component to determine a set of estimated patient parameters for (i) the particular patient, (ii) the particular molecule and (iii) its corresponding algorithm. For example, one of the parameters is G, which is the generation rate for the particular solute or molecule produced as a result of dietary intake, e.g., food and drink. $K_D$, another estimated patient parameter, is dialyzer clearance for the molecule. $K_{IC}$, a further estimated parameter, is the patient's inter-compartmental mass transfer-area coefficient for the molecule or solute. $K_M$, another estimated parameter, is the mobilization clearance of phosphorus determining the rate at which phosphorus is released into the extracellular space. V, yet another parameter that may be estimated, is the distribution volume of phosphorus. Other estimated parameters are discussed below.

The prediction component uses the estimated patient parameters fed into the modules or algorithms from the estimation component or module to calculate clearance results for one or more solute, e.g., urea, β2-M and/or phosphate over a varied set of therapy prescription parameters. The prediction component also uses assumed patient parameters. For example, $K_{NR}$, is the patient's residual kidney coefficient for the molecule or solute (non-renal clearance of the solute is also often included into this term), which can be considered a constant, such that it does not have to be estimated on an individual basis. Shown in detail below are graphs illustrating the output of the prediction component, in which a combination of therapy duration and therapy frequency is graphed along the x-axis and a solute concentration, e.g., urea, β2-M or phosphate is graphed along the y-axis. The graphs provide (i) a visual cue to the average concentration level for the solute and (ii) estimate the maximum concentration level that the solute will reach. The graphs can be used to determine one or more clinically acceptable parameters, such as standard Kt/V of urea and mean pre-treatment plasma concentration ("MPC") of β2-M and pre-dialysis plasma concentration of phosphorus, all of which in turn help identify the appropriate and customized therapy prescription. The doctor can communicate the acceptable prescriptions to the patient, who then picks one or more chosen prescription for downloading to the HHD machine.

The optimization component operates the reverse of the predication component and instead inputs desired solute concentration levels into the models of the estimation component, using the estimated parameters of the estimation component to determine an optimized set of therapy prescription parameters for the patient. The optimization takes into account the doctor's desired solute concentration clearance for the patient for one or more solutes and the patient's preference, e.g., as to therapy frequency and duration. In one example, the optimization component inputs a doctor's requirement for urea, β2-M and phosphate clearances, which yields a plurality of therapy prescriptions that meet the clearance requirements. The doctor and patient can then view the acceptable therapy prescriptions and select one or more chosen prescription for loading into the renal failure blood therapy, e.g., HHD, machine.

Thus, the prediction and optimization components can both lead to chosen therapy prescriptions that are downloaded to the HHD machine. The optimization component may be easier to use to choose a suitable therapy prescription than the prediction components because it is less iterative (for the doctor) than the prediction component. However, the prediction component can provide more detailed information for the doctor and for a particular therapy prescription. Thus, in one particularly useful implementation of the present disclosure, the system estimates, optimizes and allows for choice and then predicts detailed results for the optimized and chosen therapy prescription.

It is contemplated that the patient's estimated patient parameters, e.g., G, $V_D$, $K_{IC}$ and $K_M$ be updated periodically to adjust for a changing condition of the patient and to adjust for actual data obtained from past therapies. For example, the patient can have blood work done periodically, such that the downloaded prescription can be changed if the results of the blood work warrant such a change. Thus, the three components can be cycled or updated periodically, e.g., once or twice a year or as often as the doctor finds necessary.

In the second primary embodiment under Roman Numeral II below, the present disclosure sets forth methods of predicting serum phosphorus concentrations in a patient during hemodialysis. In one embodiment, the method includes measuring serum phosphorus concentrations ("C") of the patient over a hemodialysis treatment session time and an ultrafiltration rate ("$Q_{UF}$") calculated by a difference between pre- and post-dialytic body weight of the patient during an initial hemodialysis treatment session divided by a total treatment time of the treatment session, estimating a phosphorous mobilization clearance ("$K_M$") and a pre-dialysis distribution volume of phosphorus ("$V_{PRE}$") for the patient, and predicting C of the patient at any time during any hemodialysis treatment session with the estimated $K_M$ and $V_{PRE}$ of the patient. C of the patient can be measured every 15 or 30 minutes during the hemodialysis treatment session.

In another embodiment, a computing device for predicting serum phosphorus concentrations in a patient during hemodialysis includes a display device, an input device, a processor, and a memory device that stores a plurality of instructions, which when executed by the processor, cause the processor to operate with the display device and the input device to: (a) receive data relating to C of a hemodialysis patient over a hemodialysis treatment session time and an $Q_{UF}$ calculated by a difference between pre- and post-dialytic body weight of the hemodialysis patient during a hemodialysis treatment session divided by a total treatment time of the treatment session, (b) estimate $K_M$ and $V_{PRE}$ for the patient, and (c) predict C of the patient at any time during hemodialysis. The processor can operate with the display device and the input device to receive data relating to at least one of $K_R$, $K_D$ or a sampling time for collecting the serum phosphorus concentration.

In yet another embodiment, a method of determining steady state, pre-dialysis serum phosphorus levels in a hemodialysis patient includes obtaining a net generation of phosphorus ("G") of the hemodialysis patient, determining steady state, pre-dialysis serum phosphorus levels ("$C_{SS-PRE}$") of the hemodialysis patient, and simulating the effect of at least one of a patient parameter or a treatment parameter on $C_{SS-PRE}$ of the hemodialysis patient.

In an embodiment, a computing device for determining steady state, pre-dialysis serum phosphorus levels in a hemodialysis patient includes a display device, an input device, a processor, and a memory device that stores a plurality of instructions, which when executed by the processor, cause the processor to operate with the display device and the input device to: (a) receive data relating to G from at least a dietary phosphorus intake of a hemodialysis patient or a urea kinetic modeling of the hemodialysis patient, (b) determine $C_{SS-PRE}$ of the patient, and (c) simulate the effect of at least one of a patient parameter or a treatment parameter on the $C_{SS-PRE}$ of the hemodialysis patient. The processor can operate with the display device and the input device to receive data relating to at least one of $K_R$, $K_D$, $K_M$, $V_{PRE}$, $t_{tx}$, F, $C_{PRE}$ about a month before a hemodialysis treatment session or a sampling time for collecting the serum phosphorus concentration. The computing device can display a treatment regimen of the hemodialysis patient so that $C_{SS-PRE}$ is within a desired range.

An advantage of the present disclosure is accordingly to provide improved renal failure blood therapy systems and methods.

Another advantage of the present disclosure is to provide renal failure blood therapy systems and methods having a therapy prediction tool with which clinicians may adjust renal failure blood therapies, e.g., HHD therapies, for specific patients with respect to the key solute clearance measures.

Yet another advantage of the present disclosure is to provide renal failure blood therapy systems and methods that offer clinicians multiple choices to achieve desired target goals.

Still another advantage of the present disclosure is to provide renal failure blood therapy systems and methods that employ a clinically viable and practical test procedure to help characterize the patient's response to a particular renal blood therapy.

A further advantage of the present disclosure is to provide renal failure blood therapy systems and methods that help to reduce the amount of trial and error in optimizing a blood therapy for the patient.

Still a further advantage of the present disclosure is to provide renal failure blood therapy systems and methods that aid the patient in attempting to optimize lifestyle choices for therapy.

Another advantage of the present disclosure is to accurately predict plasma phosphorus levels in a patient during short, conventional daily and nocturnal hemodialysis.

Yet another advantage of the present disclosure is to accurately predict steady state, pre-dialysis plasma phosphorus serum levels in a patient who is maintained by a hemodialysis therapy for a specified time.

Still another advantage of the present disclosure is to develop or modify hemodialysis treatment regimens so that the plasma phosphorus serum levels of a hemodialysis patient are maintained within a desired range.

A further advantage of the present disclosure is provide systems that develop or modify hemodialysis treatment regimens so that the plasma phosphorus serum levels of a hemodialysis patient are maintained within a desired range.

Yet a further advantage of the present disclosure is to conserve dialysate and other dialysis supplies, streamlining the therapy and lowering therapy cost.

Additional features and advantages are described herein, and will be apparent from, the following Detailed Description and the figures.

BRIEF DESCRIPTION OF THE FIGURES

FIG. 3 is an example of a patient parameter estimation input screen of one embodiment of a renal failure blood therapy system and method of the present disclosure.

DETAILED DESCRIPTION

I. Therapy Estimation, Prediction and Optimization

Figure 1:
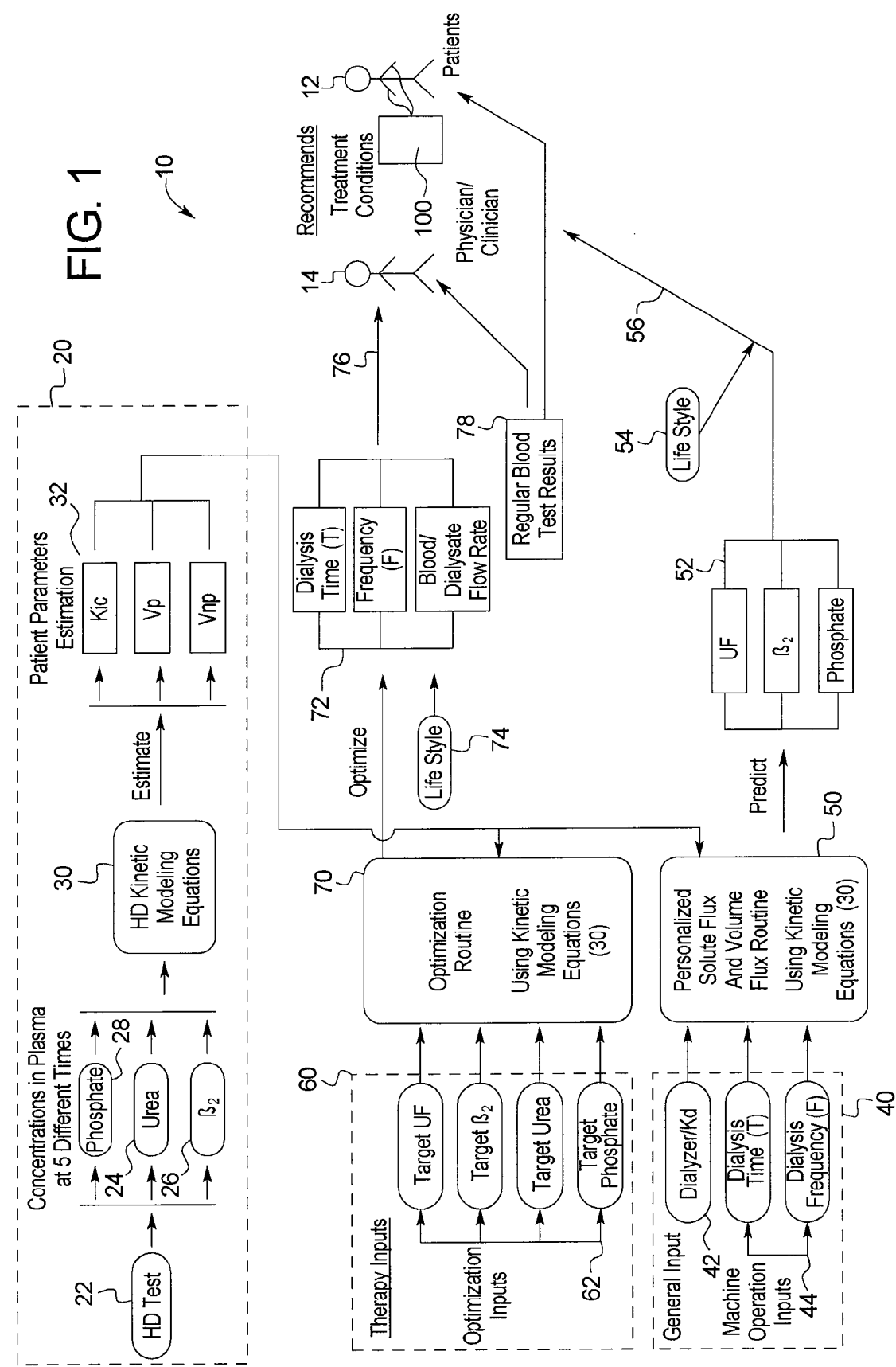
FIG. 1 is a schematic overview of one embodiment of a renal failure blood therapy system and method of the present disclosure.

Referring now to the drawings and in particular to FIG. 1, system 10 illustrates one optimization system and method of the present disclosure for implementing a therapy prescription into a renal failure blood therapy machine 100, such as a hemodialysis machine, and in particular home hemodialysis ("HHD") machine. One particularly well suited HHD machine to operate the systems and methods of the present disclosure is set forth in the following United States patent applications: (i) U.S. Pub. No. 2008/0202591, (ii) U.S. Pub. No. 2008/0208103, (iii) U.S. Pub. No. 2008/0216898, (iv) U.S. Pub. No. 2009/0004033, (v) U.S. Pub. No. 2009/0101549, (vi) U.S. Pub. No. 2009/0105629, U.S. Pub. No. 2009/0107335, and (vii) U.S. Pub. No. 2009/0114582, the contents of each of which are incorporated herein expressly by reference and relied upon. The HHD machine includes at least one processor and at least one memory that are specifically modified or programmed to accept a therapy prescription to run, which is prescribed by a doctor, clinician or nurse (for convenience referred to collectively hereafter as a doctor 14 unless otherwise specified). The therapy is downloaded to the HHD machine (for convenience "HHD machine" refers collectively hereafter to a home hemodialysis, home hemofiltration, home hemodiafiltration or a continuous renal replacement therapy ("CRRT") machine unless otherwise specified), e.g., via a memory storage device, such as a flash drive or universal serial bus ("USB") drive, or via an internet or other local or wide area data network.

A patient 12 may be provided with multiple suitable therapies and be allowed to choose between the therapies, e.g., based upon the patient's schedule that day or week. United States patent applications that disclose the provision of and selection from multiple peritoneal dialysis therapies include: (i) U.S. Pub. No. 2010/0010424, (ii) U.S. Pub. No. 2010/0010423, (iii) U.S. Pub. No. 2010/0010426, (iv) U.S. Pub. No. 20100010427, and (v) U.S. Pub. No. 20100010428, each assigned to the assignee of the present disclosure, and the entire contents of each of which are incorporated herein by reference and relied upon.

System 10 includes three components, namely, an estimation component 20, a prediction component 40 and an optimization component 60.

Estimation Component

Estimation component 20 includes a patient test 22, which involves actually performing the therapy of choice, e.g., a hemodialysis, hemofiltration, hemodiafiltration or CRRT therapy on patient 12 and taking blood samples at different times, e.g., at five different times, during the actual therapy. The test therapy can for example be a four-hour therapy, in which the sample times are, for example, at beginning of the test, ½ hour, one hour and two hours; or the test therapy can for example be an eight-hour therapy, in which the samples are taken at the beginning of therapy, and at one hour, two hours, four hours, five hours, six hours and eight hours. The test therapy durations and number of samples can be varied as desired.

The blood samples are each analyzed to determine the level of concentration of certain marker solutes, such as, urea 24 (small molecule), beta 2-microglobulin ("β2-M") 26 (middle molecule), and phosphate 28. It is known that for certain patients running certain dialysis therapies, e.g., longer therapies, that too much phosphate can be removed from the patient, to the point that in some instances phosphate has to be returned to the patient. System 10 contemplates the determination of whether the patient may be predisposed to experiencing low phosphate levels.

The concentration levels determined at known times during therapy are fed into a series of models or algorithms 30, one model for each solute of concern, e.g., a first model 30a for urea 24, a second model 30b for β2-M 26 and a third model 30c for phosphate 28. Models 30 (referring collectively to models 30a, 30b, 30c, . . . 30n) can each include one or more algorithm. Suitable models 30 are discussed herein.

The output of estimation component 20 includes a multitude of estimated patient parameters 32 for each solute 24, 26, and 28 of concern, which are based on the patient's blood results using models 30 and are therefore specific to the patient. While it is important to the present disclosure that the estimated patient parameters 32 are tailored to the patient's physiologic make-up, the doctor may feel that a blood test is too strenuous or invasive. Thus, system 10 also contemplates the estimating parameters 32 instead using empirical data, e.g., typical parameter values for the patient based on for example age, weight, sex, blood type, typical blood pressure, height, therapy duration, nutritional status, and disease information related to the kinetics of the solute(s) of interest. It is believed that this data can be developed over time using system 10. Important parameters for models 30 of system 10, include estimated patient parameters 32 and known, assumed or calculated (outside of the model) values 42, such as:

$K_{IC}$, which is the patient's inter-compartmental diffusion coefficient for the molecule or solute and is an estimated parameter 32;

$K_D$, which is a known dialyzer clearance for the particular molecule or solute and can be a parameter 42 calculated outside the model;

$K_M$, which is the patient's phosphorus mobilization clearance and is an estimated parameter 32;

$K_{NR}$, which is the patient's residual kidney coefficient for the particular molecule or solute and may be a parameter 42 assumed to be a constant;

V is the distribution volume of phosphorus and is an estimated parameter 32;

G, which is the generation rate for the particular solute or molecule produced by patient's intake and is an estimated parameter 32 or may be an assumed parameter 42;

$V_P$, which is the perfused or extracellular volume, is an estimated parameter 32;

$V_{NP}$, which is the non-perfused or intracellular volume, is an estimated parameter 32;

$V_D$, which is the solute distribution volume in the body, equal to $V_P+V_{NP}$ for urea and beta2-microgulin, is an estimated parameter 32;

$C_P$, which is the extracellular concentration of the solute, is a parameter 42 determined from test 22 and is therefore a known in the models 30 of estimation component 20 (it should be noted that not only can $C_P$ be a measured estimation component 20, Cp can also be predicted along with Cnp by a prediction module, after which one can compare measured and predicted versions of Cp, etc., to gauge the performance of system 10);

$C_{NP}$, which is the intracellular concentration of the solute and cannot be measured, is not a result of test 22 and is not an input to the models, it is instead a predicted output from the prediction and optimization components;

$\Phi_{NP}$, which is a ratio of intracellular compartment volume to the total distribution volume and $\Phi_P$, which is the ratio of extracellular compartment volume to the total distribution volume, both of which are known parameters 42 from literature; and α, which is an interdialytic fluid intake, i.e., water intake, is a parameter 42 calculated outside of models 30 based on average fluid intake, or weight gain.

As shown above, there are at least seven estimated parameters 32, namely, $K_{IC}$, $K_M$, V, G, $V_P$, $V_{NP}$, and $V_D$, where $V_{NP}$ and $V_D$ are related to $V_D$ through $\Phi_P$ and $\Phi_{NP}$. For convenience, only three of them are illustrated in FIG. 1, namely, $K_{IC}$, $V_P$ and $V_{NP}$. It should be appreciated that any one, some or all of the seven parameters can be estimated via estimation component 20 and models 30. It is contemplated to allow desired parameters for estimation to be chosen by the doctor, e.g., via selection boxes like those shown below in FIG. 5 for the solutes under the prediction component 40.

There are also operational parameters 44 discussed herein, such as, blood flowrate, dialysate flowrate, dialysate total volume, ultrafiltration flowrate and ultrafiltration volume, and also operational parameters 44 affecting the patient's life style, such as:

T, which is in one instance the time duration at which each sample is taken in estimation component 20, and is therefore known parameter 42 for the test 22 of estimation component 20, and is in another instance the duration of dialysis in the prediction 40 and optimization 60 components; and F, which is the frequency of therapy, is taken to be one for the single therapy of test 22, but is varied in the prediction 40 and optimization 60 components.

Prediction Component

The estimated patient parameters 32 are then fed back into the models in prediction component 40, particularly into the personalized solute flux and volume flux routine 50. Personalized solute flux and volume flux routine 50 uses in essence the same models or algorithms 30 of component 20, but here using the estimated patient parameters 32 of estimation component 30, as inputs, making the parameters 32 knowns instead of variables.

As shown in FIG. 1, the patient prediction component 40 accepts other known, assumed or calculated (outside of the model) values 42 for the particular solute, such as dialyzer clearance $K_D$, into personalized solute flux and volume flux routine 50. What is left as unknown with routine 50 are (i) variable prescription operational parameters 44, such as dialysis duration ("T") and dialysis frequency ("F") and (iii) solute concentrations 52 (C for both intracellular and extracellular) for solutes 24, 26 and 28. Other machine operating parameters 44 that may be inputted into prediction component 40 and varied include blood flowrate, dialysate flowrate, dialysate total volume, ultrafiltration flowrate and ultrafiltration volume. The solute distribution volume and total body water volume are not constant throughout therapy. System 10 accordingly uses a variable-volume model allowing system 10 to change during the simulated therapy duration. Prediction component 40 then computes $C_P$, $C_{NP}$, $V_P$, and $V_{NP}$ based on the given input variables such F, T, $K_D$, etc. Patient prediction component 40 plugs in different realistic values for operational parameters 44, e.g., as x-axis values of a graph, and outputs solute concentrations 52, e.g., as y-axis values of the graph.

The graphs allow the doctor to view how the concentration 52 of a certain solute varies over the course of, e.g., a week, for a particular set of prescription operational parameters 44. The doctor can see an average value or other accepted measure of quantification for the concentration 52, e.g., a standardized Kt/v for the clearance of urea. The doctor can also see the peak value for the concentration 52 over the course of a therapy cycle.

The doctor can vary therapy duration and frequency input parameters to develop multiple sets of graphs of the outputted solute concentrations, for example, set 1 of graphs for urea, β2-M and phosphate for therapy duration 1 and therapy frequency 1, and set 2 of graphs for urea, β2-M and phosphate for therapy duration 2 and therapy frequency 2. If desired, each set of graphs can be merged onto a single graph, e.g., urea, β2-M and phosphate concentration on one single graph for therapy duration 1 and therapy frequency 1. The therapy duration(s) and frequency(ies) that yield suitable solute concentrations can then be communicated to the patient, who in turn applies life style preferences 54 to yield one or more chosen therapy prescription 56 for downloading to an HHD machine 100. The patient or doctor then selects one of the prescriptions, e.g., on a weekly basis to run for treatment. In other examples, blood and dialysate flowrates may also be adjusted to reach certain clearance goals or to suit the patient's needs.

It is also expressly contemplated to optimize the visual outlay and functionality for the doctor, that is, to optimize the look and operation of the graphs and tables, for example, to only allow values for desired adequacy parameters to be manipulated. System 10 can manipulate these values, so as to be customized to each doctor's needs and preferences. The screens shown herein are accordingly intended to be examples. The examples are not intended to limit the invention.

Optimization Component

Optimization component 60 inputs a plurality of therapy targets 62, such as target removal of urea 24, target removal of β2-M, target removal of phosphate 28, and target removal of ultrafiltration ("UF") or excess water that has built inside the patient between treatments. Therapy targets 62 are entered into an optimization routine 70. In one embodiment, optimization routine 70 uses in essence the kinetic models or equations 30 discussed above for estimation component 20, which like with routine 50, have entered the estimated patient parameters 32 obtained from estimation component 20. Then, calculations for each solute are made in the reverse of prediction component 40. That is, instead of entering prescription operational parameters 44 and calculating solute concentration 52, a desired solute concentration 52 is entered and operational parameters 44, which will satisfy the desired or optimized solute concentration 52 are calculated. Here, the results 72 of optimization component 60 are independent of, or more precisely the reverse of, the results of prediction component 40. Optimization routine 70 identifies one or more therapy prescription 72 that meets the desired or optimized solute concentration 52 for each designated solute.

In particular, the computational techniques using optimization routine 70 of optimization component 60 have been found to be robust and stable procedures that identify the therapy conditions that achieve the aimed input target values (e.g. β2-M pre-dialysis serum concentration ("MPC"), urea standard Kt/v (std Kt/v), and phosphate steady state pre-dialysis serum concentration) by the clinician. The computational techniques identify multiple optimized therapy prescriptions and attempt to do so by performing the least number of iterative simulations. Outputted therapy parameters from optimization component 60 can include therapy duration ("T"), therapy frequency ("F"), blood and dialysate flow rates ("$Q_B$" and "$Q_D$", respectively).

Figure 24:
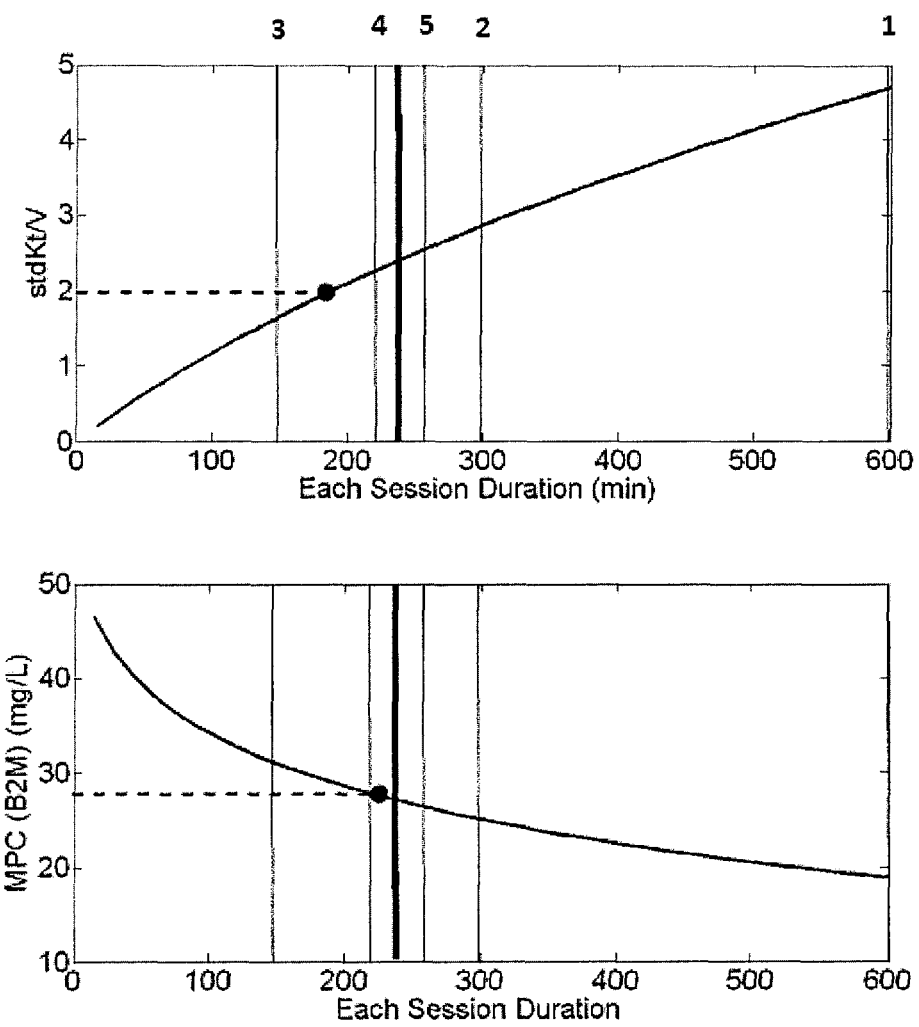
FIG. 24 shows the relationships between urea stdKt/v, β2-M MPC and therapy duration.

In one example, the target (i.e., input) urea stdKt/v and β2-M MPC may be set to be 2.0 and 27.5 mg/L respectively. FIG. 24 shows the relationships (e.g., curves) between urea stdKt/v, β2-M MPC and therapy duration. In the example, the input target values are indicated by dotted lines. Optimization routine 70, following a relatively easy and iterative procedure, varies therapy duration T (for a given set of F, $Q_B$, and $Q_D$) until both urea stdKt/v and β2-M MPC target values are satisfied at the minimum necessary T, which is presumed to be the optimal T for both the patient and the hemodialysis machine because the time the patient is connected to the machine and the time the machine needs to run and consume dialysate components is minimized.

In a first sample iteration, the optimization routine 70 performs a simulation at $T_1$=600 minutes, a therapy duration generally long enough to produce adequacy parameters much better than desired. In a second sample iteration, optimization routine 70 performs a simulation at $T_2$=600/2=300 minutes, producing satisfactory results. In the third step, optimization routine 70 performs a simulation at $T_3$=300/2=150 minutes, this time producing unsatisfactory results for both stdKt/v and β2-M MPC. In a fourth iteration, optimization routine 70 performs a simulation at an increased time $T_4$=(150+300)/2=225 minutes, producing satisfactory result for stdKt/v only. In a fifth iteration, optimization routine 70 performs a simulation at a further increased time $T_5$=(225+300)/2=263 minutes, producing satisfactory results for both stdKt/v and β2-M MPC.

At the end of each step, if both target parameters are achieved, the optimization routine 70 in one embodiment calculates the difference between the target and achieved values. If the difference for at least one of the target parameters is greater than a threshold value, then optimization routine 70 performs yet another iteration to achieve results closer to the target values, further lessening and optimizing duration T. Using the above procedure, optimization routine 70 performs a final simulation at T=(263+225)/2=244 minutes (bold vertical line), where both stdKt/v and β2-M MPC targets are satisfied and the differences between achieved stdKt/v and β2-M MPC and target stdKt/v and β2-M MPC are small.

As illustrated, the optimal therapy duration T of 244 minutes is found in only six iterations, again for a given set of F, $Q_B$ and $Q_D$. Multiple optimized therapy prescriptions can then be identified, e.g., varying therapy duration, frequency, blood and/or dialysate flowrates, to allow the patient a choice based on lifestyle as discussed below.

Patient 12 and doctor 14 review the therapy prescriptions that meet the desired or optimized solute concentration 52 and factor in the patient's life style preferences 74. Perhaps patient 12 prefers a short daily therapy during the day when the patient's spouse is awake for assistance. Or perhaps the patient works out on Monday, Wednesday and Friday and has less UF due to sweat on those days, preferring then to run treatments on other days.

Applying lifestyle preferences 74 to the therapy prescriptions 72 that meet the desired or optimized solute concentration 52 yields a chosen one or more therapy prescription 76. Chosen therapy prescription 56 and 76 can be downloaded to machine 100, e.g., via manual entry into machine 100, a download from a memory storage device, e.g., flash drive or universal serial bus ("USB") drive, or a download from a data network such as an internet.

It is contemplated to modify a chosen one or more therapy prescription 56 or 76 from time to time, e.g., due to regular and periodic blood testing 78, which the patient has performed from time to time. The patient may lose residual renal function over time causing the chosen one or more therapy prescription 56 or 76 to need to be modified. The blood work may in any case indicate that the chosen one or more therapy prescription 56 or 76 is not removing one or more solute effectively enough, prompting a change. The patient may lose weight or undergo a lifestyle change, which allows for a less rigorous one or more therapy prescription 56 or 76 to be used instead. In any case, it is contemplated that lifestyle preferences 74 will continue to play a role in potentially modifying the selected one or more therapy prescription 76.

Sample Screen Shots

FIGS. 2 to 8B are sample screenshots further illustrating system 10 described in connection with FIG. 1. The screen shots of FIGS. 2 to 8B can be custom generated per the request of the doctor and can be implemented on the processing and memory of one or more computer used by the doctor, clinician or nurse, which can be in data networked communication with the HHD machine 100, e.g., via an internet, local or wide area network. It is also contemplated, especially for in-center machines, to implement system 10 and the screen shots of FIGS. 2 to 8B at the one or more processing and memory of machine 100.

Figure 2:
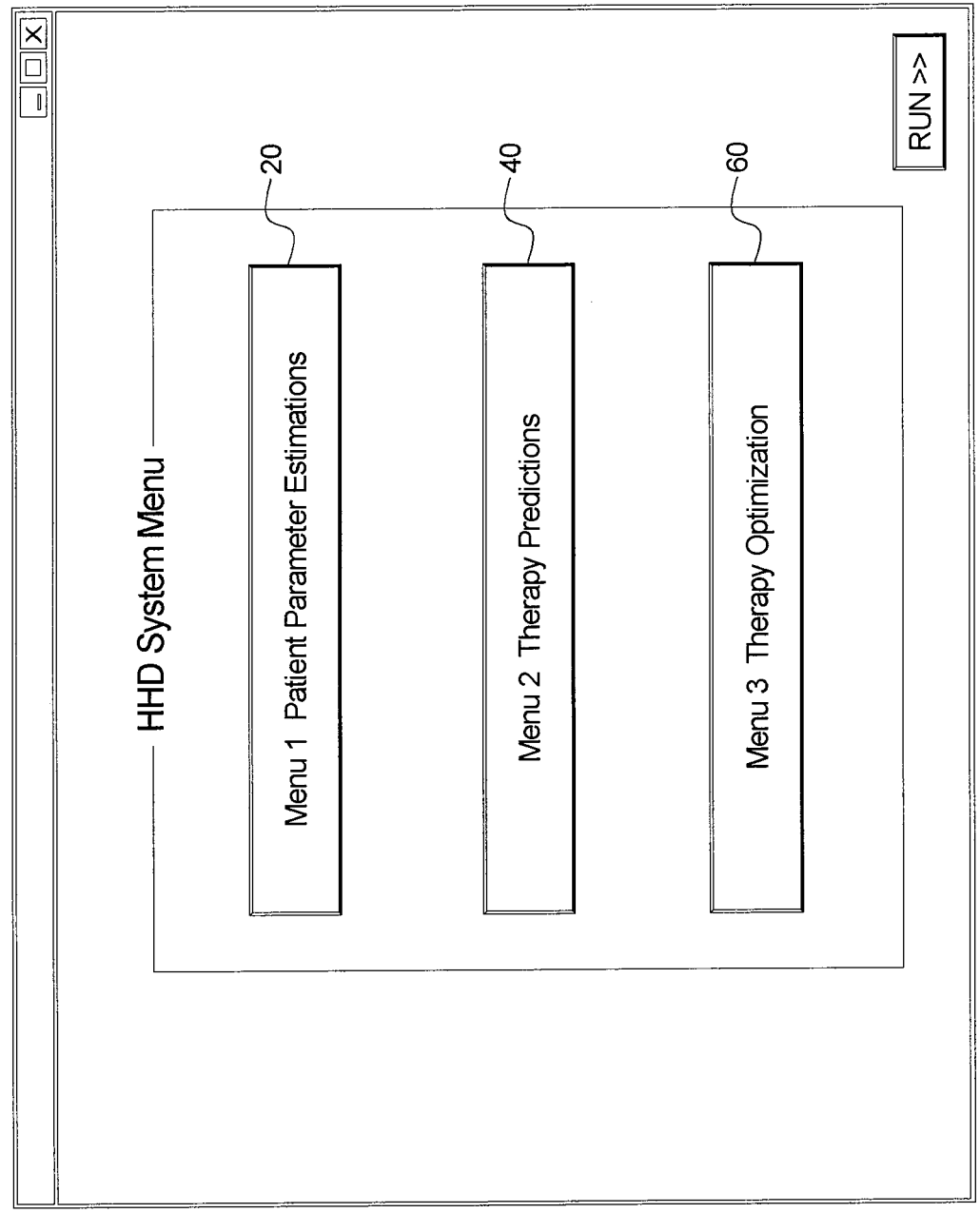
FIG. 2 is an example of a system component selection screen of one embodiment of a renal failure blood therapy system and method of the present disclosure.

FIG. 2 illustrates a sample startup screen that allows the doctor to choose whether to enter or work with the patient parameter estimation component 20, the therapy prediction component 40 or the therapy optimization component 60. System 10 was described above from start to finish. It may be however that patient parameter estimation component 20 has already been performed, such that the doctor can jump directly to either the prediction component 40 or the therapy optimization component 60. As discussed above, therapy optimization component 60 can operate independent of prediction component 40. Thus, it may be that the doctor only uses one of prediction component 40 and optimization component 60 at a particular time or application of system 10.

Prediction component 40 and therapy optimization component 60 rely on information from patient parameter estimation component 20, however, it should be noted that if the patient 12 does not wish to undergo test 22, or the doctor 14 does not want the patient 12 to undergo test 22, it may be possible, although not preferred, to use standardized values based on the patient's information, such as age, sex, blood type, residual renal function if known, etc. It is also expressly contemplated to maintain a database of estimated patient parameters 32 developed over time using system 10, which may provide viable standardized estimated patient parameters 32 based on patient category.

FIG. 3 illustrates a sample data entry and test 22 result screen for parameter estimation component 20. The screen at the left accepts patient information, such as name, age, gender and weight. It is contemplated for system 10 to be able to search for a file under any of this inputted data. The doctor enters data for test 22 into the middle of the screen of FIG. 3, such as total treatment time, blood flowrate, dialysate flowrate (or total volume) and UF rate or volume (not illustrated). The patient then undergoes a test therapy that is run according to this inputted data. The screen of FIG. 3 at the right then accepts the results of the blood testing done for urea 24, β2-M 26 and phosphate 28 at various times over the course of the treatment, forming a time-based profile for each of the analyzed solutes. The sample times show in FIG. 3 include a starting time, and one hour, two hours, four hours, five hours, six hours and eight hours from the starting time. Other intervals including more or less time entries can be used alternatively.

Figure 4:
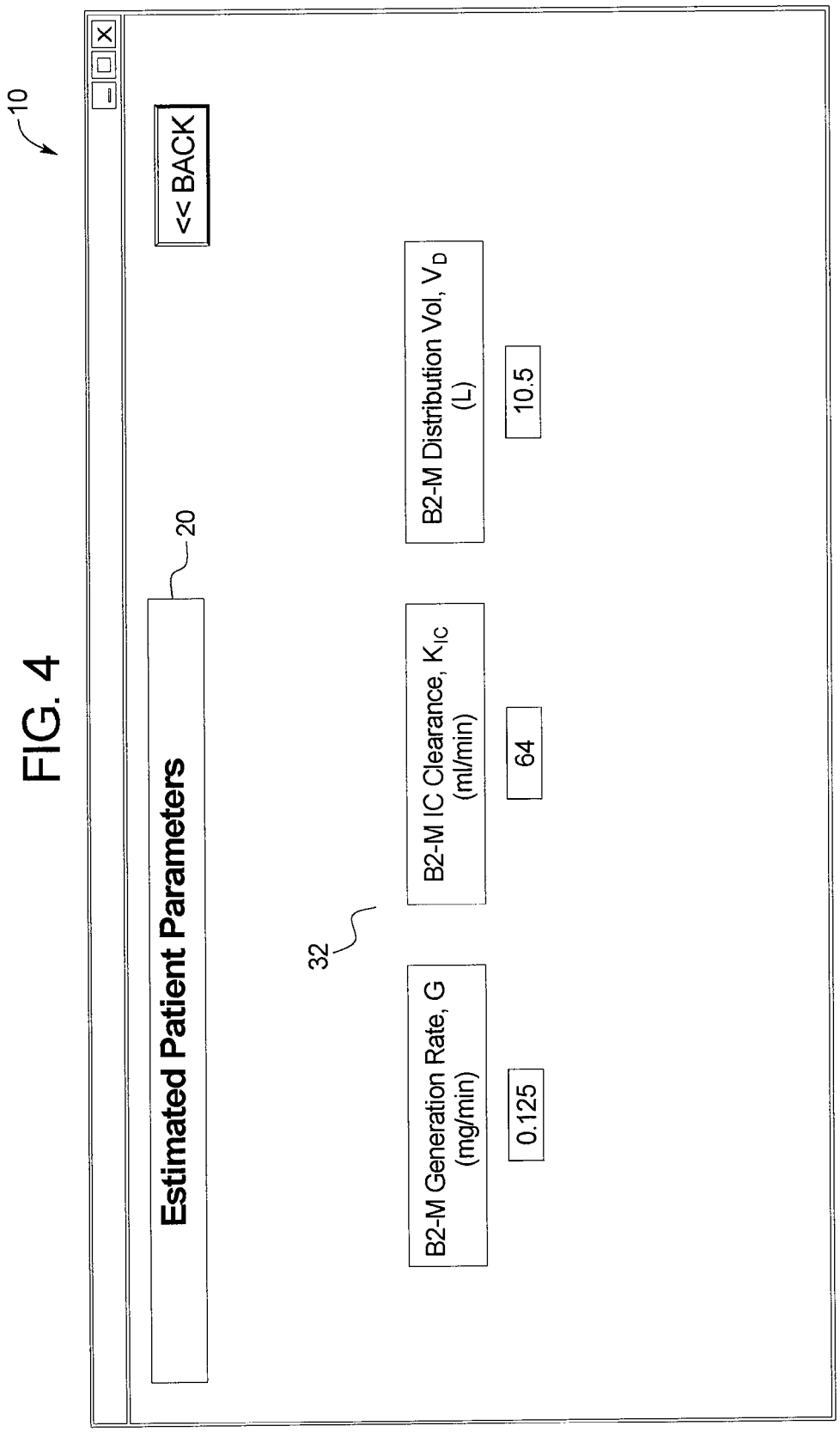
FIG. 4 is an example of a patient parameter estimation output screen of one embodiment of a renal failure blood therapy system and method of the present disclosure.

FIG. 4 illustrates a sample estimated patient parameters 32 display screen. Estimated patient parameters 32 can include, for example, generation rate G, intracellular clearance $K_{IC}$, phosphorus mobilization clearance $K_M$, and distribution volume $V_D$, ($V_D = V_P + V_{NP}$, where $V_P$ is the perfused or extracellular volume, and $V_{NP}$ is the non-perfused or intracellular volume). The values for G, $K_{IC}$, and $V_D$, are the outputs of models 30 of estimation components 20, and are then used as inputted data in components 40 and 60 as estimated patient parameters 32.

Figure 5:
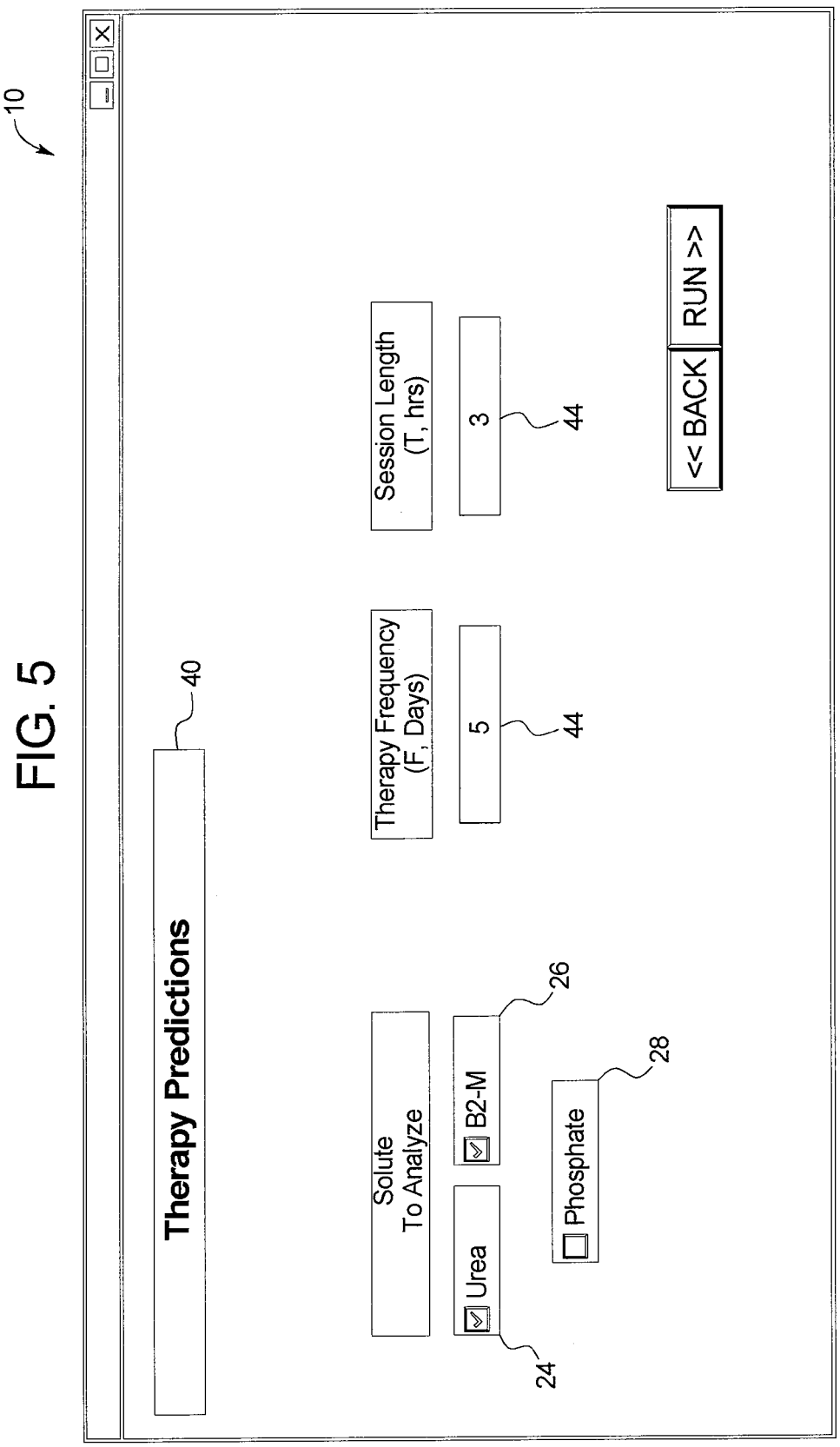
FIG. 5 is an example of a therapy prediction input screen of one embodiment of a renal failure blood therapy system and method of the present disclosure.

FIG. 5 illustrates a sample input screen for prediction component 40. In the illustrated example, the doctor at the left of the screen chooses to run the prediction routine for urea 24 and β2-M (boxes checked), but not for phosphate 28 (boxes not checked). The doctor also enters operational inputs 44, namely, the doctor wishes to model a therapy that is run five days a week (i.e., F) for three hours (i.e., T) per session. As discussed above, other machine operating parameters that may be entered (and varied) alternatively or additionally to F and T include blood flowrate, dialysate flowrate, dialysate total volume, ultrafiltration flowrate and ultrafiltration total volume. "Back" and "Run" buttons allow the doctor to navigate through each of the components 20, 40 or 60 when the particular component are selected.

Figure 6:
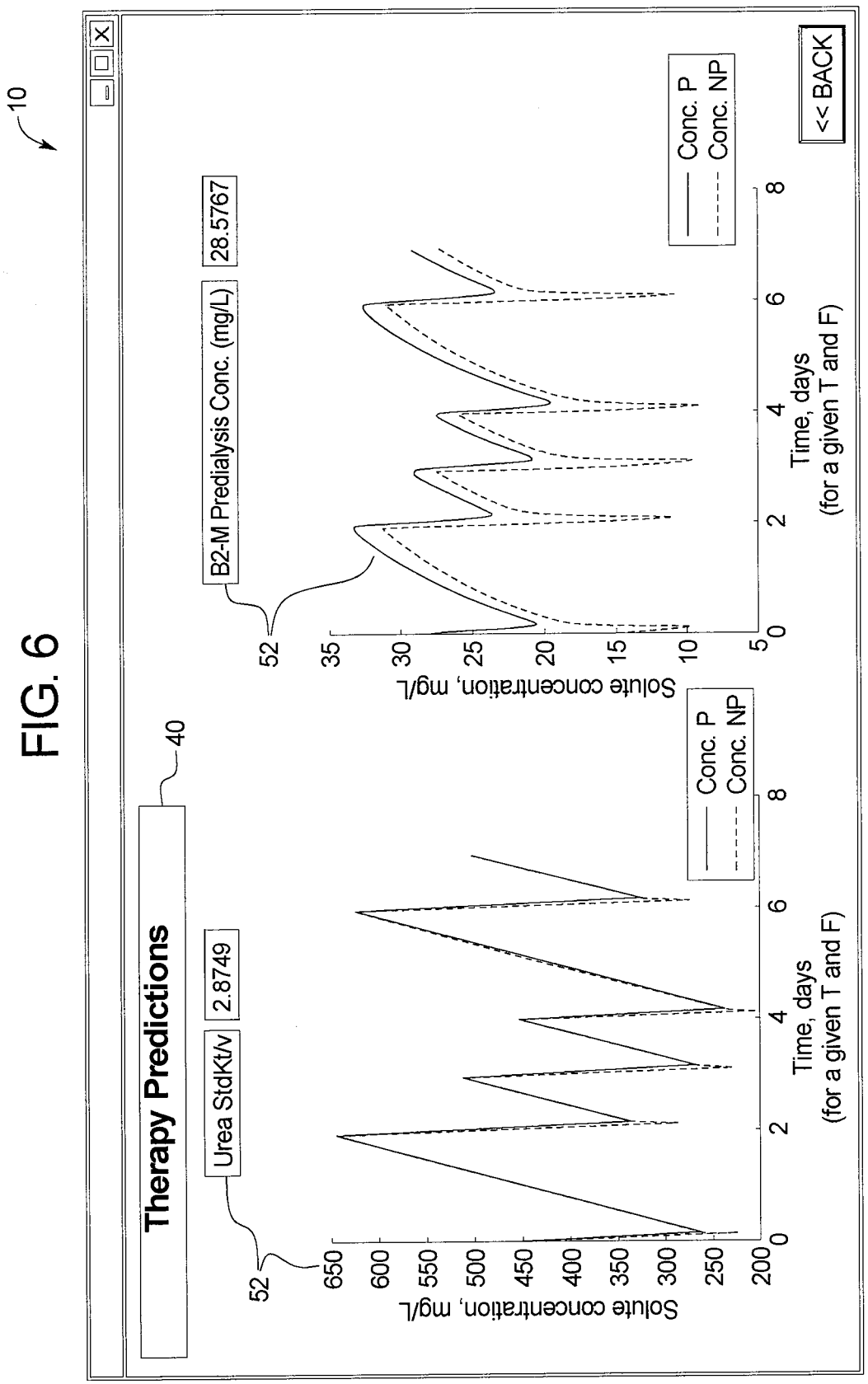
FIG. 6 is an example of a therapy prediction output screen of one embodiment of a renal failure blood therapy system and method of the present disclosure.

FIG. 6 illustrates a sample output screen for prediction component 40, which shows the results after running the personalized solute flux and volume equations 50. If desired, the concentration results can be merged onto a single graph, for example, with the urea concentration scale along the left and β2-M scale along the right. Solute concentrations 52 could alternatively be displayed in spreadsheet form but are shown in FIG. 6 in graphical form, with days from a start of using the particular therapy prescription along the x-axis. This way, the doctor can readily see the predicted solute profile for a given frequency and duration, and for the patient's personalized estimated parameters. Solute concentrations 52 are also shown in an average or standardized form, e.g., as a standard Kt/v, which is understood by those of skill in the art. Knowing peak concentration and the average or standardized concentration, the doctor can quickly determine if the proposed frequency and duration are adequate for the selected solutes, here, urea 24 and β2-M 26. As delineated in FIG. 6, P is for perfused or extracellular, NP is for non-perfused or intracellular. If the solute, for example urea, is in the extracellular or blood volume then the dialyzer can readily clear the solute. If the solute is in the intracellular volume, then the solute has to first pass in to the extracellular volume overcoming the resistance defined by $K_{IC}$.

FIG. 6 illustrates concentration values for a particular therapy duration T and frequency F. It is contemplated for the doctor to re-run prediction component 40 to vary T and F. The doctor can then choose one or more sets of graphs, e.g., from (i) $T_1$, $F_1$; (ii) $T_2$, $F_2$; (iii) $T_3$, $F_3$; etc., that are clinically acceptable. The acceptable graphs or their corresponding therapy prescriptions can then be reviewed with the patient, who selects one or more graph or prescription that best meets the patient's lifestyle needs and/or requirements.

Figure 7:
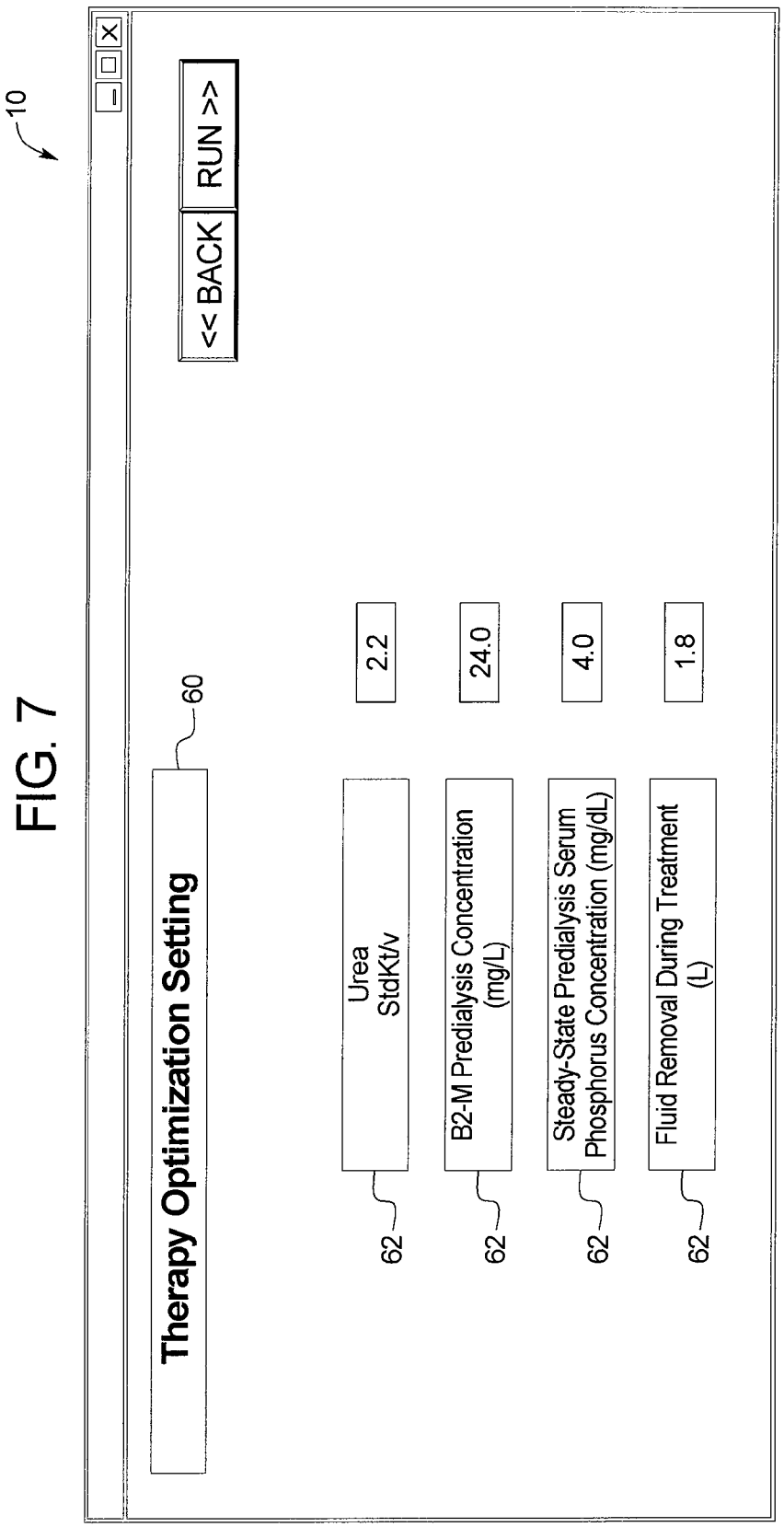
FIG. 7 is an example of a therapy optimization input screen of one embodiment of a renal failure blood therapy system and method of the present disclosure.

FIG. 7 illustrates a sample input screen for optimization component 60. Running opposite to prediction component 40, the doctor in optimization component 60 enters desired values for therapy results, e.g., a desired value for urea, e.g., via standard Kt/v, a desired value for phosphorus in, e.g., pre-dialysis phosphorus plasma concentration in milligrams per liter, a desired value for β2-M in, e.g., milligrams per liter, and a desired ultrafiltrate ("UF") removal value, e.g., in liters. UF is generally a machine-controlled function but can affect solute removal, so the input of UF is desirable for optimization.

Figure 8A:
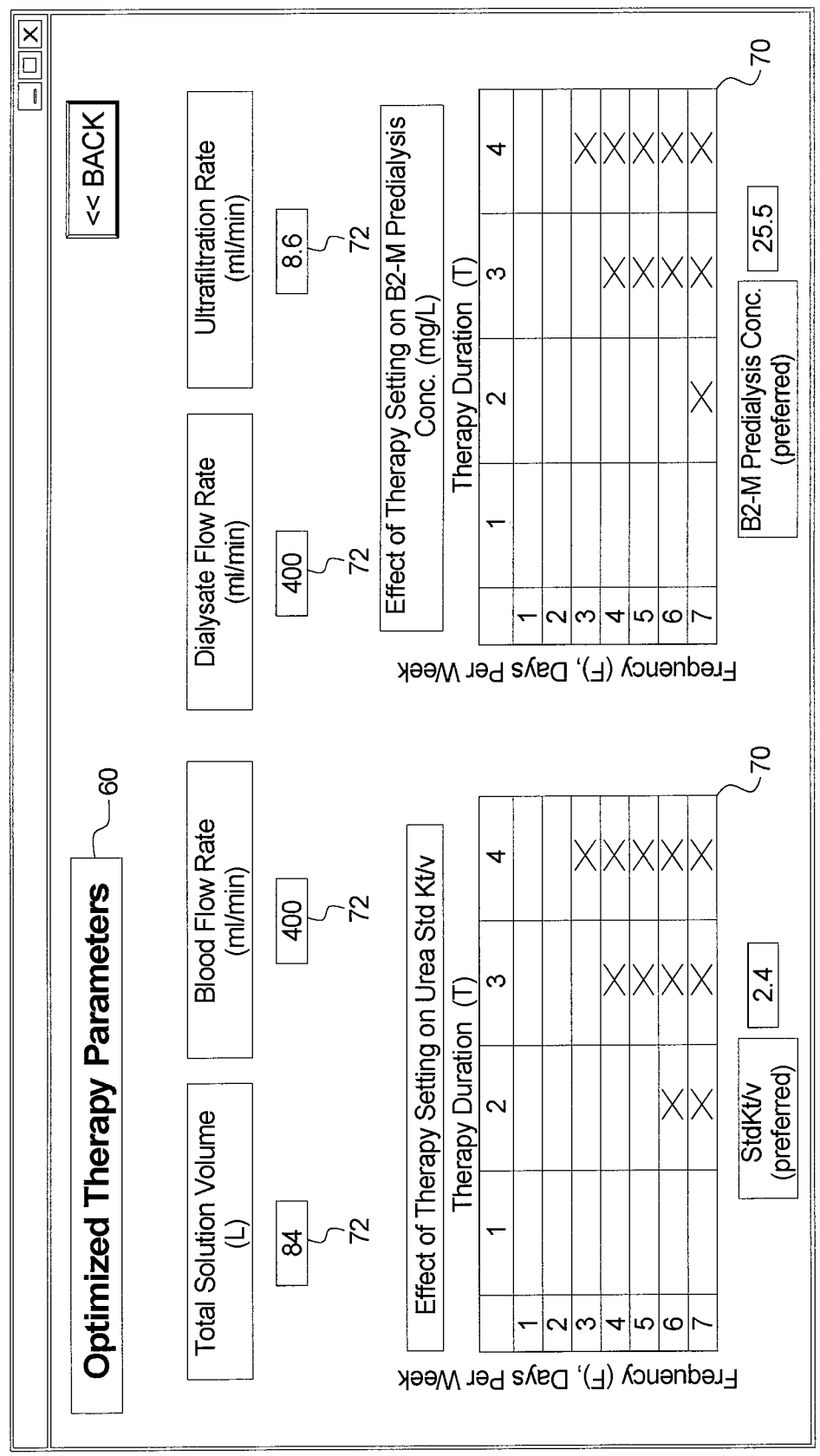
FIG. 8A is an example of a therapy optimization routine screen of one embodiment of a renal failure blood therapy system and method of the present disclosure.

FIG. 8A shows an example of an optimization routine 70, which for inputted urea and β2-M (and phosphate if desired) requirements, shows a spreadsheet of frequency in Days Per Week (along the side) and Therapy Duration in hours (along the top), and places an "X" in the cell corresponding to a treatment that will meet the requirement for that solute. In the twelve possible combinations shown in FIG. 8, two (four days of three hour treatments and vice versa) meet the requirements for urea and β2-M requirements. The patient can then decide which option fits his/her lifestyle better. Or, both prescriptions can be machine entered or chosen prescriptions 72. The patient then decides, for example on a weekly basis, which of the two approved and chosen prescriptions is a better fit for that week.

FIG. 8A also shows example inputted parameters 72 for optimization component 60, here, resulting blood flowrate, total solution volume, dialysate flowrate (or total volume) and UF rate (or volume), which are used in the equations for all of the frequency combinations in the urea and β2-M optimization routines 70. The doctor, independent of system 10, may calculate blood flowrate and dialysate flowrate, etc., to achieve desired $K_D$ values. However, those calculations are independent of the calculations taking place as part of the prediction 40 and/or optimization 60 components. For system 10, flowrates are inputs to determine $K_D$, which in turn is an input to the prediction and/or optimization components 40 and 60.

Figure 8B:
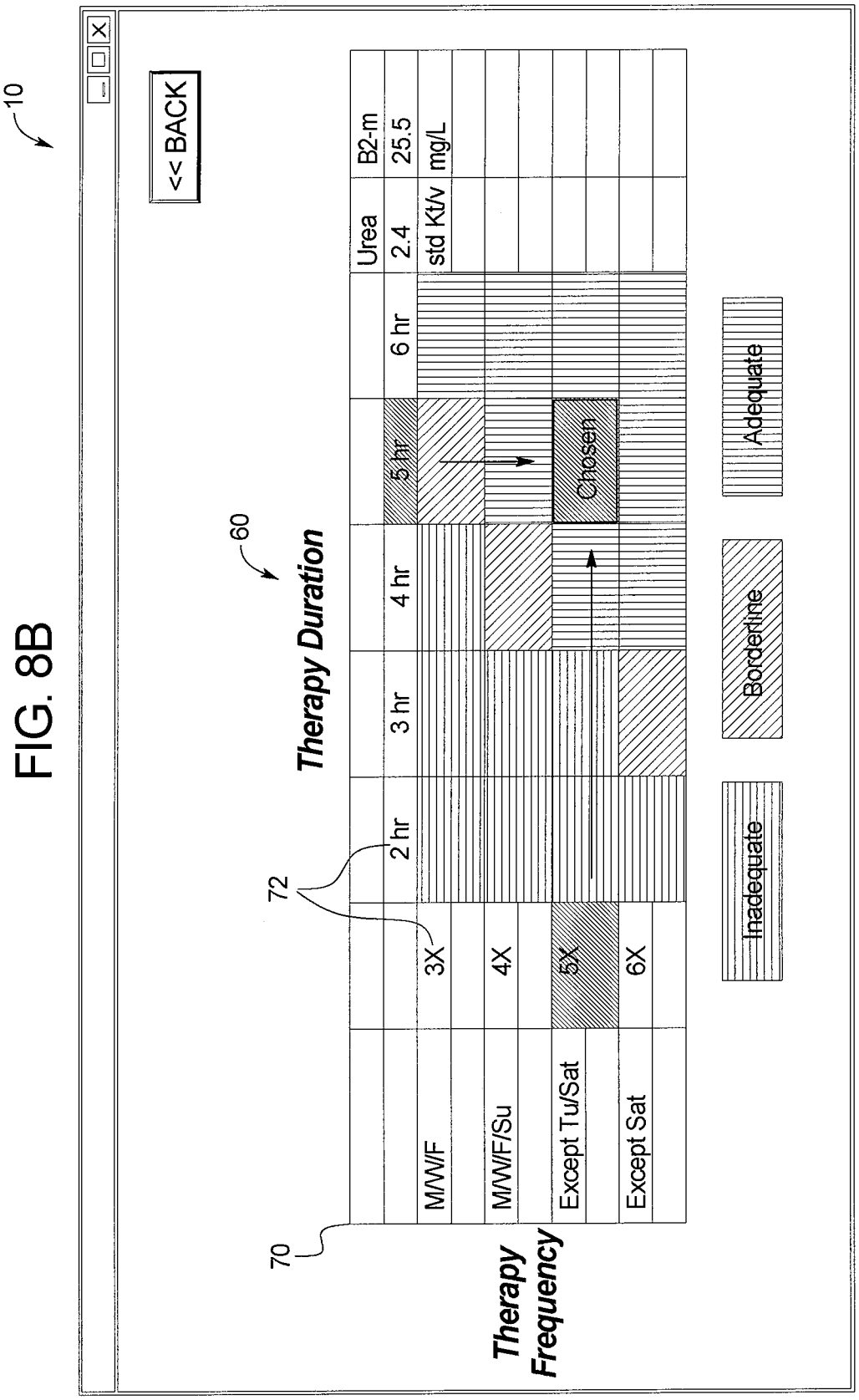
FIG. 8B is another example of a therapy optimization routine screen of one embodiment of a renal failure blood therapy system and method of the present disclosure.

FIG. 8B shows another example of an optimization routine 70, which for inputted urea and β2-M (and phosphate if desired) requirements, shows a spreadsheet of Therapy Frequency (i.e., F) in days of the week (along side) and Therapy Duration (i.e., T) in hours (along top). Here, the actual days of the week are shown. Optimization component 60 can discern between different combinations of the same number of days, e.g., three days Monday/Wednesday/Friday versus three days Monday/Wednesday/Saturday. In one embodiment, system 10 assumes certain preset days when therapy frequency values are entered. For instance, for an F of three days per week, system 10 would assume, e.g., Monday/Wednesday/Friday. System 10, however, allows doctor 14 to enter specific days (as opposed to entering F). System 10 makes the calculations according to the days entered. The ability of simulating custom therapy days can be important because system 10 can then more accurately track the accumulation of solutes within the body.

In FIG. 8B, each cell is then color coded or otherwise designated into one of three categories (for example) for the clearance of not just a particular solute, but for the analyzed solutes as a group. The desired standardized Kt/v values for urea located at the upper right of the chart of routine 70 show the group of solute cleaners. Each cell of solute clearances is labeled in the example as inadequate, borderline or adequate. For example, adequate can mean meets all requirements, borderline can mean meets some requirements or almost meets all requirements, while inadequate means misses most or all requirements. More or less than three classifications having different meanings can be used alternatively. The patient can then choose from one of the adequate therapy prescription cells, for example, choose the least rigorous therapy prescription.

Figure 9B:
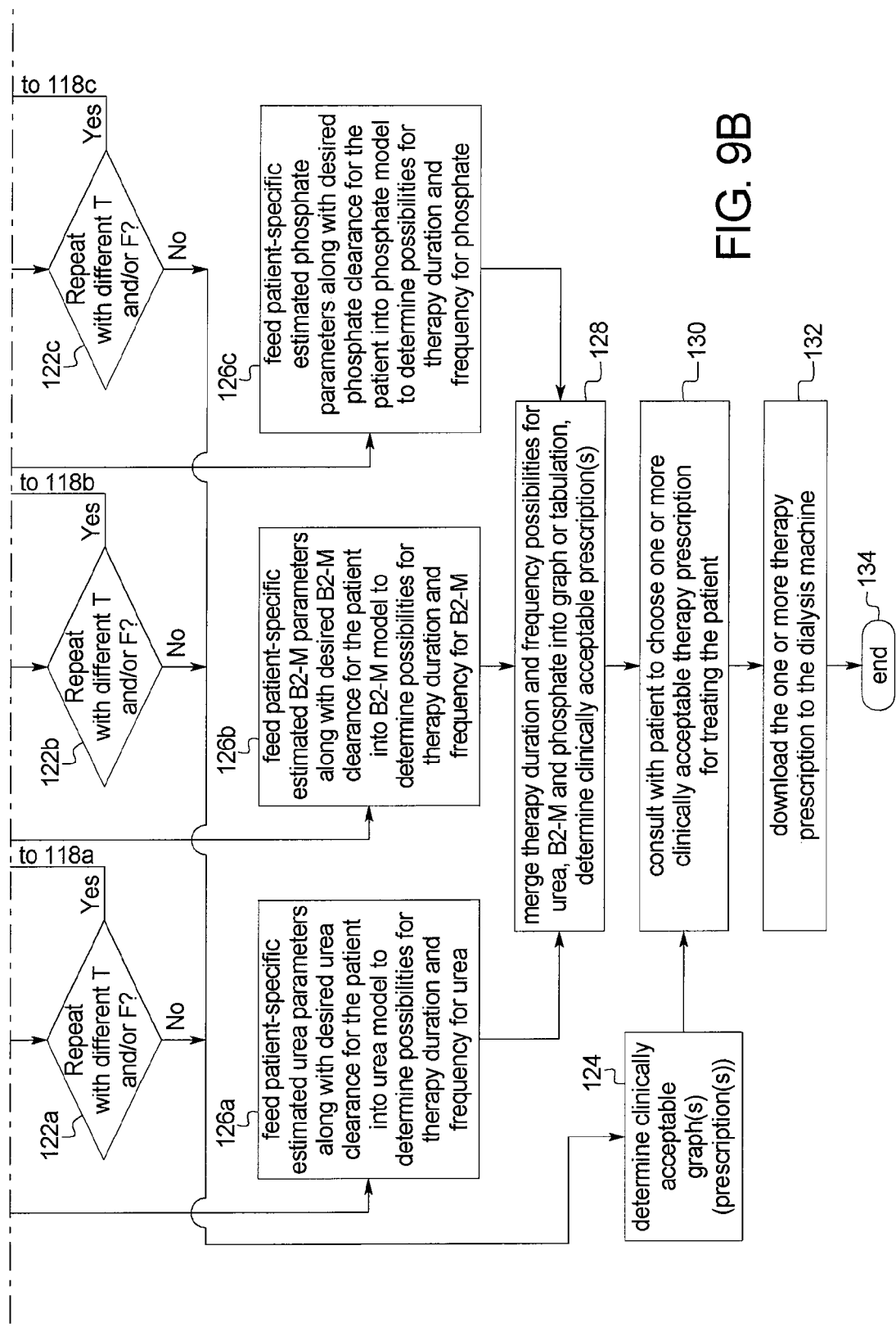
FIG. 9 is a schematic flow diagram summarizing some of the features for the renal failure blood therapy system and method of the present disclosure.

Referring now to FIG. 9, method 110 illustrates the relationship between components 20, 40 and 60 of system 10 discussed herein. Method 110 is meant to help understand the interrelationship between components 20, 40 and 60 and is in no way meant to describe all the alternatives for the components, which have been described in detail above.

At oval 112, method 110 begins. At block 114, the test therapy is performed on the patient to determine concentration levels for various solutes, such as urea, β2-M and phosphate. The solutes for system 10 and method 110 are not limited to those three solutes and could include others, such as calcium, parathyroid hormone ("PTH"), and certain protein-bound solutes such as p-cresol sulfate. It is expressly contemplated to include these and other solutes in system 10 and method 110. The additional solutes can at least be tracked via the testing in estimation component 20 for example as they relate to general adequacy and/or to correlate with phosphate clearance/mobilization. The additional solutes can eventually be predicted via prediction component 40 and optimized via component 60 when models are devised in the future for the additional solutes, as has been done below for phosphate.

At blocks 116a, 116b, and 116c, the concentration levels for urea, β2-M and phosphate are fed into the corresponding kinetic model to determine at least one patient-specific parameter. All of the test concentrations of the solute, less than all of the test concentrations of the solute, or some averaged test concentration for the solute may be entered into the corresponding kinetic model.

At blocks 118a, 118b, and 188c, the at least one patient-specific estimated parameter is fed along with at least one machine operational parameter, such as therapy duration (i.e., T) and therapy frequency (i.e., F), into the corresponding kinetic model for urea, β2-M and phosphate to determine clearance volumes or solution levels for the solute.

At blocks 120a, 120b, and 120c, the solute clearance values for urea, β2-M and phosphate are graphed (could be single combined graph) or tabulated for the doctor's evaluation. At diamonds 122a, 122b and 122c, it is determined whether blocks 118a to 118c and 120a to 120c are repeated for another set of inputted operational therapy parameters. If not, at block 124 the doctor determines which graph(s), tabulation(s), prescription(s) are clinically acceptable.

At blocks 126a to 126c, the patient-specific estimated parameters for urea, β2-M and phosphate are fed into the corresponding kinetic model along with a desired solute removal level or level for the solute to determine one or more machine operational parameter that will satisfy the equation and achieve the desired level for the one or more solute.

At block 128, the machine operating parameters that achieve the desired solute level (or some of the desired solute levels) are tabulated for the doctor. The doctor can then hone in on the best clinically acceptable therapies for the patient.

At block 130, which is fed from both the predicting block 124 and the optimization block 128, the doctor consults with the patient to determine which one or more chosen therapy prescription best suits the patient's personal needs. As discussed above, machine operational parameters include T, F and others, such as fluid flowrates and/or volumes. These other parameters are likely to be mandated by the doctor and not be as negotiable with the patient. To a certain degree, T and F will drive the other parameters. For example, a shorter therapy will likely require higher flowrates.

At block 132, the chosen one or more therapy prescription is downloaded to the patient's (or clinic's) renal failure therapy machine (e.g., HHD machine 100). If multiple chosen prescriptions are downloaded, the patient may be empowered to choose, e.g., weekly, which prescription to run. Alternatively, the doctor may dictate, at least initially, which prescription to run. The prescription download may be via a data network or data storage device such as USB or flash drive.

It should be appreciated that system 10 in alternative embodiments can incorporate any of the methods, models and equations discussed below and in detail in section II.

Kinetic Modeling (i) Urea and β2-M Modeling

Suitable kinetic models 30 for urea and β2-M for system 10 are shown below and described in detail in by: Ward (Ward et al., *Kidney International*, 69: 1431 to 1437 (2006)), the entire contents of which are incorporated expressly herein by reference and relied upon, for a two compartment model, $$\frac{d(V_p C_p)}{dt} = \Phi_p G + K_{ic}(C_{np} - C_p) -$$
$$\Theta K_d C_p - K_{nr} C_p + \Theta \Phi_{np} Q_{uf} C_{np} - (1 - \Theta) \Phi_{np} \alpha C_p$$
$$\frac{d(V_{np} C_{np})}{dt} = \Phi_{np} G + K_{ic}(C_p - C_{np}) - \Theta \Phi_{np} Q_{uf} C_{np} + (1 - \Theta) \Phi_{np} \alpha C_p$$

and Clark (Clark et al., *J. AM Soc. Nephrol.*, 10: 601-609 (1999)), the entire contents of which are incorporated expressly herein by reference and relied upon, $$\frac{d(V_p C_p)}{dt} = G + K_{ic}(C_{np} - C_p) - \Theta K_d C_p - K_{nr} C_p$$
$$\frac{d(V_{np} C_{np})}{dt} = K_{ic}(C_p - C_{np})$$
$$\frac{d(V_p)}{dt} = -\Theta \Phi_p Q_{uf} + (1 - \Theta) \Phi_p \alpha$$
$$\frac{d(V_{np})}{dt} = -\Theta \Phi_{np} Q_{uf} + (1 - \Theta) \Phi_{np} \alpha$$

The above equations are applicable to both urea and β2-M. The same model is used for both solutes, with the parameter values being different, such as, generation rate, non-renal clearance, distribution volume, etc.

(ii) Mass Balance Modeling

One suitable model for electrolyte balance for system 10, e.g., for sodium, potassium, etc., is a three compartment model, and is described in detail by Ursino et al., (Ursino M. et al., Prediction of Solute Kinetics, Acid-Base Status, and Blood Volume Changes During Profiled Hemodialysis, *Annals of Biomedical Engineering*, Vol. 28, pp. 204-216 (2000)), the entire contents of which are incorporated expressly herein by reference and relied upon.

(iii) Modeling Modifications for Replacement Fluid

As described herein, system 10 is not limited to dialysis and can be applied to other renal failure blood treatments such as hemofiltration and hemodiafiltration. Hemofiltration and hemodiafiltration both involve the use of a replacement fluid, which is pumped directly into the blood lines for convective clearance used in place of (hemofiltration) or in addition to (hemodiafiltration) the osmotic clearance of dialysis.

The equations below show modifications to the kinetic models that Applicants have found can be made to all for use of replacement fluid. The first equation below shows the effect on mass balance. In particular, the factor $Q_R * C_{s,R}$ is added for replacement fluid. The second equation below shows the effect of convective clearance ($J_s(t)$) on dialyzer clearance.

$$\frac{dM_{s,ex}(t)}{dt} = -\Phi_s(t) - J(t) + R_{s,ex}(t) + Q_R \cdot c_{s,R}$$

$$J_s(t) = S_s \cdot Q_F(t) \cdot \frac{c_{s,p}(t)}{r}$$

II. Phosphate Modeling

Phosphate Prediction Methods in Hemodialysis Patients and Applications Thereof

In light of the systems discussed herein, it is contemplated to provide methods of predicting serum or plasma phosphorus concentrations or levels in a hemodialysis patient before, during and after hemodialysis therapies. Being able to predict serum phosphorus levels can be useful in determining optimal treatment regimens for hemodialysis patients. These methods can be incorporated into any of the systems and computing devices described herein to optimize hemodialysis therapies for the patient.

Elevated levels of serum phosphorus in end stage renal disease patients have been associated with greater risk of mortality, primarily due to cardiac-related causes. Such associations have been demonstrated among various countries throughout the world and over time. Although the physiological mechanisms involved remain incompletely understood, inadequate control of serum phosphorus levels and the use of calcium-based phosphate binders have been linked to rapid progression of coronary calcification, increased stiffness of the arterial wall and high blood pressure.

Control of serum phosphorus concentrations in most hemodialysis ("HD") patients requires both the daily use of oral phosphate binders to inhibit intestinal absorption of phosphate and the removal of phosphate by HD treatments. Despite this dual approach, hyperphosphatemia often occurs because typical western diets contain high phosphate content. Calcium-based oral phosphate binders are still used extensively because of their low cost, and more effective binders are under active development. Other efforts have attempted to increase dialytic removal of phosphorus during thrice-weekly therapy by various methods, often without substantial improvements. The only HD prescription parameter that has been shown to consistently reduce serum phosphorus concentrations is the use of longer treatments, both during thrice-weekly HD and during HD treatments applied more frequently.

Methods of predicting or determining serum phosphorus levels of a patient undergoing hemodialysis using a robust and practical phosphorus kinetic model allow for effectively modifying new HD treatment modalities on an individual patient basis. In an embodiment, a method of predicting serum phosphorus concentration in a patient during hemodialysis is provided. The method includes measuring serum phosphorus concentrations ("C") of the patient over a hemodialysis treatment session time (using any suitable methods of measuring such as, e.g., fluorometric and colorimetric assays) and an ultrafiltration or fluid removal rate ("$Q_{UF}$") calculated by a difference between pre- and post-dialytic body weight of the patient during an initial hemodialysis treatment session divided by the total treatment time of the treatment session and estimating $K_M$ and $V_{PRE}$ for the patient using a non-linear least squares fitting to the governing transport equations having analytical solutions of the following form:

$$C(t) = C_{PRE} \left[ \frac{K_M + (K_D + K_R - Q_{UF}) \left( \frac{V(t)}{V_{PRE}} \right)^{\frac{K_M + K_D + K_R - Q_{UF}}{Q_{UF}}}}{K_M + K_D + K_R - Q_{UF}} \right] \quad (A)$$

and $$C(T) = C_{PRE} - (C_{PRE} - C_{POST})e^{\left(-\frac{K_M T}{V_{PRE} - Q_{UF} t_{tx}}\right)} \quad (B)$$

wherein t is a time during the hemodialysis treatment session, T is a time after an end of the hemodialysis treatment session, $t_{tx}$ is a total duration of the hemodialysis treatment session, $C_{PRE}$ is a pre-dialysis plasma phosphorus concentration, $C_{POST}$ is a post-dialytic plasma phosphorus concentration, $K_M$ is a phosphorous mobilization clearance of the patient, $K_R$ is a residual renal clearance of phosphate, $K_D$ is a dialyzer phosphate clearance, $V_{PRE}$ is a pre-dialysis distribution volume of phosphorus of the patient, and $$V(t) = V_{PRE} - Q_{UF} \times t \quad (C).$$

C (i.e., serum phosphorus concentrations) of the patient can then be predicted at any time during any hemodialysis treatment session by using the equations A and B, for the previously estimated set of $K_M$ and $V_{PRE}$ of the patient. Alternative to the non-linear least squares fitting, $V_{PRE}$ can also be estimated as a certain percentage of body weight or body water volume of the patient.

In another embodiment, a method of predicting serum phosphorus concentration in a patient during hemodialysis is provided when the ultrafiltration rate is assumed to be negligible (i.e., $Q_{UF}$=0). The method includes measuring C of the patient during an initial hemodialysis treatment session (using any suitable methods of measuring such as, e.g., fluorometric and colorimetric assays) and estimating $K_M$ and $V_{PRE}$ for the patient using a non-linear least squares fitting to the governing transport equations having analytical solutions of the following form:

$$C(t) = C_{PRE} \left[ \frac{K_M + (K_D + K_R)e^{-t\frac{(K_M + K_D + K_R)}{V_{PRE}}}}{K_M + K_D + K_R} \right] \quad (D)$$

and $$C(T) = C_{PRE} - (C_{PRE} - C_{POST})e^{\left(-\frac{K_M T}{V_{PRE}}\right)} \quad (E)$$

C of the patient can be predicted at any time during any hemodialysis treatment session by using the equations D and E for a given set of previously estimated parameters, $K_M$ and $V_{PRE}$, of the patient. Alternatively, $V_{PRE}$ can be further estimated as a certain percentage of body weight or body water volume of the patient. In an embodiment, $K_M$ may be estimated using data from a case where $Q_{UF} \neq 0$ and used in equation D where $Q_{UF} = 0$.

In any of the methods of predicting serum phosphorus concentrations in a patient during hemodialysis described herein, $K_D$ can be determined using the equation:

$$K_D = Q_B \frac{(0.94 - Hct \times 100)(e^Z - 1)}{\left(e^Z - \frac{(0.94 - Hct \times 100)Q_B}{Q_D}\right)} \quad (F)$$

wherein $$Z = K_O A \frac{(Q_D - (0.94 - Hct \times 100)Q_B)}{((0.94 - Hct \times 100)Q_B \times Q_D)}, \quad (G)$$

$$K_O A = \frac{(0.94 - Hct \times 100)Q_{B,M} \times Q_{D,M}}{Q_{D,M} - (0.94 - Hct \times 100)Q_{B,M}} \times \ln\left(\frac{1 - K_{D,M}/Q_{D,M}}{1 - K_{D,M}/[(0.94 - Hct \times 100)Q_{B,M}]}\right), \quad (H)$$

$Q_B$ and $Q_D$ are the blood and dialysate flow rates at which the desired dialyzer clearance $K_D$ is calculated using equations F and G. $K_O A$ is a dialyzer mass transfer area coefficient for phosphate obtained as a result of a previous measurement where the set of blood and dialysate flow rates $Q_{B,M}$ and $Q_{D,M}$ resulted in dialyzer clearance $K_{D,M}$, and Hct is hematocrit count measured from patient's blood sample. Alternatively, $K_D$ can be determined at any time t using the equation:

$$K_D = \frac{C_D(t_s)Q_D(t_s)}{C(t_s)} \quad (I)$$

wherein $t_s$ is a sampling time and $C_D(t_s)$ is a concentration of phosphorus in a dialysate outflow at time $t_s$, $Q_D(t_s)$ is a dialysate flowrate at time $t_s$, and $C(t_s)$ is a serum phosphorus concentration at time $t_s$.

Alternative to non-linear least squares fitting, $K_M$ can be determined using the following algebraic equation:

$$K_M = C_{POST}\left(\frac{K_D - Q_{UF}}{C_{PRE} - C_{POST}}\right). \quad (J)$$

C of the patient can be measured at any suitable time during the hemodialysis treatment session, for example, such as every 15 or 30 minutes. $t_{tx}$ can be any suitable amount of time such as, for example, 2, 4 or 8 hours. T can be any suitable time, for example, such as 30 minutes or 1 hour.

$V_{POST}$ is a measure of the distribution volume of phosphorus at the end of the hemodialysis treatment when the patient is considered to be normohydrated. This parameter approximates the volume of extracellular fluids. Thus, $V_{POST}$ is a clinically relevant patient parameter that can be used to evaluate the patient's hydration status. In an application from knowing the previously determined $V_{PRE}$, $V_{POST}$ can be determined using the equation:

$$V_{POST} = V_{PRE} - Q_{UF} \times t_{tx} \quad (K)$$

and a suitable therapy can be provided to the patient based on the value of $V_{POST}$. As seen from equation K, if $Q_{UF} = 0$, then $V_{POST} = V_{PRE}$.

Specific steps of the methods of predicting phosphorus mobilization in a patient during hemodialysis can be performed using a computing device. Such a computing device can include a display device, an input device, a processor, and a memory device that stores a plurality of instructions, which when executed by the processor, cause the processor to operate with the display device and the input device to (a) receive data relating to C of a hemodialysis patient over a hemodialysis treatment session time and a $Q_{UF}$ calculated based on a difference between pre- and post-dialytic body weight of the hemodialysis patient during a hemodialysis treatment session divided by the total treatment time of the treatment session; (b) estimating $K_M$ and $V_{PRE}$ for the patient using a non-linear least squares fitting to the governing transport equations having analytical solutions of the following form:

$$C(t) = C_{PRE}\left[\frac{K_M + (K_D + K_R - Q_{UF})\left(\frac{V(t)}{V_{PRE}}\right)^{\frac{K_M + K_D + K_R - Q_{UF}}{Q_{UF}}}}{K_M + K_D + K_R - Q_{UF}}\right] \quad (L)$$

and $$C(T) = C_{PRE} - (C_{PRE} - C_{POST})e^{\left(-\frac{K_M T}{V_{PRE} - Q_{UF} t_{tx}}\right)}; \quad (M)$$

and (c) predict C of the patient at any time during hemodialysis by using the equations L and M for a given set of estimated parameters, $K_M$ and $V_{PRE}$, of the patient. It should be appreciated that the variables for equations L and M can be determined using any of the equations set forth herein. The information/data obtained for the hemodialysis patient can be displayed/printed out and used by the healthcare provider to provide improved treatment and nutritional regimens for the hemodialysis patient. Any of the unknown factors can be determined using the appropriate equations or measurements discussed previously for the methods of determining phosphorus mobilization in a patient during hemodialysis.

If $Q_{UF} = 0$, then  $\quad (N)$ $$C(t) = C_{PRE}\left[\frac{K_M + (K_D + K_R)e^{-t\frac{(K_M + K_D + K_R)}{V_{PRE}}}}{K_M + K_D + K_R}\right].$$

The computing device can also be preprogrammed or run according to software that causes the processor to operate with the display device and the input device to receive data relating to at least one of $K_R$, $K_D$ or a sampling time for collecting the serum phosphorus concentration. In an embodiment, the computing device can be system 10 described in section I.

Along with the previously described methods of determining phosphorus mobilization in a patient during hemodialysis, a mass balance model to predict steady state, pre-dialysis serum phosphorus levels ("$C_{SS-PRE}$") in patients treated with HD therapies has also been developed. A mass balance model was used in combination with a pseudo one-compartment model for intradialytic and rebound periods to determine steady state pre-dialysis serum phosphorus levels in individual patients. Using this model, the effect of specific therapy parameters (e.g., dialyzer phosphate clearances, weekly therapy frequency, therapy duration, etc.) on individual hemodialysis patients' serum phosphorus levels can be evaluated.

The disclosed steady state, mass balance model combines the intradialytic phosphorus kinetics with dietary intake, use of phosphate binders, and residual renal clearance to predict steady state, pre-dialysis serum phosphorus levels. Unlike those with previous models, the predictions with this model involve simplified calculations; hence, this model can easily be integrated in daily clinical practice. Furthermore, the model involves patient-specific parameters enabling individualized predictions. This model can eventually be used to optimize therapies with a HHD device to remove adequate amounts of phosphorus using minimum necessary volumes of dialysate (i.e., minimized water consumption). Alternatively, the model can be used to determine the amount of required phosphate salt supplements in dialysate.

In an application of the kinetic model, a method of determining the $C_{SS-PRE}$ in a hemodialysis patient is provided. The method includes obtaining a net generation of phosphorus ("G") from at least a dietary phosphorus intake of the patient or a urea kinetic modeling of the patient and determining $C_{SS-PRE}$ of the hemodialysis patient using the equation:

$$C_{SS-PRE} = \frac{(G)(10080/F)}{(K_D + K_R)n\overline{C}_{tx}t_{tx} + K_R n\overline{C}_i(10080/F - t_{tx})} \quad (O)$$

wherein F is a frequency of treatments per week, $t_{tx}$ is a treatment time for one hemodialysis treatment session (e.g., in units of minutes per treatment session), $K_D$ is a dialyzer phosphate clearance, $K_R$ is a residual renal clearance of phosphate, $n\overline{C}_{tx}$ is the normalized time averaged plasma phosphorus concentration during a dialysis treatment, and $n\overline{C}_i$ is the normalized time averaged plasma phosphorus concentration for an interdialytic interval. The effect of at least one of a patient parameter or a treatment parameter on $C_{SS-PRE}$ of the patient can be simulated so as to obtain an optimal range of $C_{SS-PRE}$ for the patient. For example, the patient parameter can be G, $K_M$ or $V_{PRE}$, and the treatment parameter can be $t_{tx}$, $K_D$ (e.g., $Q_B$, $Q_D$) or F.

In an alternative embodiment, a method of predicting the $C_{SS-PRE}$ in a hemodialysis patient is provided. The method includes determining a net generation of phosphorus ("G") using the equation:

$$G = C_{SS-PRE-IN} \times \left[ \frac{(K_D + K_R)n\overline{C}_{tx}t_{tx} + K_R n\overline{C}_i(10080/F - t_{tx})}{10080/F} \right] \quad (P)$$

wherein $C_{SS-PRE-IN}$ is an initial, measured, steady state, pre-dialysis serum phosphorus level of the hemodialysis patient who is maintained by a hemodialysis therapy (e.g., identified by $K_D$, F and $t_{tx}$) for a specified time prior to the calculation of G using equation P. The specified time can be, for example, at least one week, two weeks, three weeks, 1 month, 2 months, 3 months, 4 months or more prior to the time when G is calculated. F is a frequency of treatments per week, $t_{tx}$ is a treatment time for one hemodialysis treatment session (e.g., in units of minutes per treatment session), $K_D$ is a dialyzer phosphate clearance, $K_R$ is a residual renal clearance of phosphate, $n\overline{C}_{tx}$ is the normalized time averaged plasma phosphorus concentration during a dialysis treatment, and $n\overline{C}_i$ is the normalized time averaged plasma phosphorus concentration for an interdialytic interval.

Once G has been calculated using equation P or estimated by other methods, it can be used in predicting the effect of changes in hemodialysis treatment parameters on the steady state serum phosphorus concentration. For example, once G of the hemodialysis patient is known, $C_{SS-PRE}$ of the patient under different hemodialysis treatment conditions can be predicted by rearranging equation P to form equation O and utilizing the known G to solve for $C_{SS-PRE}$ of the hemodialysis patient. The effect of at least one of a patient parameter or a treatment parameter on $C_{SS-PRE}$ of the patient can be simulated, and a treatment regimen of the hemodialysis patient can then be modified so that $C_{SS-PRE}$ is within a desired range.

In general, there is an optimal range of steady state, pre-dialysis serum phosphorus levels in patients with end stage renal disease. Optimal prescription/regimen/nutritional therapies resulting in steady state, pre-dialysis phosphorus levels within the desired optimal ranges can be determined using equations O and P, for example, in the Optimization Component of the HHD system previously described herein. Because changes in the hemodialysis prescription or in patient behavior (e.g., changes in diet) could lead to changes in G, optimization of home hemodialysis therapies based on equations O and P to maintain $C_{SS-PRE}$ within a desired range is advantageous.

In any of the methods of determining the G or the $C_{SS-PRE}$ in a hemodialysis patient, $n\overline{C}_{tx}$ and $n\overline{C}_i$ can be determined using the equations:

$$n\overline{C}_{tx} = \frac{1}{t_{tx}} \left\{ \frac{\left[\frac{K_M t_{tx}}{K_M + K_R + K_D - Q_{UF}}\right] + \left[1 - \frac{K_M}{K_M + K_R + K_D - Q_{UF}}\right]}{\left[\frac{V_{PRE}}{K_M + K_R + K_D}\right]\left[1 - \left(\frac{V_{POST}}{V_{PRE}}\right)^{(K_M + K_R + K_D)/Q_{UF}}\right]} \right\} \quad (Q)$$

and, $$n\overline{C}_i = \frac{1}{10080/F - t_{tx}} \left\{ \begin{array}{l} \left[\frac{K_M(10080/F - t_{tx})}{K_M + K_R + Q_{WG}}\right] + \\ \left[\frac{K_M}{K_M + K_R + K_D + Q_{UF}} + \right. \\ \left. \left[1 - \frac{K_M}{K_M + K_R + K_D - Q_{UF}}\right]\right] \\ \left[\frac{V_{POST}}{V_{PRE}}\right]^{(K_M + K_D + K_R - Q_{UF})/Q_{UF}} - \\ \frac{K_M}{K_M + K_R + Q_{WG}} \\ \left[\frac{V_{POST}}{K_M + K_R}\right] \\ \left[1 - \left(\frac{V_{POST}}{V_{PRE}}\right)^{(K_M + K_R)/-Q_{WG}}\right] \end{array} \right\} \times, \quad (R)$$

wherein $K_M$ is a phosphorus mobilization clearance of the patient, $Q_{WG}$ is a constant rate of fluid gain by the patient during the interdialytic time interval (calculated by $Q_{WG} = (t_{tx}Q_{UF})/(10080/F)$), $Q_{UF}$ is a constant rate of fluid removed from the patient, $V_{PRE}$ is a pre-dialysis distribution volume of phosphorus of the patient prior to a hemodialysis treatment session, and $V_{POST}$ is a post-dialysis distribution volume of phosphorus of the patient at the end of a hemodialysis treatment session.

In any of the methods of determining G or $C_{SS-PRE}$ in a hemodialysis patient when there is negligible net ultrafiltration or fluid removal from the patient during hemodialysis therapies and no weight gain between hemodialysis therapies, $n\overline{C}_{tx}$ and $n\overline{C}_i$ can be determined using the equations:

$$n\overline{C}_{tx} = \frac{1}{t_{tx}} \left\{ \frac{\left[\frac{K_M t_{tx}}{K_M + K_R + K_D}\right] + \left[1 - \frac{K_M}{K_M + K_R + K_D}\right]}{\left[\frac{V_{PRE}}{K_M + K_R + K_D}\right]\left[1 - \exp(K_D + K_R + K_M)/V_{PRE})\right]} \right\} \quad (S)$$

and,

-continued $$n\overline{C}_i = \tag{T}$$

$$\frac{1}{10080/F - t_{tx}} \left\{ \begin{array}{l} \left[\frac{K_M(10080/F - t_{tx})}{K_M + K_R}\right] + \\ \left[\begin{array}{l} \frac{K_M}{K_M + K_R + K_D} + \\ \left[1 - \frac{K_M}{K_M + K_R + K_D}\right] \times \\ \exp[-(K_D + K_R + K_M)t_{tx}/V_{PRE}] - \\ \frac{K_M}{K_M + K_R} \end{array}\right] \times \\ \left[\frac{V_{POST}}{K_M + K_R}\right] \\ [1 - \exp(-(K_R + K_M)(10080/F - t_{tx})/V_{POST})] \end{array} \right\},$$

It should be appreciated that the variables for equations S and T can be determined using any of the equations set forth herein.

In any of the methods of determining the G or the $C_{SS\text{-}PRE}$ in a hemodialysis patient, $K_D$ can be determined using the equation:

$$K_D = Q_B \frac{(0.94 - Hct \times 100)(e^Z - 1)}{\left(e^Z - \frac{(0.94 - Hct \times 100)Q_B}{Q_D}\right)} \tag{U}$$

wherein $$Z = K_O A \frac{(Q_D - (0.94 - Hct \times 100)Q_B)}{((0.94 - Hct \times 100)Q_B \times Q_D)}, \tag{V}$$

$$K_O A = \frac{(0.94 - Hct \times 100)Q_{B,M} \times Q_{D,M}}{Q_{D,M} - (0.94 - Hct \times 100)Q_{B,M}} \times \tag{W}$$
$$\ln\left(\frac{1 - K_{D,M}/Q_{D,M}}{1 - K_{D,M}/[(0.94 - Hct \times 100)Q_{B,M}]}\right),$$

$Q_B$ and $Q_D$ are the blood and dialysate flow rates at which the desired dialyzer clearance $K_D$ is calculated using equations U and V. $K_OA$ is a dialyzer mass transfer area coefficient for phosphate obtained as a result of a previous measurement where the set of blood and dialysate flow rates $Q_{B,M}$ and $Q_{D,M}$ resulted in dialyzer clearance $K_{D,M}$, and Hct is hematocrit count measured from patient's blood sample. Alternatively, $K_D$ can be determined at any time t using the equation:

$$K_D = \frac{C_D(t_s)Q_D(t_s)}{C(t_s)} \tag{X}$$

wherein $t_s$ is a sampling time and $C_D(t_s)$ is a concentration of phosphorus in a dialysate outflow at time $t_s$ and $Q_D(t_s)$ is a dialysate flowrate at time $t_s$ and $C(t_s)$ is a serum phosphorus concentration at time $t_s$.

Alternative to non-linear least squares fitting, $K_M$ can be determined using the following algebraic equation:

$$K_M = C_{POST}\left(\frac{K_D - Q_{UF}}{C_{PRE} - C_{POST}}\right) \tag{Y}$$

wherein $C_{POST}$ is a post-dialytic plasma phosphorus concentration, and $C_{PRE}$ is a pre-dialysis plasma phosphorus concentration. G can be determined using the equation:

$$G = \frac{I_P A_P - I_B P_B}{10080} \tag{Z}$$

wherein $I_P$ is a weekly dietary intake of phosphorus of the hemodialysis patient, $A_P$ is a percent phosphorus absorption of the hemodialysis patient, $I_B$ is a weekly binder intake of the hemodialysis patient, and $P_B$ is a binding power of the binder.

In an embodiment, $K_M$ and $V_{PRE}$ can be determined using the methods of predicting phosphorus mobilization in a patient during hemodialysis as previously discussed. In this case, $K_M$ and $V_{PRE}$ are determined by measuring C of the hemodialysis patient over a hemodialysis treatment session time and $Q_{UF}$ calculated by a difference between pre- and post-dialytic body weight of the patient during an initial hemodialysis treatment session divided by the total treatment time of the treatment session, and estimating $K_M$ and $V_{PRE}$ for the hemodialysis patient using a non-linear least squares fitting to the governing transport equations having analytical solutions as follows:

$$C(t) = C_{PRE}\left[\frac{K_M + (K_D + K_R - Q_{UF})\left(\frac{V(t)}{V_{PRE}}\right)^{\frac{K_M+K_D+K_R-Q_{UF}}{Q_{UF}}}}{K_M + K_D + K_R - Q_{UF}}\right] \tag{AA}$$

and $$C(T) = C_{PRE} - (C_{PRE} - C_{POST})e^{\left(-\frac{K_M T}{V_{PRE} - Q_{UF} t_{tx}}\right)} \tag{BB}$$

wherein t is a time during the hemodialysis treatment session, T is a time after an end of the hemodialysis treatment session, $t_{tx}$ is a total duration of the hemodialysis treatment session, $C_{PRE}$ is a pre-dialysis plasma phosphorus concentration, $C_{POST}$ is a post-dialytic plasma phosphorus concentration, $K_M$ is a phosphorus mobilization clearance of the patient, $K_R$ is a residual renal clearance of phosphate, $K_D$ is a dialyzer phosphate clearance, $V_{PRE}$ is a pre-dialysis distribution volume of phosphorus of the patient, and $$V(t) = V_{PRE} - Q_{UF} \times t \tag{CC}$$

The methods of determining G or $C_{SS\text{-}PRE}$ in a hemodialysis patient can also be used to determine or modify the appropriate treatments/dietary changes to meet a desired phosphorus serum level in the hemodialysis patient over a period of time. For example, the methods can be used to determine or modify a level of phosphorus intake so that $C_{SS\text{-}PRE}$ of the hemodialysis patient ranges between about 3.6 mg/dl and 5.0 mg/dl. The methods can be used to determine or modify a phosphorus binder administered to the patient so that $C_{SS\text{-}PRE}$ of the hemodialysis patient ranges between about 3.6 mg/dl and 5.0 mg/dl. The methods can further be used to determine or modify an amount of phosphorus salt supplements added to the dialysate so that $C_{SS\text{-}PRE}$ of the hemodialysis patient ranges between about 3.6 mg/dl and 5.0 mg/dl.

The methods can be used to determine or modify the total hemodialysis treatment session time so that $C_{SS\text{-}PRE}$ of the hemodialysis patient ranges between about 3.6 mg/dl and 5.0 mg/dl. The methods can be used to determine or modify the frequency F so that $C_{SS\text{-}PRE}$ of the hemodialysis patient ranges between about 3.6 mg/dl and 5.0 mg/dl. The methods can be used to determine or modify a required blood flowrate and/or a dialysate flowrate so that $C_{SS\text{-}PRE}$ of the hemodialysis patient ranges between about 3.6 mg/dl and 5.0 mg/dl. It should be appreciated that the preferred range of $C_{SS\text{-}PRE}$ can be patient specific.

Specific steps of determining $C_{SS\text{-}PRE}$ of a hemodialysis patient can be performed using a computing device. Such a computing device can include a display device, an input device, a processor, and a memory device that stores a plurality of instructions, which when executed by the processor, cause the processor to operate with the display device and the input device to: (a) receive data relating to G from at least a dietary phosphorus intake of a hemodialysis patient or a urea kinetic modeling of the hemodialysis patient; (b) determine the $C_{SS-PRE}$ of the patient using the equation:

$$C_{SS-PRE} = \frac{(G)(10080/F)}{(K_D + K_R)n\overline{C}_{tx}t_x + K_R n\overline{C}_i(10080/F - t_{tx})} \quad (DD)$$

wherein F is a frequency of treatments per week, $t_{tx}$ is a treatment time for one hemodialysis treatment session (e.g., in units of minutes per treatment session), $K_D$ is a dialyzer phosphate clearance, $K_R$ is a residual renal clearance of phosphate, $n\overline{C}_{tx}$ is the normalized time averaged plasma phosphorus concentration during a dialysis treatment, and $n\overline{C}_i$ is the normalized time averaged plasma phosphorus concentration for an interdialytic interval; and (c) simulate the effect of at least one of a patient parameter or a treatment parameter on $C_{SS-PRE}$ of the hemodialysis patient. It should be appreciated that the variables for equation DD can be determined using any of the appropriate equations set forth herein.

Another such computing device can include a display device, an input device, a processor, and a memory device that stores a plurality of instructions, which when executed by the processor, cause the processor to operate with the display device and the input device to: (a) determine a net generation of phosphorus ("G") using the equation:

$$G = C_{SS-PRE-IN} \times \left[ \frac{(K_D + K_R)n\overline{C}_{tx}t_x + K_R n\overline{C}_i(10080/F - t_{tx})}{(10080/F)} \right] \quad (EE)$$

wherein $C_{SS-PRE-IN}$ is an initial, measured, steady state, pre-dialysis serum phosphorus level of the hemodialysis patient who is maintained by a hemodialysis therapy (e.g., identified by $K_D$, F, and $t_{tx}$) for a specified time prior to the calculation of G using equation EE. The specified time can be, for example, at least one week, two weeks, three weeks, 1 month, 2 months, 3 months, 4 months or more prior to time when G is calculated. F is a frequency of treatments per week, $t_{tx}$ is a treatment time for one hemodialysis treatment session, $K_D$ is a dialyzer phosphate clearance, $K_R$ is a residual renal clearance of phosphate, $n\overline{C}_{tx}$ is the normalized time averaged plasma phosphorus concentration during a dialysis treatment, and $n\overline{C}_i$ is the normalized time averaged plasma phosphorus concentration for an interdialytic interval; (b) predict steady state, pre-dialysis serum phosphorus levels ("$C_{SS-PRE}$") of the hemodialysis patient using the equation:

$$C_{SS-PRE} = \frac{(G)(10080/F)}{(K_D + K_R)n\overline{C}_{tx}t_x + K_R n\overline{C}_i(10080/F - t_{tx})}; \quad (FF)$$

and (c) simulate the effect of at least one of a patient parameter or a treatment parameter on $C_{SS-PRE}$ of the hemodialysis patient. It should be appreciated that the variables for equations EE and FF can be determined using any of the appropriate equations or methods set forth herein.

In any of the computing devices described herein, the information/data obtained for the hemodialysis patient can be displayed/printed out and used by the healthcare provider to provide improved treatment and nutritional regimens for the hemodialysis patient. Any of the unknown factors can be determined using any of the appropriate equations or measurements discussed herein for the methods of determining the steady state, pre-dialysis serum phosphorus levels of a hemodialysis patient.

The computing devices can also be preprogrammed or run according to software that causes the processor to operate with the display device and the input device to receive data relating to at least one of $K_R$, $K_D$, $K_M$, $V_{PRE}$, $t_{tx}$, F, $C_{PRE}$ about a month before a hemodialysis treatment session or a sampling time for collecting the serum phosphorus concentration. The computer device utilizes this information to simulate the effect of one or more of these patient parameters or treatment parameters on $C_{SS-PRE}$ of the hemodialysis patient, for example, using equations DD or FF (e.g., seeing how a change in one or more of the patient parameters or treatment parameters impacts $C_{SS-PRE}$). The computing device can be preprogrammed to display a treatment regimen of the hemodialysis patient so that $C_{SS-PRE}$ is within a desired range using any of the methods disclosed herein. In an embodiment, the computing device can be system 10 described in section I.

Figure 10:
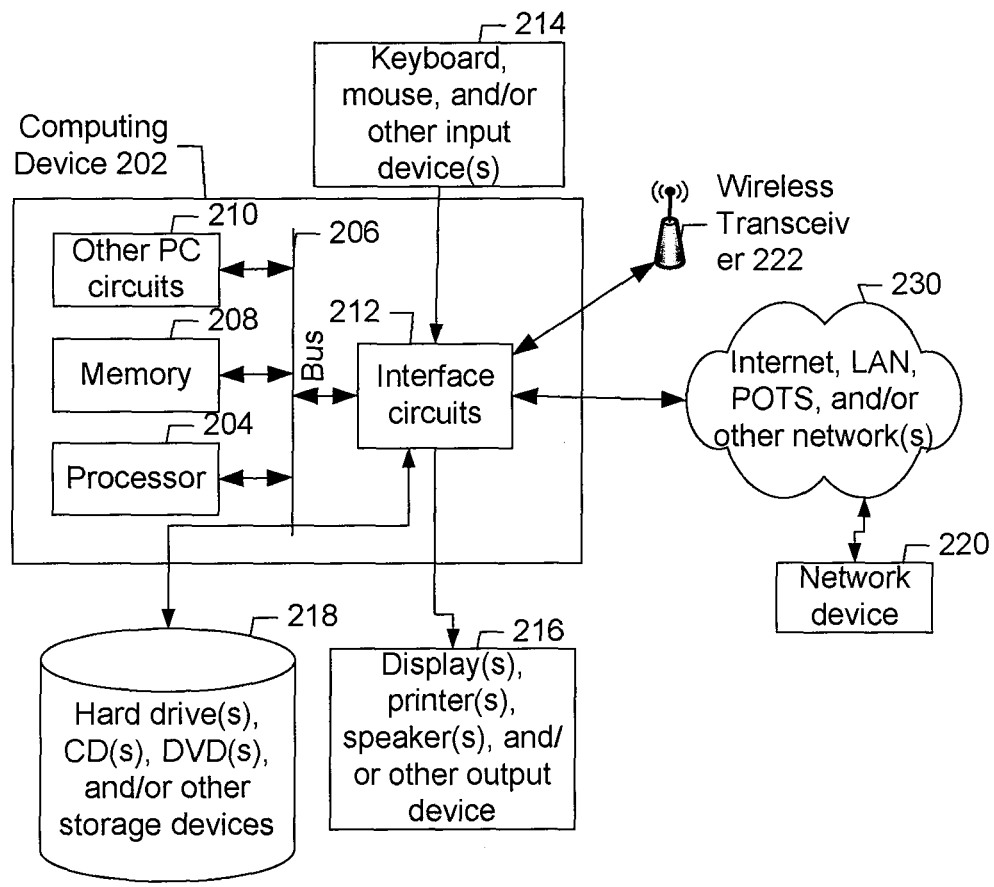
FIG. 10 illustrates an embodiment of a computing device of the present disclosure.

Any of the computer devices described herein (including any portions of system 10 described in section I) can be a device having a processor capable of receiving data and performing calculations based on that data. Such computing device can be, for example, a handheld client device, personal computer client device, database server, etc.). A more detailed block diagram of the electrical systems of the computing devices described herein is illustrated in FIG. 10. Although the electrical systems of these computing devices may be similar, the structural differences between these devices are well known. For example, a typical handheld client device is small and lightweight compared to a typical database server.

In FIG. 10, an example computing device 202 preferably includes one or more processors 204 electrically coupled by an address/data bus 206 to one or more memory devices 208, other computer circuitry 210, and one or more interface circuits 212. Processor 204 may be any suitable processor, such as a microprocessor from the INTEL PENTIUM® family of microprocessors. Memory 208 preferably includes volatile memory and non-volatile memory. Preferably, memory 208 stores a software program (e.g., Matlab, C++, Fortran, etc.) that can perform the calculations necessary according to embodiments described herein and/or that interacts with the other devices in a hemodialysis system. This program may be executed by processor 204 in any suitable manner. Memory 208 may also store digital data indicative of documents, files, programs, web pages, etc. retrieved from another computing device and/or loaded via an input device 214.

Interface circuit 212 may be implemented using any suitable interface standard, such as an Ethernet interface and/or a Universal Serial Bus ("USB") interface. One or more input devices 214 may be connected to the interface circuit 212 for entering data and commands into computing device 202. For example, input device 214 may be a keyboard, mouse, touch screen, track pad, track ball, isopoint, and/or a voice recognition system.

One or more displays, printers, speakers, and/or other output devices 216 may also be connected to computing device 202 via interface circuit 212. Display 216 may be a cathode ray tube ("CRT"), a liquid crystal display ("LCD"), or any other type of display. Display 216 generates visual displays of data generated during operation of computing device 202. The visual displays may include prompts for human input, run time statistics, measured values, calculated values, data, etc.

One or more storage devices 218 may also be connected to computing device 202 via interface circuit 212. For example, a hard drive, CD drive, DVD drive, and/or other storage devices may be connected to computing device 202. Storage devices 218 may store any type of suitable data.

Computing device 202 may also exchange data with other network devices 220 via a connection to a network 230. The network connection may be any type of network connection, such as an Ethernet connection, digital subscriber line ("DSL"), telephone line, coaxial cable, etc. This allows computing device 202 to communicate with a suitable dialysis machine, a patient database and/or a hospital network depending on the desired applications.

EXAMPLES

By way of example and not limitation, the following examples are illustrative of various embodiments of the present disclosure and further illustrate experimental testing conducted with the systems and methods in accordance with embodiments of the present disclosure.

Example 1

Objective

The objective of this analysis was to demonstrate the non-linear least squares fitting procedure for estimating patient specific parameters (e.g., $K_M$ and $V_{PRE}$) from a pseudo one-compartment model using clinical data, and to evaluate the validity of parameter estimates over different HD treatment modalities.

Pseudo One-Compartment Model

Figure 11:
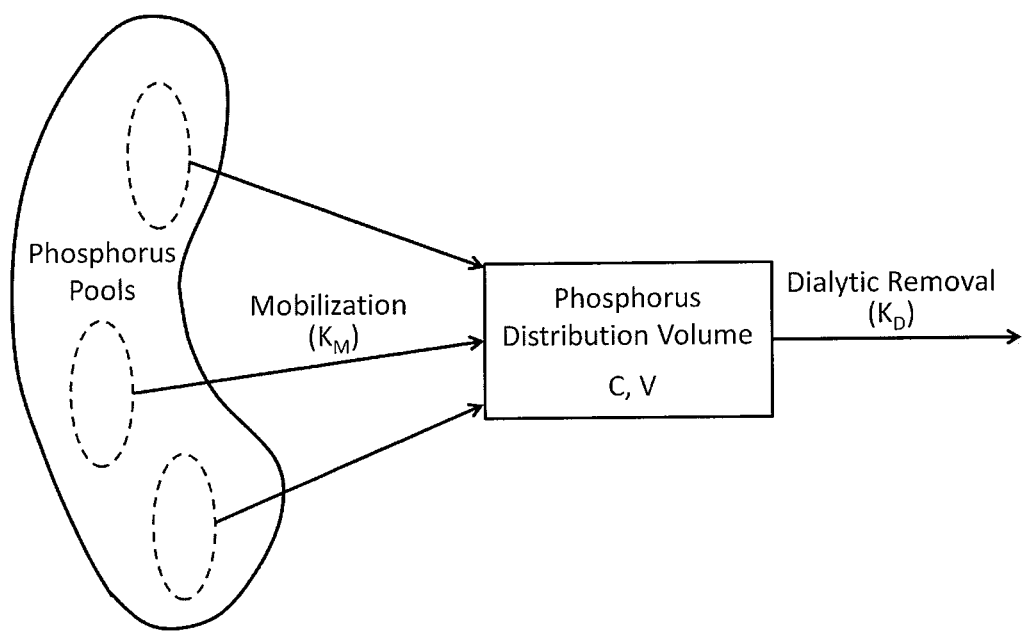
FIG. 11 is a conceptual description of the pseudo one-compartment model.

A conceptual description of the pseudo one-compartment model is shown in FIG. 11. In this model, phosphorus is removed by the dialyzer from a compartment of volume V, also called the distribution volume, and phosphorus concentration C. The distribution volume is assumed to be in equilibrium with plasma. Phosphorus mobilization into this compartment occurs from phosphorus pools in the body that are inaccessible to the dialyzer. These pools are represented as a large compartment with a constant phosphorus concentration equal to the pre-dialytic plasma phosphorus concentration ("$C_{PRE}$"). The rate of phosphorus mobilization into the distribution volume is described as the difference between pre-dialytic and instantaneous plasma phosphorus levels multiplied by the phosphorus mobilization clearance ("$K_M$"). $K_M$ is analogous to an intercompartmental mass transfer coefficient, and is assumed to be constant during the treatment and the post-dialytic rebound periods. Residual renal clearance of phosphate is neglected in this example.

Changes in the volume and phosphorus concentration of phosphorus distribution volume during and shortly after an HD treatment session are represented by equations E-A1 and E-A2, $$\frac{d(VC)}{dt} = K_M(C_{PRE} - C) - \Theta K_D C \quad \text{E-A1}$$

$$\frac{d(V)}{dt} = -\Theta Q_{UF} \quad \text{E-A2}$$

where, $\Theta$ is a variable that indicates whether dialysis treatment is taking place ($\Theta=1$) or not ($\Theta=0$), $K_D$ is the dialyzer phosphate clearance, and $Q_{UF}$ is the ultrafiltration ("UF") rate. The kinetic model described above also assumes that all fluid removed during the treatment is from the distribution volume of phosphorus.

Closed form analytical solutions to the time-dependent plasma phosphorus concentration can be obtained by integrating equations 1 and 2. For the intradialytic ($\Theta=1$) and rebound ($\Theta=0$) periods, the time dependence of phosphorus concentration can be expressed as shown by equations E-A3 and E-A4 respectively:

$$C(t) = C_{PRE}\left[\frac{K_M + (K_D - Q_{UF})\left(\frac{V_{PRE} - Q_{UF} \times t}{V_{PRE}}\right)^{\frac{K_M + K_D - Q_{UF}}{Q_{UF}}}}{K_M + K_D - Q_{UF}}\right] \quad \text{E-A3}$$

$$C(T) = C_{PRE} - (C_{PRE} - C_{POST})e^{\left(-\frac{K_M T}{V_{PRE} - Q_{UF} t_{tx}}\right)} \quad \text{E-A4}$$

wherein $V_{PRE}$ is the pre-dialytic distribution volume of phosphorus, t time during the treatment, T is time after the end of the treatment, and $t_{tx}$ is total duration of treatment prior to the rebound period. It is also assumed that distribution volume of phosphorus remains constant during the post-dialytic rebound period.

Methods

Clinical data was obtained from 5 chronic hemodialysis patients who participated in a crossover trial. Patients underwent a short HD ("SHD") treatment session and a conventional HD ("CHD") treatment session one week apart. Blood samples were collected at t=0, 60, 90 min during SHD and, t=0, 30, 60, 120, 180 min during CHD treatments. Dialysate samples were collected 60 min after the start of treatments to determine dialyzer phosphate clearance. Additional blood samples were collected at t=10 seconds, 2, 10, 30, 60 min after the end of treatments. Plasma and dialysate samples were assayed for phosphorus.

Patient specific parameters ($K_M$ and $V_{PRE}$) were estimated by non-linear least squares fitting to clinical data using equations 3 and 4. Least squares fitting was performed using a scientific computational software (MATLAB v2008a, Mathworks, Natick, Mass., USA). The model was fit to SHD and CHD data separately, resulting in two sets of $K_M$ and $V_{PRE}$ estimates for each patient. $Q_{UF}$ was calculated by the difference between pre-dialytic and post-dialytic body weight of the patient divided by total treatment time. Dialyzer phosphate clearance was calculated according to equation E-A5, where $C_D$ is the concentration of phosphorus in the dialysate outflow and $Q_D$ is the dialysate flow rate.

$$K_D = \frac{C_D(t = 60 \text{ min}) \times Q_D}{C(t = 60 \text{ min})} \quad \text{E-A5}$$

Figure 12:
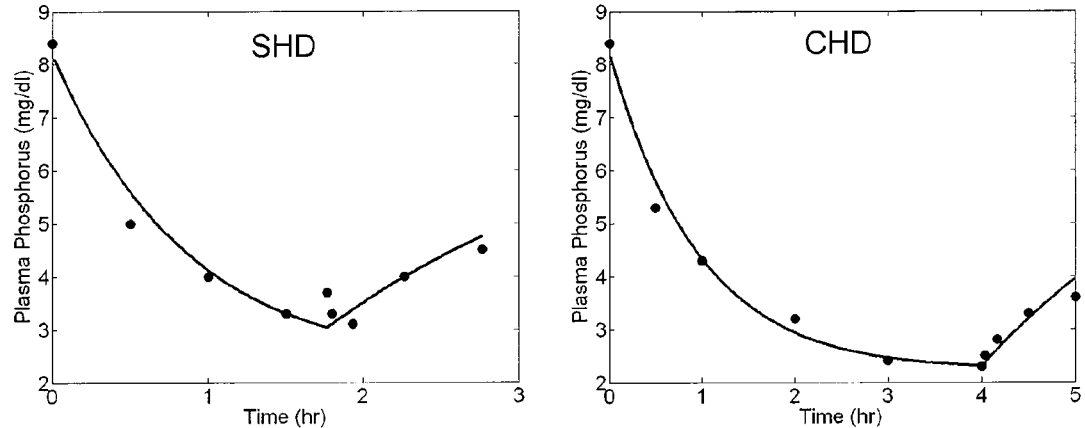
FIG. 12 shows the modeled and measured plasma phosphorus concentrations for patient 1 during short HD and conventional HD treatments.
Figure 13:
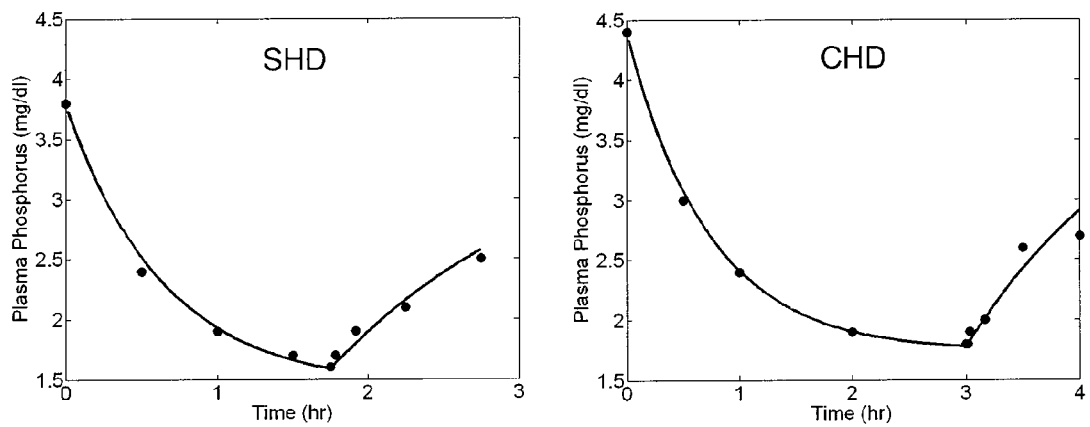
FIG. 13 shows the modeled and measured plasma phosphorus concentrations for patient 2 during short HD and conventional HD treatments.
Figure 14:
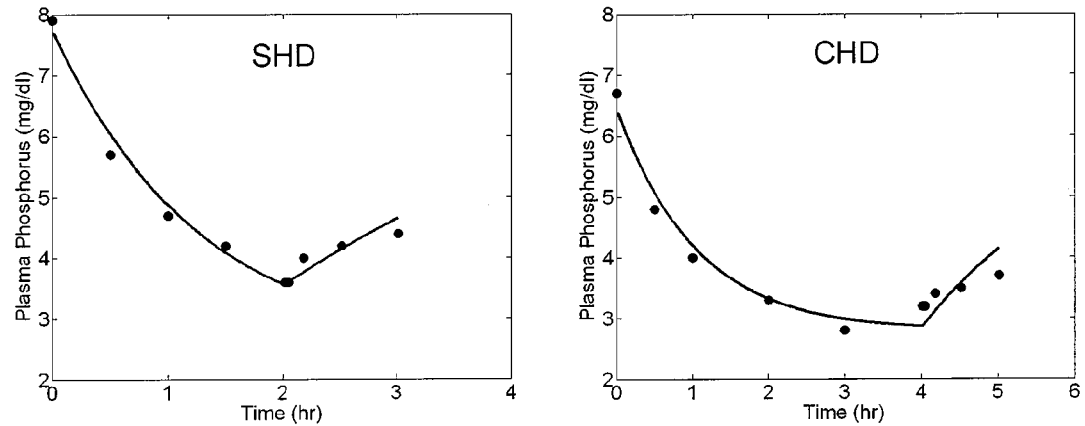
FIG. 14 shows the modeled and measured plasma phosphorus concentrations for patient 3 during short HD and conventional HD treatments.
Figure 15:
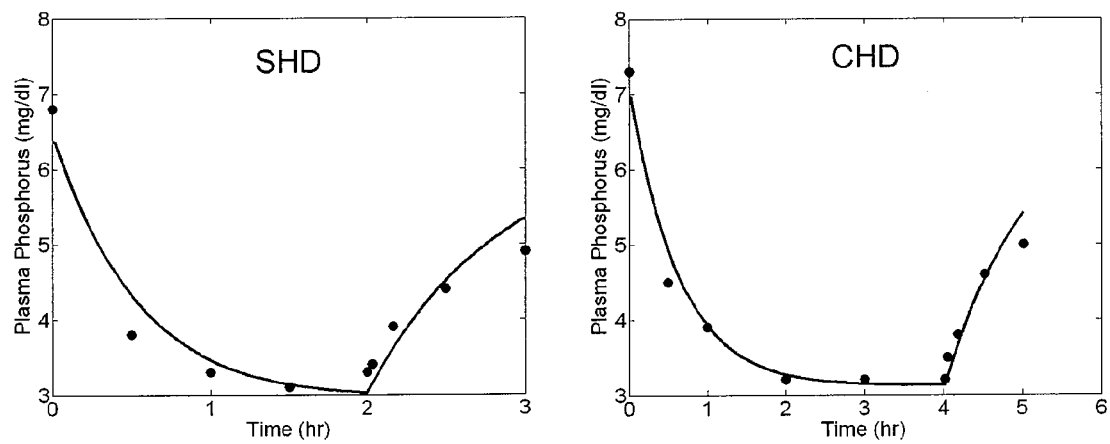
FIG. 15 shows the modeled and measured plasma phosphorus concentrations for patient 4 during short HD and conventional HD treatments.
Figure 16:
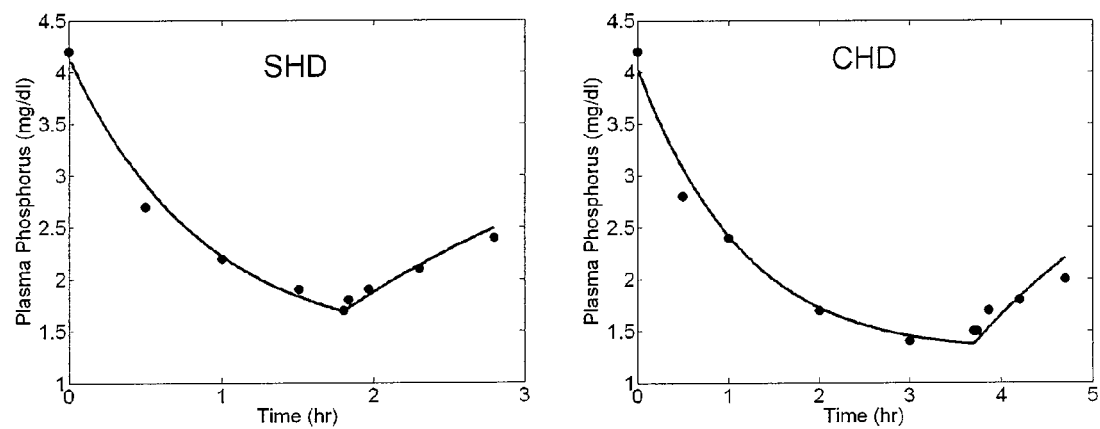
FIG. 16 shows the modeled and measured plasma phosphorus concentrations for patient 5 during short HD and conventional HD treatments.

Non-linear regression fits to clinical data from each patient are presented in FIGS. 12-16. FIG. 12 shows modeled and measured plasma phosphorus concentrations for patient 1 during SHD and CHD treatment sessions. FIG. 13 shows modeled and measured plasma phosphorus concentrations for patient 2 during SHD and CHD treatment sessions. FIG. 14 shows modeled and measured plasma phosphorus concentrations for patient 3 during SHD and CHD treatment sessions. FIG. 15 shows modeled and measured plasma phosphorus concentrations for patient 4 during SHD and CHD treatment sessions. FIG. 16 shows modeled and measured plasma phosphorus concentrations for patient 5 during SHD and CHD treatment sessions. There was good agreement between modeled and measured plasma phosphorus concentration during SHD and CHD treatment sessions.

A detailed summary of parameter estimates are presented in Table II.1. Parameter estimates varied considerably among patients, but for each patient, estimates obtained from SHD and CHD treatment sessions were similar. Low values for standard errors ("SE") indicate high precision in parameter estimates.

These results suggest that $K_M$ and $V_{PRE}$ are patient specific parameters independent of HD treatment time. Therefore extending kinetic model predictions from thrice-weekly conventional (3-4 hours) to short-daily (2-3 hours) and nocturnal HD (6-10 hours) therapies may be feasible using $K_M$ and $V_{PRE}$ values estimated from conventional HD treatments.

TABLE II.1

Estimated values of patient parameters from SHD and CHD treatment sessions.

| Patient ID | $K_M$ (SHD) (ml/min) | $K_M$ (CHD) (ml/min) | $V_{PRE}$ (SHD) (L) | $V_{PRE}$ (CHD) (L) |
| --- | --- | --- | --- | --- |
| 1 | 66 ± 10 | 55 ± 5 | 11.2 ± 1.4 | 11.8 ± 1.0 |
| 2 | 78 ± 5 | 84 ± 6 | 8.1 ± 0.5 | 9.6 ± 0.7 |
| 3 | 67 ± 8 | 96 ± 12 | 14.6 ± 1.3 | 14.0 ± 2.2 |
| 4 | 104 ± 18 | 101 ± 11 | 7.3 ± 1.1 | 8.9 ± 0.9 |
| 5 | 58 ± 5 | 50 ± 5 | 9.0 ± 0.7 | 10.7 ± 1.1 |

Parameter estimates are expressed as estimated value±standard error

Example 2

Objective

The objective of this study was to demonstrate the application of a simple method for estimating the patient parameter $K_M$ from a pseudo one-compartment model using data from conventional 4-hour hemodialysis treatments, and to evaluate the accuracy of estimated $K_M$ values via comparison to results obtained using non-linear least squares fitting.

Methods

Clinical data was obtained from 5 chronic hemodialysis patients who underwent CHD treatments. Blood samples were collected at t=0, 30, 60, 120, 180 min during the treatments and 10 seconds, 2, 10, 30, 60 min after the end of treatments. Dialysate samples were collected 60 min from the start of treatments to determine dialyzer phosphate clearance. Plasma and dialysate samples were assayed for phosphorus.

$K_M$ was computed for each patient using equation E-B1, where $C_{POST}$ is the post-dialytic plasma phosphorus concentration, $K_D$ is the dialyzer phosphate clearance, $Q_{UF}$ is the ultrafiltration rate or net fluid removal rate, and $C_{PRE}$ is the pre-dialytic plasma phosphorus concentration.

$$K_M = C_{POST}\left(\frac{K_D - Q_{UF}}{C_{PRE} - C_{POST}}\right) \qquad \text{E-B1}$$

$Q_{UF}$ was calculated by the difference between pre-dialysis and post-dialytic body weight of the patient divided by total treatment time. Dialyzer phosphate clearance was calculated according to equation E-B2, where $C_D$ is concentration of phosphorus in the dialysate outflow and $Q_D$ is the dialysate flow rate.

$$K_D = \frac{C_D(t = 60 \text{ min}) \times Q_D}{C(t = 60 \text{ min})} \qquad \text{E-B2}$$

To evaluate the accuracy of equation E-B1, computed $K_M$ values were compared with estimates obtained using non-linear least squares fitting to 10 measured intradialytic and post-dialytic rebound concentrations of plasma phosphorus, as described in Example 1.

Results $K_M$ values for individual patients, computed using equation E-B1 and estimated from non-linear least squares fitting to frequent measurements are presented in Table II.2 along with the pre-dialytic and post-dialytic plasma phosphorus concentrations, ultrafiltration rate, and the dialyzer phosphate clearance. There was good agreement between $K_M$ values obtained using equation E-B1, and non-linear least squares fitting.

These results suggest that equation E-B1 can be used as an alternative to performing non-linear least squares fitting to frequent measurements of plasma phosphorus concentrations for the estimation of patient specific $K_M$. Its simple algebraic form and utilization of only pre-dialysis and post-dialysis blood samples makes it a practical method to study kinetics of phosphorus mobilization during HD treatments on an individual patient basis.

TABLE II.2

$K_M$ values for individual patients computed from equation E-B1, and estimated using non-linear least squares fitting ("NLSQ")

| Patient ID | $C_{PRE}$ (mg/dl) | $C_{POST}$ (mg/dl) | $Q_{UF}$ (ml/min) | $K_D$ (ml/min) | $K_M$(E-B1) (ml/min) | $K_M$(NLSQ) (ml/min) |
| --- | --- | --- | --- | --- | --- | --- |
| 1 | 8.4 | 2.3 | 8 | 154 | 55 | 56 |
| 2 | 4.4 | 1.8 | 7 | 131 | 85 | 84 |
| 3 | 6.7 | 3.2 | 8 | 129 | 110 | 96 |
| 4 | 7.3 | 3.2 | 12 | 135 | 96 | 102 |
| 5 | 4.2 | 1.5 | 12 | 117 | 58 | 51 |

Abbreviations: SD, standard deviation

Example 3

Steady State Phosphorus Mass Balance Model

Objectives

As previously discussed, the inventors have proposed a kinetic model for describing changes in serum or plasma phosphorus concentrations during hemodialysis (more generally extracorporeal treatments) and the post-dialytic rebound period. That kinetic model allows prediction of intradialytic phosphorus concentrations as a function of time and total phosphate removal from the knowledge of: 1) the pre-dialysis concentration of phosphorus in plasma or serum, 2) the dialyzer clearance of phosphate, 3) the volume of distribution of phosphorus, 4) the amount of fluid removed during the treatment, and 5) a patient-specific phosphorus mobilization clearance. The steady state phosphorus mass balance model described below will be used in combination with the previous kinetic model to allow determination of pre-dialysis serum phosphorus concentration for individual patients under any hemodialysis treatment prescription when the above parameters 2-5 are established, the frequency of hemodialysis treatments per week and the hemodialysis treatment duration are prescribed, and the net generation of phosphorus (defined below), and residual kidney or renal phosphorus clearance are all known. Alternatively, the steady state phosphorus mass balance model in combination with the previous kinetic model can be used to determine the net generation of phosphorus for a given patient when the above parameters 1-5 are established and the frequency of hemodialysis treatments per week, the hemodialysis treatment duration and the residual kidney phosphorus clearance are known. As in other mass balance models, the patient is assumed to be in steady state.

Steady State Mass Balance Model

Figure 17:
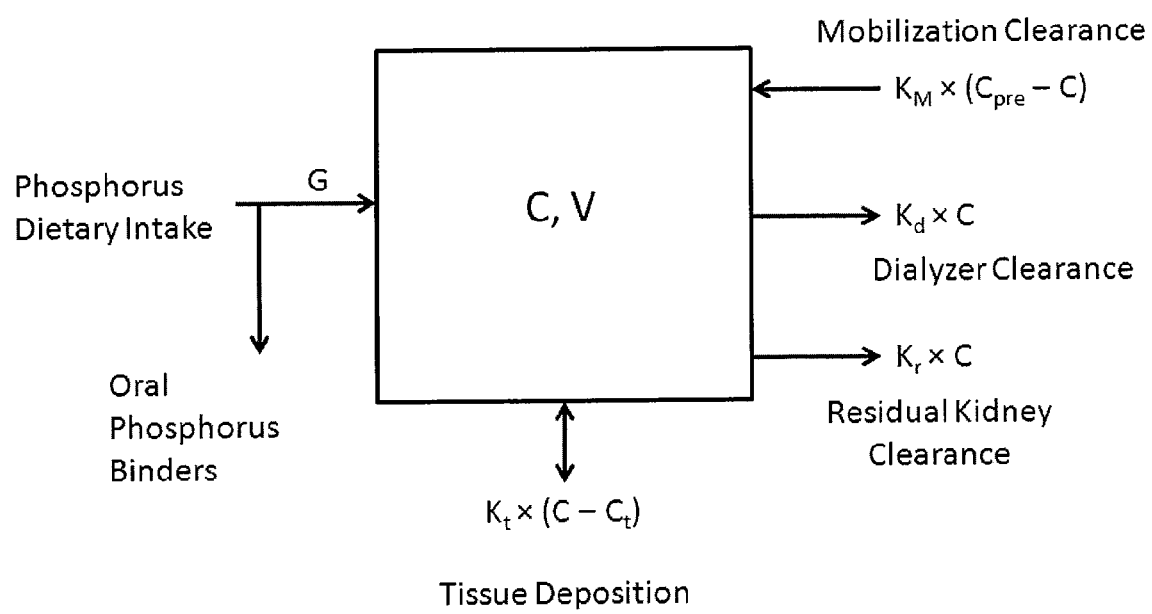
FIG. 17 is a conceptual model used to describe steady state phosphorus mass balance over a time-averaged period.

The model used to describe steady state phosphorus mass balance over a time averaged period, i.e., a week, for a patient treated by hemodialysis is shown schematically in FIG. 17. This model is a generalized version of the kinetic model described previously characterizing phosphorus kinetics during treatments and the post-dialytic rebound period. The model assumes that phosphorus is distributed in a single, well-mixed compartment.

There are several pathways that result in changes in the concentration of phosphorus ("C") within its distribution volume ("V"). Dietary intake of phosphorus is derived mostly from dietary protein; however, food additives can also contain significant amounts of phosphate. The amount of dietary phosphorus intake often exceeds the amount of phosphate that can be removed by conventional thrice weekly hemodialysis; therefore, dialysis patients are frequently prescribed oral phosphate binders to control serum phosphorus concentrations. Dietary intake of phosphorus minus the amount of phosphate that is bound and not absorbed intestinally can be combined and is defined as the net generation of phosphorus ("G"); this parameter will be assumed to be a constant in this model. Phosphorus can be removed directly from its distribution volume by dialyzer clearance ("$K_D$") or residual renal or kidney clearance ("$K_R$"). As described previously in the kinetic model, phosphorus can also be mobilized from other compartments at a rate proportional to the difference between the instantaneous and the pre-dialysis ("$C_{PRE}$") phosphorus concentrations. The proportionality parameter has been termed the phosphorus mobilization clearance ("$K_M$"). Phosphorus can also be deposited into tissues depending on a critical tissue concentration ("$C_t$"); this process has been modeled as a tissue deposition clearance ("$K_t$").

The model shown in FIG. 17 was devised to identify all major pathways for phosphorus distribution in hemodialysis patients; however, it is likely too complex to be useful clinically and requires simplification. Specifically, tissue deposition of phosphorus is likely to be small compared with the other pathways and can be neglected as a first approximation in this mass balance model.

A mass balance differential equation for the model shown in FIG. 17 (neglecting tissue deposition of phosphorus) is the following:

$$\frac{d(CV)}{dt} = G - K_D C - K_R C + K_M (C_{PRE} - C) \qquad \text{E-C1}$$

Assuming that hemodialysis treatment sessions are symmetrically placed throughout the week, integrating equation E-C1 over a week is equivalent to integrating it over one complete cycle of a treatment (with a treatment time of $t_{tx}$) and an interdialytic interval between treatments (with a time of $T_i$). Note that lower case t indicates time during the treatment and it varies from 0 to $t_{tx}$, whereas T indicates the time during the interdialytic interval and it varies from 0 to $T_i$. The values of $t_{tx}$ and $T_i$ are related and dependent on the number of treatments per week (the above mathematical analysis is general and applies to an arbitrary number of hemodialysis treatment sessions per week; here, F denotes the number of treatments per week). If t and T are reported in units of hours, then $T_i = 168/F - t_{tx}$. If t and T are reported in units of minutes, then $T_i = 10080/F - t_{tx}$. This integration results in equation E-C2 after some rearrangement.

$$\Delta(CV) - K_M \int_0^{t_{tx}+T_i} [C_{PRE} - C(\tau)] d\tau = \qquad \text{E-C2}$$

$$G(t_{tx} + T_i) - (K_D + K_R) \int_{t=0}^{t_{tx}} C(\tau) d\tau - K_R \int_{T=0}^{T_i} C(\tau) d\tau$$

where $\Delta(CV)$ indicates the change in phosphorus mass within its volume of distribution. Note that the second term on the left hand side of this equation indicates (minus) the mass of phosphorus transported into V via the mobilization pathway.

Assuming further that the patient is in steady state and total phosphorus mass in the body (i.e., left hand side of equation E-C2) does not change during one complete cycle of a treatment and an interdialytic interval, the left hand side of equation E-C2 must be zero; thus, equation E-C2 is reduced in steady state to the following:

$$0 = G(t_{tx} + T_i) - (K_D + K_R) \int_{t=0}^{t_{tx}} C(\tau) d\tau - K_R \int_{T=0}^{T_i} C(\tau) d\tau \qquad \text{E-C3}$$

To use this integrated mass balance equation, it is necessary to calculate both the integrals in equation E-C3. Note that the first integral is over the time period during the treatment and the second is over the time period during the interdialytic interval.

To evaluate the integrals in equation E-C3, the inventors make two additional assumptions. First, the inventors assume that changes in phosphorus concentration during a treatment and the post-dialytic rebound period can be described by the previously proposed kinetic model where net generation of phosphorus can be neglected. Second, the inventors assume that this same kinetic model describes changes in phosphorus concentration during the entire interdialytic interval, not just the post-dialysis rebound period. The equation describing the kinetic model is the following $$\frac{d(CV)}{dt} = -K_D C - K_R C + K_M (C_{PRE} - C) \qquad \text{E-C4}$$

Equation E-C4 can be solved analytically; the time dependence of the serum phosphorus concentration during the treatment can be described by $$\frac{C(t)}{C_{PRE}} = \frac{K_M}{K_M + K_R + K_D - Q_{UF}} + \qquad \text{E-C5}$$

$$\left[1 - \frac{K_M}{K_M + K_R + K_D - Q_{UF}}\right] \left[\frac{V(t)}{V_{PRE}}\right]^{(K_M + K_D + K_R - Q_{UF})/Q_{UF}}$$

where it has been assumed that fluid is removed from the patient at a constant rate ("$Q_{UF}$"), such that the distribution volume decreases linearly from its initial, pre-dialysis value ("$V_{PRE}$") throughout the treatment. Stated in mathematical terms, $$V(t) = V_{PRE} - Q_{UF} \times t \qquad \text{E-C6}$$

Thus, it is assumed that all fluid removed during the treatment is removed from the distribution volume of phosphorus.

During the rebound period (and the entire interdialytic interval), equation E-C4 remains valid except that $K_D$ is zero. Assuming that the patient gains fluid at a constant rate ("$Q_{WG}$") during the interdialytic interval, such that the distribution volume increases linearly from its initial post-dialysis value ("$V_{POST}$"), the analytical solution describing the time dependence of the serum phosphorus concentration during the interdialytic interval is $$\frac{C(T)}{C_{PRE}} = \left[\frac{C_{POST}}{C_{PRE}} - \frac{K_M}{K_M + K_R + Q_{WG}}\right]\left[\frac{V(T)}{V_{POST}}\right]^{-(K_M + K_R + Q_{WG})/Q_{WG}} + \qquad \text{E-C7}$$

$$\frac{K_M}{K_M + K_R + Q_{WG}}$$

where the time dependence of the distribution volume during the interdialytic interval is described by $$V(T)=V(T=0)+Q_{WG} \times T = V_{POST}+Q_{WG} \times T = V_{PRE}-Q_{UF} \times t_{tx}+Q_{WG} \times T \quad \text{E-C8}$$

Note that it is assumed that all fluid gained during the interdialytic interval is confined to the distribution volume of phosphorus. The two integrals in equation E-C3 can now be obtained by integrating equations E-C5 and E-C7. The normalized time averaged plasma phosphorus concentration during dialysis treatments ($n\overline{C}_{tx}$) is obtained by integrating equation E-C5:

$$n\overline{C}_{tx} = \left(\frac{1}{t_{tx}C_{PRE}}\right)\int_0^{t_{tx}} C(\tau)d\tau = \frac{1}{t_{tx}}\left\{\left[\frac{K_M t_{tx}}{K_M+K_R+K_D-Q_{UF}}\right]+ \right. \quad \text{E-C9}$$

$$\left[1-\frac{K_M}{K_M+K_R+K_D-Q_{UF}}\right]\left[\frac{V_{PRE}}{K_M+K_R+K_D}\right]\left[1-\right.$$

$$\left.\left.\left(\frac{V_{POST}}{V_{PRE}}\right)^{(K_M+K_R+K_D)/Q_{UF}}\right]\right\}$$

Integration of equation E-C7 and calculation of $C_{POST}/C_{PRE}$ from equation E-C5 when $t=t_{tx}$ gives the normalized time averaged plasma phosphorus concentration for the interdialytic interval ($n\overline{C}_i$):

$$n\overline{C}_i = \left(\frac{1}{T_i C_{PRE}}\right)\int_0^{T_i} C(\tau)d\tau = \frac{1}{10080/F - t_{tx}} \quad \text{E-C10}$$

$$\left\{\begin{array}{l}\left[\frac{K_M(10080/F - t_{tx})}{K_M+K_R+Q_{WG}}\right]+ \\ \left[\frac{K_M}{K_M+K_R+K_D-Q_{UF}}+\left[1-\frac{K_M}{K_M+K_R+K_D-Q_{UF}}\right]\right] \\ \left[\frac{V_{POST}}{V_{PRE}}\right]^{(K_M+K_D+K_R-Q_{UF})/Q_{UF}} - \frac{K_M}{K_M+K_R+Q_{WG}}\right] \times \\ \left[\frac{V_{POST}}{K_M+K_R}\right]\left[1-\left(\frac{V_{POST}}{V_{PRE}}\right)^{(K_M+K_R)/Q_{WG}}\right]\end{array}\right\}$$

When equations E-C3, E-C9 and E-C10 are combined, the resulting equation governing phosphorus mass balance at steady state can be expressed as:

$$G = C_{PRES-SS-IN} \times \frac{(K_D+K_R)n\overline{C}_{tx}t_{tx}+K_R n\overline{C}_i(10080/F - t_{tx})}{10080/F} \quad \text{E-C11}$$

$C_{SS-PRE-IN}$ is an initial, measured, steady state, pre-dialysis serum phosphorus level of the hemodialysis patient who is maintained by a hemodialysis therapy (e.g., identified by $K_D$, F and $t_{tx}$) for a specified time prior to the calculation of G using equation E-C11. Equation E-C11 can be used to predict G if the pre-dialysis serum concentration is measured in a patient with knowledge of various treatment and patient parameters.

Once G has been calculated using equation E-C11 or estimated by other methods, it can be used in predicting the effect of changes in hemodialysis treatment parameters on the steady state serum phosphorus concentration by rearranging equation E-C11 to the following:

$$C_{PRE-SS} = G \times \frac{10080/F}{(K_D+K_R)n\overline{C}_{tx}t_{tx}+K_R n\overline{C}_i(10080/F - t_{tx})} \quad \text{E-C12}$$

In general, there is an optimal range of pre-dialysis serum phosphorus levels in patients with end stage renal disease; thus, equation E-C12 can be used to optimize the prescription to obtain a desired pre-dialysis serum phosphorus concentration. It should be mentioned that changes in the hemodialysis prescription or in patient behavior (e.g., dietary intake) could lead to changes in G; thus, the iterative use of equations E-C11 and E-C12 to optimize $C_{SS-PRE}$ may be necessary.

Equation E-C12 can be used to predict the pre-dialysis serum phosphorus concentration with knowledge of various treatment and patient parameters. Thus, equations E-C9 to E-C12 can be viewed as defining a steady state phosphorus mass balance of the hemodialysis patient.

Equations E-C5 to E-C10 do not apply when there is negligible net ultrafiltration or fluid removal from the patient during the treatment and no weight gain between treatments. When there is negligible ultrafiltration during the treatment and no weight gain between treatments, equations E-C5 to E-C10 become:

$$\frac{C(t)}{C_{PRE}} = \frac{K_M}{K_M+K_R+K_D}+ \quad \text{E-C5A}$$

$$\left[1-\frac{K_M}{K_M+K_R+K_D}\right]\times\exp[-(K_D+K_R+K_M)t/V_{PRE}]$$

$$V(t) = V(t=0) = V_{PRE} \quad \text{E-C6A}$$

$$\frac{C(T)}{C_{PRE}} = \left[\frac{C_{POST}}{C_{PRE}}-\frac{K_M}{K_M+K_R}\right]\times \quad \text{E-C7A}$$

$$\exp[-(K_R+K_M)T/V_{POST}]+\frac{K_M}{K_M+K_R}$$

$$V(T) = V(T=0) = V_{POST} = V_{PRE} \quad \text{E-C8A}$$

$$n\overline{C}_{tx} = \left(\frac{1}{t_{tx}C_{PRE}}\right)\int_0^{t_{tx}} C(\tau)dt = \quad \text{E-C9A}$$

$$\frac{1}{t_{tx}}\left\{\left[\frac{K_M t_{tx}}{K_M+K_R+K_D}\right]+\left[1-\frac{K_M}{K_M+K_R+K_D}\right]\right.$$

$$\left[\frac{V_{PRE}}{K_M+K_R+K_D}\right]$$

$$\left.[1-\exp(-(K_D+K_R+K_M)t_{tx}/V_{PRE})]\right\}$$

$$n\overline{C}_i = \left(\frac{1}{T_i C_{PRE}}\right)\int_0^{T_i} C(\tau)d\tau = \quad \text{E-C10A}$$

$$\frac{1}{10080/F - t_{tx}}\left\{\left[\frac{K_M(10080/F - t_{tx})}{K_M+K_R}\right]+\right.$$

$$\left[\frac{K_M}{K_M+K_R+K_D}+\left[1-\frac{K_M}{K_M+K_R+K_D}\right]\right]\times$$

$$\exp[-(K_D+K_R+K_M)t_{tx}/V_{PRE}] -$$

$$\left.\frac{K_M}{K_M+K_R}\right]\times\left[\frac{V_{POST}}{K_M+K_R}\right]$$

$$\left.[1-\exp(-(K_R+K_M)(10080/F - t_{tx})/V_{POST})]\right\}$$

Under these conditions, equations E-C11 and E-C12 can be used with these modified equations.

Applications

Equations E-C9 to E-C11 can be used calculate patient specific values of G from the data analyzed in Examples 1 and 2. The measured pre-dialysis concentrations of phosphorus ("$C_{PRE}$") and the calculated values of G from that data during conventional 4-hour treatments are summarized in the Table II.3 below.

TABLE II.3

| Patient Label | $C_{PRE}$ (mg/dl) | G (g/week) |
|---|---|---|
| Patient 1 | 8.4 | 4.13 |
| Patient 2 | 4.4 | 1.71 |
| Patient 3 | 6.7 | 3.64 |
| Patient 4 | 7.3 | 3.83 |
| Patient 5 | 4.2 | 1.68 |

The calculated G values are consistent with expected phosphorus net generation rates in chronic hemodialysis patients.

Equations E-C9 to E-C12 can also be used to simulate the effect of patient parameters (G, $K_M$ and $K_R$) and treatment parameters ($t_{tx}$, $K_D$ and F) on pre-dialysis serum phosphorus concentrations. Several different simulations will be illustrated; $K_R$ will be assumed to be zero in these simulations. These simulation examples show that the steady state mass balance model predicts results that are similar to those expected from the medical literature.

The importance of treatment time under conditions relevant to thrice weekly hemodialysis is of high clinical interest; therefore, the inventors examined the effect of treatment time on the pre-dialysis serum phosphorus concentration at the same dialysis dose or urea Kt/V. The inventors used the above described model to perform computer simulations of steady state serum phosphorus concentrations during thrice weekly hemodialysis. Simulations were performed for a fixed net phosphorus intake or generation rate (dietary intake minus absorption by oral binders), a urea Kt/V of 1.4 and a constant relationship between dialyzer clearances of phosphate and urea (i.e., the inventors assumed that dialyzer clearance of phosphate was one-half of that for urea and that the phosphorus distribution volume was one-third of that for urea).

Simulated pre-dialysis serum phosphorus concentrations (in mg/dl) are tabulated in Table II.4 below for hypothetical patients with different $K_M$, a post-dialysis phosphorus distribution volume of 12 L, and net fluid removal per treatment of 2 L.

TABLE II.4

| Treatment Time | $K_M$ (ml/min) | | |
|---|---|---|---|
| (min) | 50 | 100 | 200 |
| 180 | 7.65 | 6.91 | 6.07 |
| 240 | 7.36 | 6.56 | 5.75 |
| 300 | 7.07 | 6.24 | 5.47 |

For a given patient, increasing treatment time at a given urea Kt/V resulted in modest decreases in pre-dialysis serum phosphorus concentration. Similar findings were obtained for other values of urea Kt/V between 1.0 and 2.0 (results not shown). These predictions show that use of urea Kt/V as the only measure of dialysis dose or dialysis adequacy does not account for differences in phosphate removal.

Figure 18:
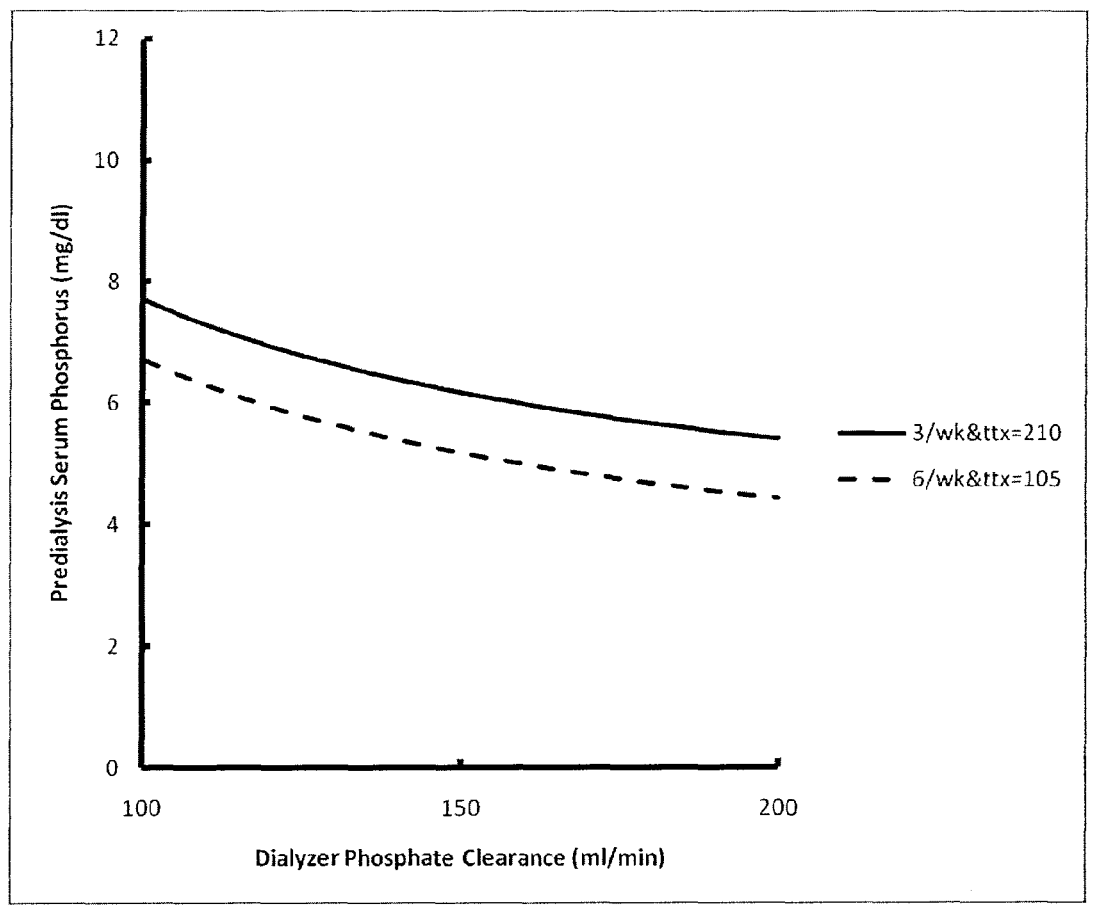
FIG. 18 illustrates the effect of treatment frequency per se on pre-dialysis serum phosphorus concentration as a function of dialyzer phosphate clearance.

FIG. 18 illustrates the effect of treatment frequency per se on pre-dialysis serum phosphorus concentration as a function of dialyzer phosphate clearance where it was assumed that $K_M$ was equal to 100 ml/min, V was assumed equal to 10 L with no fluid removal during the treatment, the treatment time was 630 minutes/week and the net generation of phosphorus was kept constant at 3 g/week. There is a relatively uniform decrease in pre-dialysis serum phosphorus concentration upon increasing treatment frequency from 3-times per week to 6-times per week, independent of dialyzer phosphate clearance. The uniformity of the decrease was surprising, it varied between 0.98 and 1.00 when $K_M$=100 ml/min as shown in this figure (for dialyzer phosphate clearance between 100 and 200 ml/min). Relatively uniform decreases in concentration were also evident for $K_M$ of 50, 150 and 200 ml/min (data not shown). The respective decreases in pre-dialysis serum phosphorus concentration were 1.67-1.84 ($K_M$=50 ml/min), 0.60-0.63 ($K_M$=150 ml/min) and 0.40-0.43 ($K_M$=200 ml/min).

Figure 19:
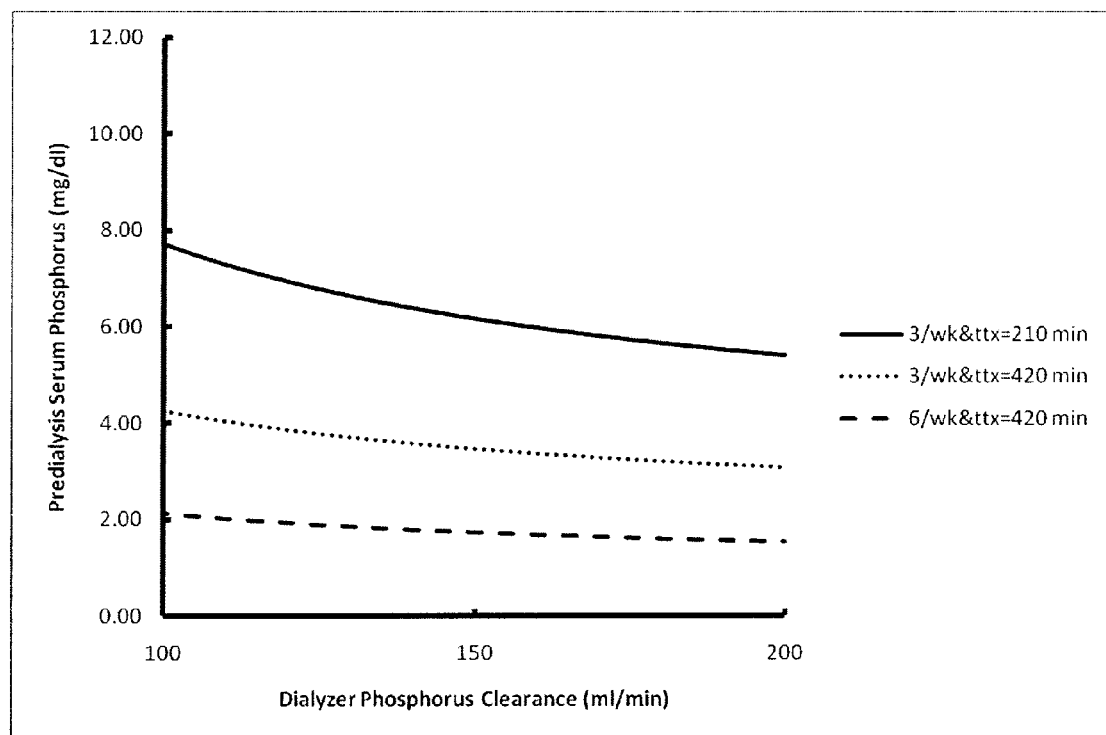
FIG. 19 shows the effects of an increase in treatment time and frequency with reference to nocturnal forms of hemodialysis.

FIG. 19 illustrates the effects of an increase in treatment time and frequency with reference to nocturnal forms of hemodialysis. Doubling treatment time during three-times per week therapy produces substantial reductions in pre-dialysis serum phosphorus concentration. When these reductions are compared with those for doubling treatment frequency at the same weekly treatment time as in FIG. 18, it can be concluded that doubling treatment time (at the same treatment frequency) has a more substantial effect on pre-dialysis serum phosphorus concentrations than does doubling frequency (at the same weekly treatment time). Doubling both treatment time and treatment frequency reduces pre-dialysis serum phosphorus concentration even further.

Figure 20:
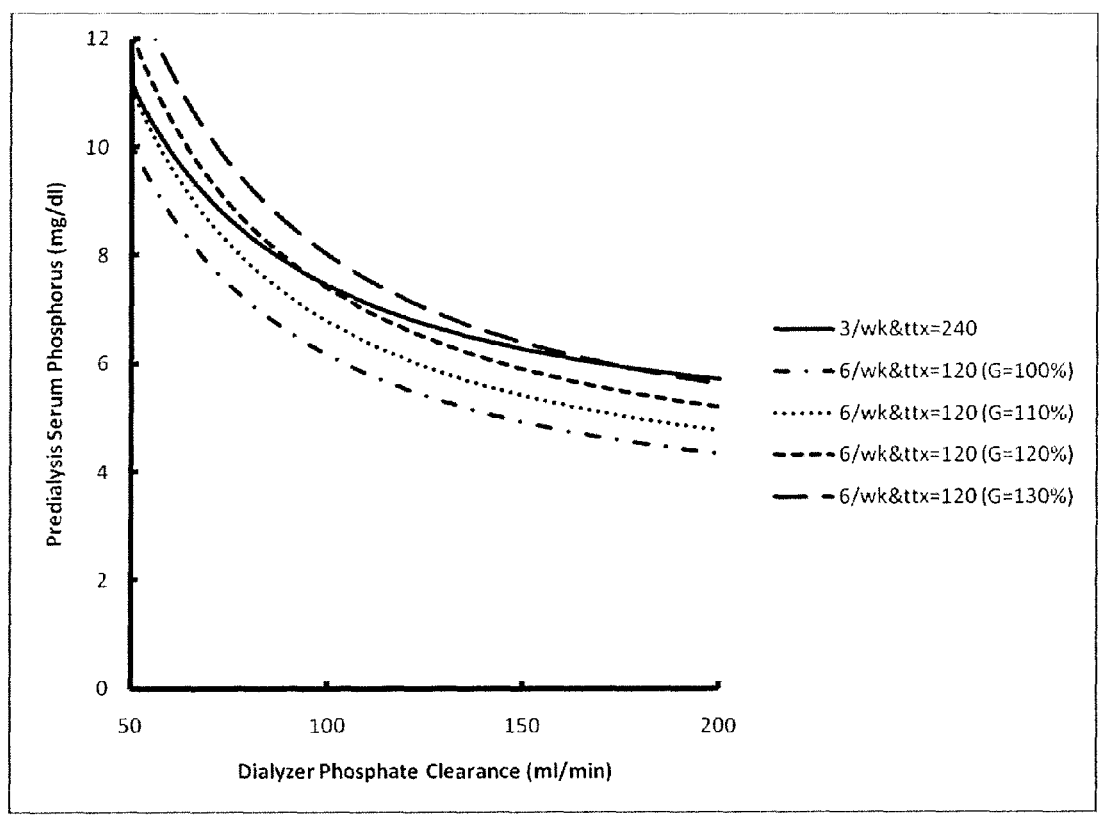
FIG. 20 shows the effect of increasing treatment frequency and treatment time relevant to short daily hemodialysis on pre-dialysis serum phosphorus concentration—$K_M$=50 ml/min.
Figure 21:
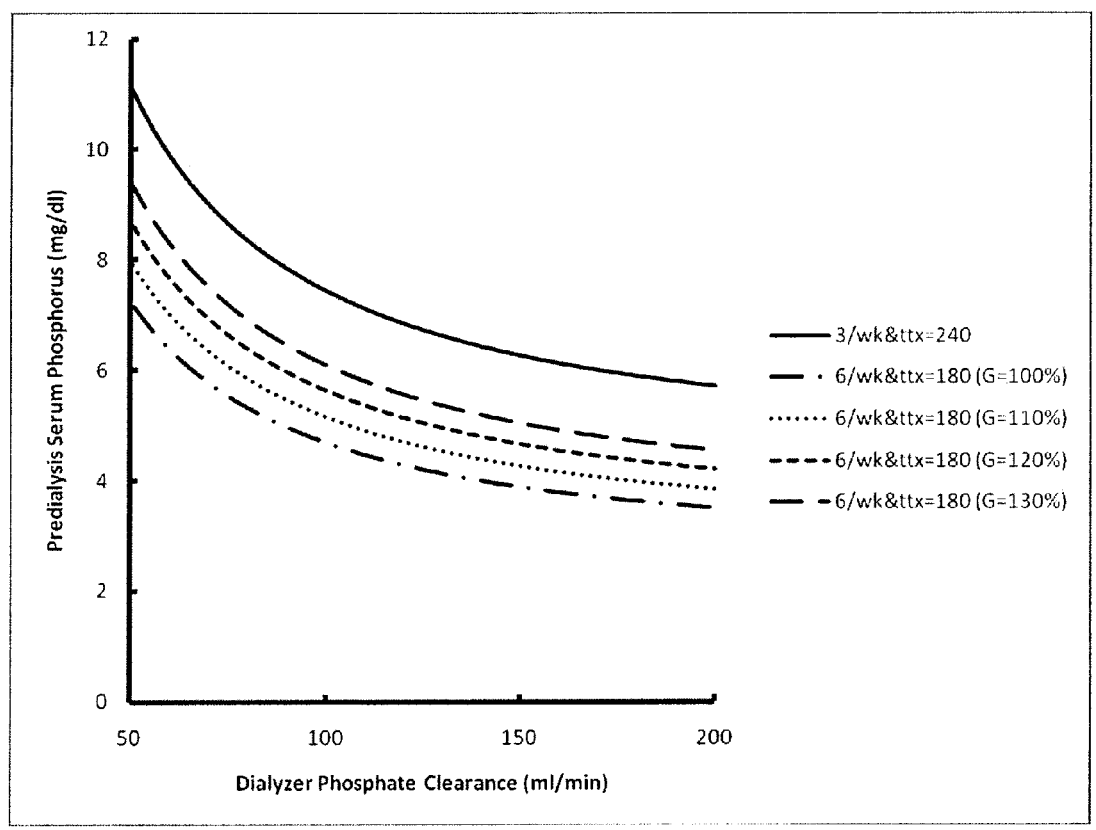
FIG. 21 shows the effect of increasing treatment frequency and treatment time relevant to short daily hemodialysis on pre-dialysis serum phosphorus concentration—$K_M$=50 ml/min.
Figure 22:
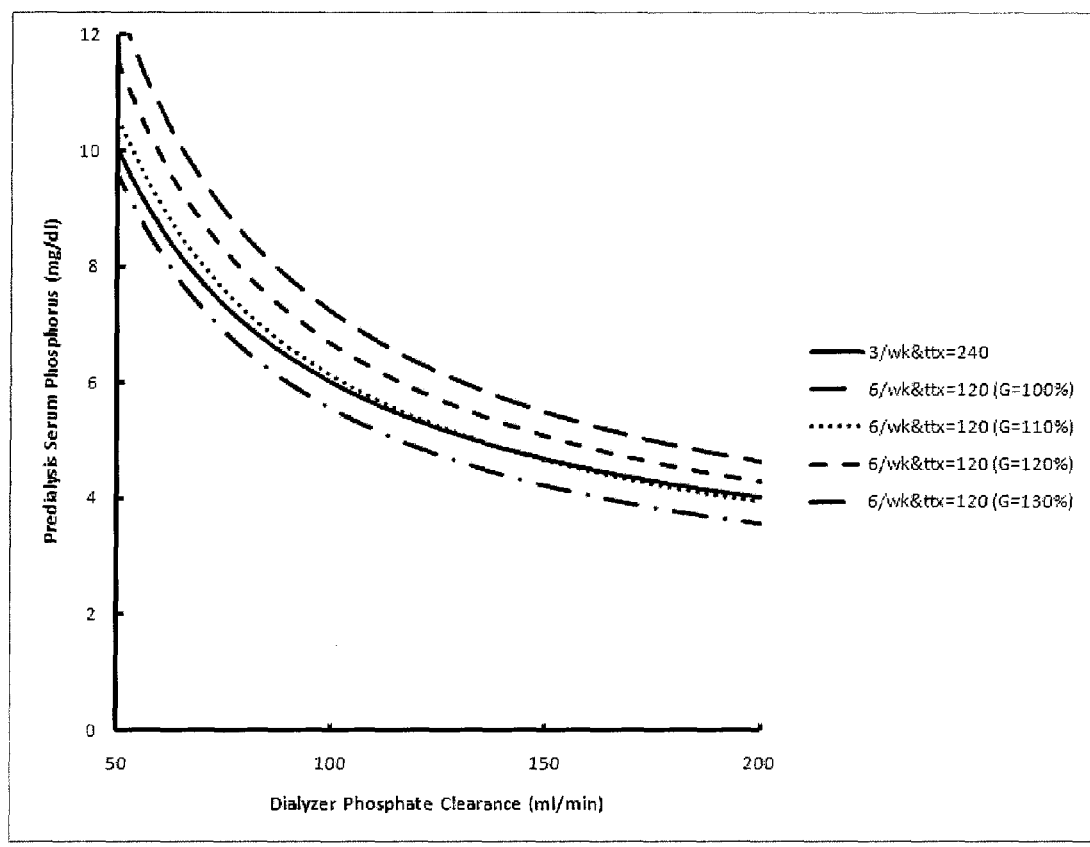
FIG. 22 shows the effect of increasing treatment frequency and treatment time relevant to short daily hemodialysis on pre-dialysis serum phosphorus concentration—$K_M$=150 ml/min.
Figure 23:
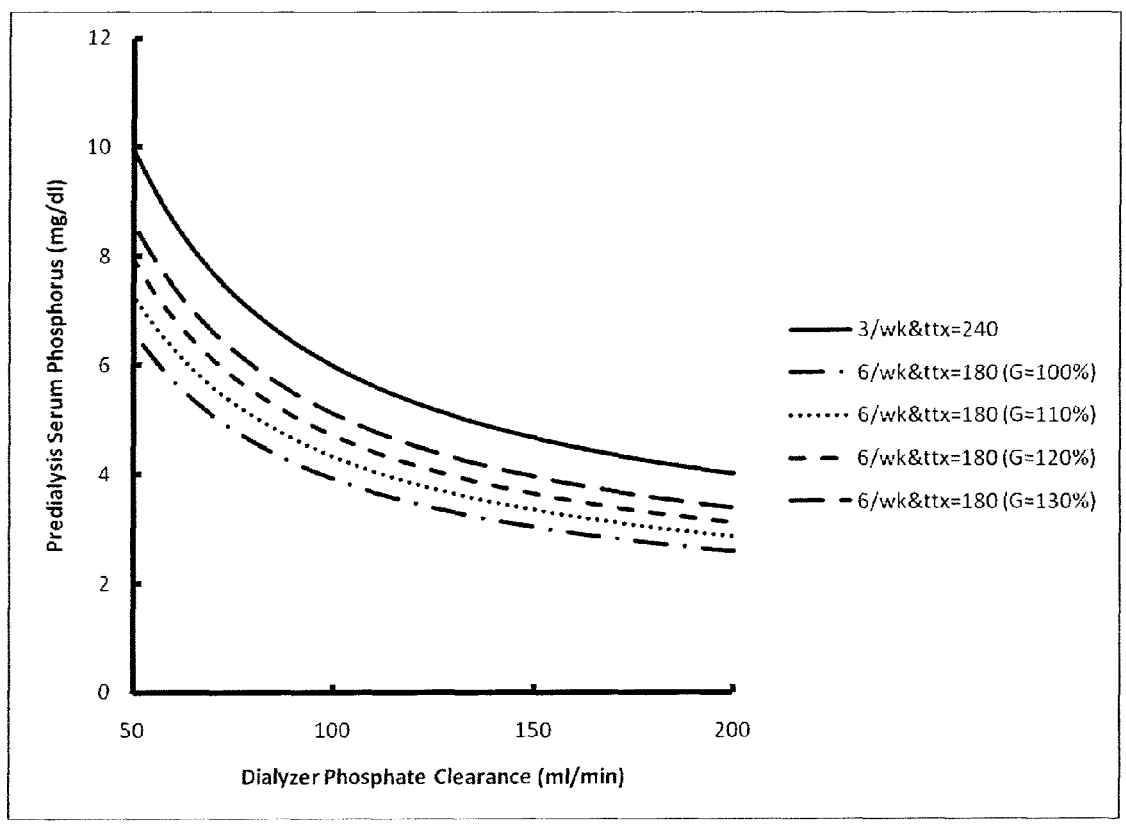
FIG. 23 shows the effect of increasing treatment frequency and treatment time relevant to short daily hemodialysis on pre-dialysis serum phosphorus concentration—$K_M$=150 ml/min.

Previous clinical studies have shown that patients treated by short daily hemodialysis often have a higher rate of protein catabolism (or protein nitrogen appearance) and a higher dietary intake of both protein and phosphorus. The increase in the protein nitrogen appearance rate has been reported to be approximately 20%. Therefore, the inventors evaluated the effect of increasing treatment frequency and treatment time relevant to short daily hemodialysis on pre-dialysis serum phosphorus concentration when net generation of phosphorus was increased up to 30% more than during conventional 3-times per week hemodialysis therapy. These results assuming post-dialytic phosphorus distribution volume of 10 L with 6 L of fluid removal per week are shown in FIGS. 20-21 for $K_M$=50 ml/min and FIGS. 22-23 for $K_M$=150 ml/min. As expected, pre-dialysis serum phosphorus concentrations were higher for lower $K_M$ values. The interactions between $K_M$, dialyzer phosphate clearance ("$K_D$") and treatment frequency and treatment time are complex when net generation of phosphorus is increased. Some specific values of pre-dialysis serum phosphorus concentration in mg/dl during conventional 3-times per week hemodialysis ("CHD") and during short daily hemodialysis ("SDHD") when net generation of phosphorus during the latter therapy was increased by 20% are tabulated in Table II.5.

TABLE II.5

| | $K_M$ = 50 ml/min | | | $K_M$ = 150 ml/min | | |
|---|---|---|---|---|---|---|
| | CHD | SDHD | SDHD | CHD | SDHD | SDHD |
| Treatment Time (min) | 240 | 120 | 180 | 240 | 120 | 180 |
| $K_D$ (ml/min)  80 | 8.34 | 8.53 | 6.38 | 6.98 | 7.85 | 5.52 |
| 110 | 7.11 | 6.97 | 5.36 | 5.62 | 6.22 | 4.42 |
| 140 | 6.43 | 6.10 | 4.80 | 4.86 | 5.29 | 3.80 |

Increasing hemodialysis treatment session frequency without an increase in weekly treatment time (CHD to SDHD at a treatment time of 120 min) may result in either an increase or a decrease in pre-dialysis serum phosphorus concentration, depending on both dialyzer phosphate clearance and the patient-specific $K_M$. Further, short daily hemodialysis with reduced dialyzer phosphate clearance does not result in reductions in pre-dialysis serum phosphorus concentration unless treatment time is increased substantially. The inventors conclude that increasing both dialyzer phosphate clearance and treatment time during short daily hemodialysis can result in clinically significant reductions in pre-dialysis serum phosphorus concentration.

An additional example of the use of this steady state mass balance model is its application to determining optimal hemodialysis prescriptions during frequent nocturnal hemodialysis (e.g. 6-times per week, 8 hours per treatment). During this therapy, $K_D$s are often empirically lowered by adding phosphate salt supplements to the dialysis solution in order to maintain pre-dialysis serum phosphorus concentrations within an optimal range; however, there are no quantitative guides to determine an optimal $K_D$. The inventors used the above model to determine $K_D$ that maintains pre-dialysis serum phosphorus concentration within the range recommended by the Dialysis Outcomes and Practice Patters Study ("DOPPS") of 3.6-5.0 mg/dl. Computer simulations were performed for a given dietary phosphorus intake (e.g., assuming no use of oral binders), post-dialytic phosphorus distribution volume of 12 L, and net fluid removal per treatment of 1 L.

Calculated ranges for $K_D$ (ml/min) to maintain pre-dialysis serum phosphorus concentration between 3.6 and 5.0 mg/dl for hypothetical patients with different $K_M$ at steady state are tabulated in Table II.6.

TABLE II.6

| Dietary P Intake | $K_M$ (ml/min) | | |
|---|---|---|---|
| | 50 | 100 | 150 |
| 4 g/week | 40-70 | 35-53 | 32-48 |
| 5 g/week | 57-114 | 46-75 | 42-65 |
| 6 g/week | 81-200 | 60-102 | 54-84 |

These simulations demonstrate that individualization of $K_D$, depending on both dietary intake of phosphorus and the patient-specific $K_M$, is required during frequent nocturnal hemodialysis.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of predicting serum phosphorus concentrations in a patient during hemodialysis, the method comprising:

measuring serum phosphorus concentrations ("C") of the patient over a hemodialysis treatment session time and an ultrafiltration rate ("$Q_{UF}$") calculated by a difference between pre- and post-dialytic body weight of the patient during an initial hemodialysis treatment session divided by a total treatment time of the treatment session;

estimating $K_M$ and $V_{PRE}$ for the patient using a non-linear least squares fitting to the equations:

$$C(t) = C_{PRE}\left[\frac{K_M + (K_D + K_R - Q_{UF})\left(\frac{V(t)}{V_{PRE}}\right)^{\frac{K_M + K_D + K_R - Q_{UF}}{Q_{UF}}}}{K_M + K_D + K_R - Q_{UF}}\right]$$

and $$C(T) = C_{PRE} - (C_{PRE} - C_{POST})e^{\left(-\frac{K_M T}{V_{PRE} - Q_{UF} t_{tx}}\right)}$$

wherein t is a time during the hemodialysis treatment session,

T is a time after an end of the hemodialysis treatment session, $t_{tx}$ is a total duration of the hemodialysis treatment session, $C_{PRE}$ is a pre-dialysis plasma phosphorus concentration, $C_{POST}$ is a post-dialytic plasma phosphorus concentration, $K_M$ is a phosphorus mobilization clearance of the patient, $K_R$ is a residual renal clearance of phosphate, $K_D$ is a dialyzer phosphate clearance, $V_{PRE}$ is a pre-dialysis distribution volume of phosphorus of the patient, and $$V(t) = V_{PRE} - Q_{UF} \times t \quad \text{(eqn. 1-C); and}$$

predicting C of the patient at any time during any hemodialysis treatment session by using the equations 1-A and 1-B with the estimated $K_M$ and $V_{PRE}$ of the patient.

2. The method of claim 1, wherein $K_D$ is determined using the equation:

$$K_D = Q_B \frac{(0.94 - \text{Hct} \times 100)(e^Z - 1)}{\left(e^Z - \frac{(0.94 - \text{Hct} \times 100)Q_B}{Q_D}\right)}$$

wherein $$Z = K_O A \frac{(Q_D - (0.94 - \text{Hct} \times 100)Q_B)}{((0.94 - \text{Hct} \times 100)Q_B \times Q_D)},$$

$$K_O A = \frac{(0.94 - \text{Hct} \times 100)Q_{B,M} \times Q_{D,M}}{Q_{D,M} - (0.94 - \text{Hct} \times 100)Q_{B,M}} \times$$

$$\ln\left(\frac{1 - K_{DM}/Q_{D,M}}{1 - K_{D,M}/[(0.94 - \text{Hct} \times 100)Q_{B,M}]}\right),$$

$Q_B$ is a blood flowrate, $Q_D$ is a dialysis flowrate, $K_O A$ is a dialyzer mass transfer area coefficient for phosphate obtained as a result of a previous measurement where a set of blood and dialysate flow rates $Q_{B,M}$ and $Q_{D,M}$ resulted in dialyzer clearance $K_{D,M}$, and Hct is hematocrit count measured from patient's blood sample.

3. The method of claim 1, wherein $K_D$ is determined for any time t using the equation:

$$K_D = \frac{C_D(t_s)Q_D(t_s)}{C(t_s)}$$

wherein $t_s$ is a sampling time, $C_D(t_s)$ is a concentration of phosphorus in a dialysate outflow at time $t_s$, $Q_D(t_s)$ is a dialysate flowrate at time $t_s$, and $C(t_s)$ is a serum phosphorus concentration at time $t_s$.

4. The method of claim 1, wherein $K_M$ is determined using the equation:

$$K_M = C_{POST}\left(\frac{K_D - Q_{UF}}{C_{PRE} - C_{POST}}\right).$$

5. The method of claim 1, wherein C of the patient is measured every 15 minutes during the hemodialysis treatment session.

6. The method of claim 1, wherein C of the patient is measured every 30 minutes during the hemodialysis treatment session.

7. The method of claim 1, wherein $t_{tx}$ is 2 hours.

8. The method of claim 1, wherein $t_{tx}$ is 4 hours.

9. The method of claim 1, wherein $t_{tx}$ is 8 hours.

10. The method of claim 1, wherein T is 30 minutes.

11. The method of claim 1, wherein T is 1 hour.

12. The method of claim 1 comprising determining $V_{POST}$ using the equation:

$$V_{POST} = V_{PRE} - Q_{UF} \times t_{tx}$$

and providing therapy to the patient based on the value of $V_{POST}$.

13. A method of predicting serum phosphorus concentrations in a patient during hemodialysis, the method comprising:

measuring serum phosphorus concentrations ("C") of the patient over a hemodialysis treatment session time for an ultrafiltration rate ("$Q_{UF}$")=0 during an initial hemodialysis treatment session;

estimating $K_M$ and $V_{PRE}$ for the patient using a non-linear least squares fitting to the equations:

$$C(t) = C_{PRE} \left[ \frac{K_M + (K_D + K_R)e^{-t\frac{(K_M + K_D + K_R)}{V_{PRE}}}}{K_M + K_D + K_R} \right] \text{ and}$$

$$C(T) = C_{PRE} - (C_{PRE} - C_{POST})e^{\left(-\frac{K_M T}{V_{PRE}}\right)}$$

wherein t is a time during the hemodialysis treatment session,

T is a time after an end of the hemodialysis treatment session, $t_{tx}$ is a total duration of the hemodialysis treatment session, $C_{PRE}$ is a pre-dialysis plasma phosphorus concentration, $C_{POST}$ is a post-dialytic plasma phosphorus concentration, $K_M$ is a phosphorus mobilization clearance of the patient, $K_R$ is a residual renal clearance of phosphate, $K_D$ is a dialyzer phosphate clearance, and $V_{PRE}$ is a pre-dialysis distribution volume of phosphorus of the patient; and predicting C of the patient at any time during any hemodialysis treatment session by using the equations 2-A and 2-B with the estimated $K_M$ and $V_{PRE}$ of the patient.

14. The method of claim 13, wherein $K_D$ is determined using the equation:

$$K_D = Q_B \frac{(0.94 - \text{Hct} \times 100)(e^Z - 1)}{\left(e^Z - \frac{(0.94 - \text{Hct} \times 100)Q_B}{Q_D}\right)}$$

wherein $$Z = K_O A \frac{(Q_D - (0.94 - \text{Hct} \times 100)Q_B)}{((0.94 - \text{Hct} \times 100)Q_B \times Q_D)},$$

$$K_O A = \frac{(0.94 - \text{Hct} \times 100)Q_{B,M} \times Q_{D,M}}{Q_{D,M} - (0.94 - \text{Hct} \times 100)Q_{B,M}} \times \ln\left(\frac{1 - K_{D,M}/Q_{D,M}}{1 - K_{D,M}/[(0.94 - \text{Hct} \times 100)Q_{B,M}]}\right),$$

$Q_B$ is a blood flowrate, $Q_D$ is a dialysis flowrate, $K_O A$ is a dialyzer mass transfer area coefficient for phosphate obtained as a result of a previous measurement where the set of blood and dialysate flow rates $Q_{B,M}$ and $Q_{D,M}$ resulted in dialyzer clearance $K_{D,M}$, and Hct is hematocrit count measured from patient's blood sample.

15. The method of claim 13, wherein $K_D$ is determined for any time t using the equation:

$$K_D = \frac{C_D(t_s)Q_D(t_s)}{C(t_s)}$$

wherein $t_s$ is a sampling time, $C_D(t_s)$ is a concentration of phosphorus in a dialysate outflow at time $t_s$, $Q_D(t_s)$ is a dialysate flowrate at time $t_s$, and $C(t_s)$ is a serum phosphorus concentration at time $t_s$.

16. The method of claim 13, wherein $K_M$ is determined using the equation:

$$K_M = C_{POST}\left(\frac{K_D - Q_{UF}}{C_{PRE} - C_{POST}}\right).$$

17. The method of claim 13, wherein C of the patient is measured every 15 minutes during the hemodialysis treatment session.

18. The method of claim 13, wherein C of the patient is measured every 30 minutes during the hemodialysis treatment session.

19. The method of claim 13, wherein $t_{tx}$ is 2 hours.

20. The method of claim 13, wherein $t_{tx}$ is 4 hours.

21. The method of claim 13, wherein $t_{tx}$ is 8 hours.

22. The method of claim 13, wherein T is 30 minutes.

23. The method of claim 13, wherein T is 1 hour.

24. The method of claim 13 comprising determining $V_{POST}$ using the equation:

$$V_{POST} = V_{PRE}$$

and providing therapy to the patient based on the value of $V_{POST}$.

25. A computing device comprising:

a display device;

an input device;

a processor; and a memory device that stores a plurality of instructions, which when executed by the processor, cause the processor to operate with the display device and the input device to:

(a) receive data relating to serum phosphorus concentrations ("C") of a hemodialysis patient over a hemodialysis treatment session time and an ultrafiltration rate ("$Q_{UF}$") calculated by a difference between pre- and post-dialytic body weight of the hemodialysis patient during a hemodialysis treatment session divided by a total treatment time of the treatment session;

(b) estimate $K_M$ and $V_{PRE}$ for the patient using a non-linear least squares fitting to the equations:

$$C(t) = C_{PRE} \left[ \frac{K_M + (K_D + K_R - Q_{UF})\left(\frac{V(t)}{V_{PRE}}\right)^{\frac{K_M + K_D + K_R - Q_{UF}}{Q_{UF}}}}{K_M + K_D + K_R - Q_{UF}} \right]$$

and $$C(T) = C_{PRE} - (C_{PRE} - C_{POST})e^{\left(-\frac{K_M T}{V_{PRE} - Q_{UF} t_{tx}}\right)}$$

wherein t is a time during the hemodialysis treatment session,

T is a time after an end of the hemodialysis treatment session, $t_{tx}$ is a total duration of the hemodialysis treatment session, $C_{PRE}$ is a pre-dialysis plasma phosphorus concentration, $C_{POST}$ is a post-dialytic plasma phosphorus concentration, $K_M$ is a phosphorus mobilization clearance of the patient, $K_R$ is a residual renal clearance of phosphate, $K_D$ is a dialyzer phosphate clearance, $V_{PRE}$ is a pre-dialysis distribution volume of phosphorus of the hemodialysis patient, and (c) predict C of the patient at any time during hemodialysis by using the equation 3-A and the estimated $K_M$ and $V_{PRE}$ of the patient.

26. The computing device of claim 25, wherein if $Q_{UF}=0$, then $$C(t) = C_{PRE}\left[\frac{K_M + (K_D + K_R)e^{-t\frac{(K_M+K_D+K_R)}{V_{PRE}}}}{K_M + K_D + K_R}\right]$$

and $$C(T) = C_{PRE} - (C_{PRE} - C_{POST})e^{\left(-\frac{K_M T}{V_{PRE}}\right)}.$$

27. The computing device of claim 25, wherein the processor operates with the display device and the input device to receive data relating to at least one of $K_R$, $K_D$ or a sampling time for collecting the serum phosphorus concentration.

28. A method of determining steady state, pre-dialysis serum phosphorus levels in a hemodialysis patient, the method comprising:

obtaining a net generation of phosphorus ("G") of the hemodialysis patient;

determining steady state, pre-dialysis serum phosphorus levels ("$C_{SS-PRE}$") of the hemodialysis patient using the equation:

$$C_{SS-PRE} = \frac{(G)(10080/F)}{(K_D + K_R)n\overline{C}_{tx}t_{tx} + K_R n\overline{C}_i(10080/F - t_{tx})} \quad \text{(eqn. 4-A)}$$

wherein F is a frequency of treatments per week, $t_{tx}$ is a treatment time for one hemodialysis treatment session, $K_D$ is a dialyzer phosphate clearance, $K_R$ is a residual renal clearance of phosphate, $n\overline{C}_{tx}$ is the normalized time averaged plasma phosphorus concentration during a dialysis treatment, and $n\overline{C}_i$ is the normalized time averaged plasma phosphorus concentration for an interdialytic interval; and simulating the effect of at least one of a patient parameter or a treatment parameter on $C_{SS-PRE}$ of the hemodialysis patient.

29. The method of claim 28, wherein $n\overline{C}_{tx}$ and $n\overline{C}_i$ are determined using the equations:

$$n\overline{C}_{tx} = \frac{1}{t_{tx}}\left\{\begin{array}{l}\left[\frac{K_M t_{tx}}{K_M + K_R + K_D - Q_{UF}}\right] + \\ \left[1 - \frac{K_M}{K_M + K_R + K_D - Q_{UF}}\right]\left[\frac{V_{PRE}}{K_M + K_R + K_D}\right]\left[1 - \\ \left(\frac{V_{POST}}{V_{PRE}}\right)^{(K_M+K_R+K_D)/Q_{UF}}\right]\end{array}\right\}$$

and, $$n\overline{C}_i = \frac{1}{10080/F - t_{tx}}\left\{\begin{array}{l}\left[\frac{K_M(10080/F - t_{tx})}{K_M + K_R + Q_{WG}}\right] + \\ \left[\begin{array}{l}\frac{K_M}{K_M + K_R + K_D - Q_{UF}} + \\ \left[1 - \frac{K_M}{K_M + K_R + K_D - Q_{UF}}\right] \\ \left[\frac{V_{POST}}{V_{PRE}}\right]^{(K_M+K_D+K_R-Q_{UF})/Q_{UF}} - \\ \frac{K_M}{K_M + K_R + Q_{WG}}\end{array}\right] \times \\ \left[\frac{V_{POST}}{K_M + K_R}\right]\left[1 - \left(\frac{V_{POST}}{V_{PRE}}\right)^{(K_M+K_R)/Q_{WG}}\right]\end{array}\right\},$$

wherein $K_M$ is a phosphorus mobilization clearance of the patient, $Q_{WG}$ is a constant rate of fluid gain by the patient during the interdialytic time interval, $Q_{UF}$ is a constant rate of fluid removed from the patient, $V_{PRE}$ is a pre-dialysis distribution volume of phosphorus of the patient prior to a hemodialysis treatment session, and $V_{POST}$ is a post-dialysis value of phosphorus of the patient at the end of a hemodialysis treatment session.

30. The method of claim 28, wherein there is negligible net ultrafiltration or fluid removal from the patient during hemodialysis therapies and no weight gain between hemodialysis therapies, $Q_{UF}=0$, and wherein $n\overline{C}_{tx}$ and $n\overline{C}_i$ are determined using the equations:

$$n\overline{C}_{tx} = \frac{1}{t_{tx}}\left\{\begin{array}{l}\left[\frac{K_M t_{tx}}{K_M + K_R + K_D}\right] + \left[1 - \frac{K_M}{K_M + K_R + K_D}\right] \\ \left[\frac{V_{PRE}}{K_M + K_R + K_D}\right][1 - \exp(-(K_D + K_R + K_M)t_{tx}/V_{PRE})]\end{array}\right\}$$

and, $$n\overline{C}_i = \frac{1}{10080/F - t_{tx}}\left\{\begin{array}{l}\left[\frac{K_M(10080/F - t_{tx})}{K_M + K_R}\right] + \\ \left[\begin{array}{l}\frac{K_M}{K_M + K_R + K_D} + \\ \left[1 - \frac{K_M}{K_M + K_R + K_D}\right] \times \\ \exp[-(K_D + K_R + K_M)t_{tx}/V_{PRE}] - \\ \frac{K_M}{K_M + K_R}\end{array}\right] \times \\ \left[\frac{V_{POST}}{K_M + K_R}\right] \\ [1 - \exp(-(K_R + K_M)(10080/F - t_{tx})/V_{POST})]\end{array}\right\},$$

wherein $K_M$ is a phosphorus mobilization clearance of the patient, $V_{PRE}$ is a pre-dialysis distribution volume of phosphorus of the patient prior to a hemodialysis treatment session, and $V_{POST}$ is a post-dialysis value of phosphorus of the patient at the end of a hemodialysis treatment session.

31. The method of any one of claim 29 or 30, wherein the patient parameter is G, $K_M$ or $V_{PRE}$.

32. The method of claim 29 or 30, wherein the treatment parameter is $t_{tx}$, $K_D$ or F.

33. The method of claim 29 or 30, wherein $K_M$ is determined using the equation:

$$K_M = C_{POST}\left(\frac{K_D - Q_{UF}}{C_{PRE} - C_{POST}}\right)$$

wherein $C_{POST}$ is a post-dialytic plasma phosphorus concentration, and $C_{PRE}$ is a pre-dialysis plasma phosphorus concentration.

34. The method of claim 28, wherein G is calculated using the equation:

$$G = C_{SS-PRE-IN} \times \left[\frac{(K_D + K_R)n\bar{C}_{tx}t_{tx} + K_R n\bar{C}_i(10080/F - t_{tx})}{10080/F}\right]$$

wherein $C_{SS-PRE-IN}$ is an initial, measured, steady state, pre-dialysis serum phosphorus level of the hemodialysis patient who is maintained by a hemodialysis therapy identified by $K_D$, F and $t_{tx}$ for a specified time prior to the calculation of G using equation 4-G, F is a frequency of treatments per week, $t_{tx}$ is a treatment time for one hemodialysis treatment session, $K_D$ is a dialyzer phosphate clearance, $K_R$ is a residual renal clearance of phosphate, $n\bar{C}_{tx}$ is the normalized time averaged plasma phosphorus concentration during a dialysis treatment, and $n\bar{C}_i$ is the normalized time averaged plasma phosphorus concentration for an interdialytic interval.

35. The method of claim 28, wherein $K_D$ is determined using the equation:

$$K_D = Q_B \frac{(0.94 - Hct \times 100)(e^Z - 1)}{\left(e^Z - \frac{(0.94 - Hct \times 100)Q_B}{Q_D}\right)}$$

wherein $$Z = K_O A \frac{(Q_D - (0.94 - Hct \times 100)Q_B)}{((0.94 - Hct \times 100)Q_B \times Q_D)},$$

$$K_O A = \frac{(0.94 - Hct \times 100)Q_{B,M} \times Q_{D,M}}{Q_{D,M} - (0.94 - Hct \times 100)Q_{B,M}} \times \ln\left(\frac{1 - K_{D,M}/Q_{D,M}}{1 - K_{D,M}/[(0.94 - Hct \times 100)Q_{B,M}]}\right),$$

$Q_B$ is a blood flowrate, $Q_D$ is a dialysis flowrate, $K_O A$ is a dialyzer mass transfer area coefficient for phosphate obtained as a result of a previous measurement where the set of blood and dialysate flow rates $Q_{B,M}$ and $Q_{D,M}$ resulted in dialyzer clearance $K_{D,M}$, and Hct is hematocrit count measured from patient's blood sample.

36. The method of claim 28, wherein $K_D$ is determined for any time t using the equation:

$$K_D = \frac{C_D(t_s)Q_D(t_s)}{C(t_s)}$$

wherein $t_s$ is a sampling time, $C_D(t_s)$ is a concentration of phosphorus in a dialysate outflow at time $t_s$, $Q_D(t_s)$ is a dialysate flowrate at time $t_s$, and $C(t_s)$ is a serum phosphorus concentration at time $t_s$.

37. The method of claim 28, wherein G is determined using the equation:

$$G = \frac{I_P A_P - I_B P_B}{10080}$$

wherein $I_P$ is a weekly dietary intake of phosphorus of the hemodialysis patient, $A_P$ is a percent phosphorus absorption of the hemodialysis patient, $I_B$ is a weekly binder intake of the hemodialysis patient, and $P_B$ is a binding power of the binder.

38. The method of claim 28 comprising determining a level of phosphorus intake so that $C_{SS-PRE}$ of the hemodialysis patient ranges between about 3.6 mg/dl and 5.0 mg/dl.

39. The method of claim 28 comprising determining a phosphorus binder administered to the patient so that $C_{SS-PRE}$ of the hemodialysis patient ranges between about 3.6 mg/dl and 5.0 mg/dl.

40. The method of claim 28 comprising determining the total hemodialysis treatment session time so that $C_{SS-PRE}$ of the hemodialysis patient ranges between about 3.6 mg/dl and 5.0 mg/dl.

41. The method of claim 28 comprising determining the frequency F so that $C_{SS-PRE}$ of the hemodialysis patient ranges between about 3.6 mg/dl and 5.0 mg/dl.

42. The method of claim 28 comprising determining a required blood flowrate and/or a dialysate flowrate so that $C_{SS-PRE}$ of the hemodialysis patient ranges between about 3.6 mg/dl and 5.0 mg/dl.

43. The method of claim 28 comprising determining an amount of phosphorus salt supplements added to the dialysate so that $C_{SS-PRE}$ of the hemodialysis patient ranges between about 3.6 mg/dl and 5.0 mg/dl.

44. The method of claim 28, wherein $K_M$ and $V_{PRE}$ are determined by measuring serum phosphorus concentrations ("C") of the hemodialysis patient over a hemodialysis treatment session time and an ultrafiltration rate ("$Q_{UF}$") calculated by a difference between pre- and post-dialytic body weight of the patient during an initial hemodialysis treatment session divided by a total treatment time of the treatment session, and calculating $K_M$ and $V_{PRE}$ for the hemodialysis patient using a non-linear least squares fitting to the equations:

$$C(t) = C_{PRE}\left[\frac{K_M + (K_D + K_R - Q_{UF})\left(\frac{V(t)}{V_{PRE}}\right)^{\frac{K_M+K_D+K_R-Q_{UF}}{Q_{UF}}}}{K_M + K_D + K_R - Q_{UF}}\right]$$

and $$C(T) = C_{PRE} - (C_{PRE} - C_{POST})e^{\left(-\frac{K_M T}{V_{PRE} - Q_{UF} t_{tx}}\right)}$$

wherein t is a time during the hemodialysis treatment session,

T is a time after an end of the hemodialysis treatment session,
$t_{tx}$ is a total duration of the hemodialysis treatment session,
$C_{PRE}$ is a pre-dialysis plasma phosphorus concentration,
$C_{POST}$ is a post-dialytic plasma phosphorus concentration,
$K_M$ is a phosphorus mobilization clearance of the patient,
$K_R$ is a residual renal clearance of phosphate,
$K_D$ is a dialyzer phosphate clearance,
$V_{PRE}$ is a pre-dialysis distribution volume of phosphorus of the patient, and $$V(t) = V_{PRE} - Q_{UF} \times t.$$

45. A computing device comprising:
a display device;
an input device;
a processor; and
a memory device that stores a plurality of instructions, which when executed by the processor, cause the processor to operate with the display device and the input device to:
(a) receive data relating to a net generation of phosphorus ("G") from at least a dietary phosphorus intake of a hemodialysis patient or a urea kinetic modeling of the hemodialysis patient;
(b) determine steady state, pre-dialysis serum phosphorus levels ("$C_{SS-PRE}$") of the patient using the equation:

$$C_{SS-PRE} = \frac{(G)(10080/F)}{(K_D + K_R)n\overline{C}_{tx}t_{tx} + K_R n\overline{C}_i(10080/F - t_{tx})},$$

wherein F is a frequency of treatments per week,
$t_{tx}$ is a treatment time for one hemodialysis treatment session,
$K_D$ is a dialyzer phosphate clearance,
$K_R$ is a residual renal clearance of phosphate,
$n\overline{C}_{tx}$ is the normalized time averaged plasma phosphorus concentration during a dialysis treatment, and
$n\overline{C}_i$ is the normalized time averaged plasma phosphorus concentration for an interdialytic interval; and
(c) simulate the effect of at least one of a patient parameter or a treatment parameter on the $C_{SS-PRE}$ of the hemodialysis patient.

46. The computing device of claim 45, wherein the processor operates with the display device and the input device to receive data relating to at least one of $K_R$, $K_D$, $K_M$, $V_{PRE}$, $t_{tx}$, F, $C_{PRE}$ about a month before a hemodialysis treatment session or a sampling time for collecting the serum phosphorus concentration.

47. The computing device of claim 45, wherein the computing device displays a treatment regimen of the hemodialysis patient so that $C_{SS-PRE}$ is within a desired range.

48. A computing device comprising:
a display device;
an input device;
a processor; and
a memory device that stores a plurality of instructions, which when executed by the processor, cause the processor to operate with the display device and the input device to:
(a) determine a net generation of phosphorus ("G") using the equation:

$$G = C_{SS-PRE-IN} \times \left[ \frac{(K_D + K_R)n\overline{C}_{tx}t_{tx} + K_R n\overline{C}_i(10080/F - t_{tx})}{(10080/F)} \right]$$

wherein $C_{SS-PRE-IN}$ is an initial, measured, steady state, pre-dialysis serum phosphorus level of the hemodialysis patient who is maintained by a hemodialysis therapy identified by $K_D$, F and $t_{tx}$ for a specified time prior to the calculation of G using equation 6-A,
F is a frequency of treatments per week,
$t_{tx}$ is a treatment time for one hemodialysis treatment session,
$K_D$ is a dialyzer phosphate clearance,
$K_R$ is a residual renal clearance of phosphate,
$n\overline{C}_{tx}$ is the normalized time averaged plasma phosphorus concentration during a dialysis treatment, and
$n\overline{C}_i$ is the normalized time averaged plasma phosphorus concentration for an interdialytic interval;
(b) predict steady state, pre-dialysis serum phosphorus levels ("$C_{SS-PRE}$") of the hemodialysis patient using the equation:

$$C_{SS-PRE} = \frac{(G)(10080/F)}{(K_D + K_R)n\overline{C}_{tx}t_{tx} + K_R n\overline{C}_i(10080/F - t_{tx})};$$

and
(c) simulate the effect of at least one of a patient parameter or a treatment parameter on $C_{SS-PRE}$ of the hemodialysis patient.

49. The computing device of claim 48, wherein the processor operates with the display device and the input device to receive data relating to at least one of $K_R$, $K_D$, $K_M$, $V_{PRE}$, $t_{tx}$, F, $C_{PRE}$ about a month before a hemodialysis treatment session or a sampling time for collecting the serum phosphorus concentration.

50. The computing device of claim 48, wherein the computing device displays a treatment regimen of the hemodialysis patient so that $C_{SS-PRE}$ is within a desired range.

* * * * *

UNITED STATES PATENT AND TRADEMARK OFFICE
CERTIFICATE OF CORRECTION

PATENT NO. : 8,868,350 B2
APPLICATION NO. : 13/088044
DATED : October 21, 2014
INVENTOR(S) : Akonur et al.

Page 1 of 2

It is certified that error appears in the above-identified patent and that said Letters Patent is hereby corrected as shown below:

In the Claims,

In Claim 1, Column 37, line 55, after $$C(t) = C_{PRE} \left[ \frac{K_M + (K_D + K_R - Q_{UF})\left(\frac{V(t)}{V_{PRE}}\right)^{\frac{K_M + K_D + K_R - Q_{UF}}{Q_{UF}}}}{K_M + K_D + K_R - Q_{UF}} \right],$$

" add ---"(eqn. 1-A)"---

In Claim 1, Column 37, line 61, after $$C(T) = C_{PRE} - (C_{PRE} - C_{POST}) e^{\left(-\frac{K_M T}{V_{PRE} \cdot Q_{UF} \cdot t_\alpha}\right)},$$

" add ---"(eqn. 1-B)"---

In Claim 13, Column 39, line 20, after $$C(t) = C_{PRE} \left[ \frac{K_M + (K_D + K_R)e^{-t\frac{(K_M + K_D + K_R)}{V_{PRE}}}}{K_M + K_D + K_R} \right],$$

" add ---"(eqn. 2-A)"---

In Claim 13, Column 39, line 25, after $$C(T) = C_{PRE} - (C_{PRE} - C_{POST}) e^{\left(-\frac{K_M T}{V_{PRE}}\right)},$$

" add ---"(eqn. 2-B)"---

Signed and Sealed this
Third Day of March, 2015

Michelle K. Lee
*Deputy Director of the United States Patent and Trademark Office*

CERTIFICATE OF CORRECTION (continued)
U.S. Pat. No. 8,868,350 B2

In Claim 25, Column 41, line 20, delete ""by using the equation 3-A""

In Claim 34, Column 43, line 29, delete ""using equation 4-G""

In Claim 48, Column 46, lines 19-20, delete ""using equation 6-A""